(12) United States Patent
Bazin et al.

(10) Patent No.: US 8,178,704 B2
(45) Date of Patent: May 15, 2012

(54) INOSITOL-PHOSPHATE DERIVATIVES AND METHOD OF DETECTING INOSITOL-1-PHOSPHATE

(75) Inventors: Hervé Bazin, Villeneuve les Avignon (FR); Hervé Ansanay, Tavel (FR); Eric Trinquet, Pont Saint Esprit (FR); Gérard Mathis, Bagnols sur Ceze (FR)

(73) Assignee: CIS Bio International, Saclay (FR)

( * ) Notice: Subject to any disclaimer, the term of this patent is extended or adjusted under 35 U.S.C. 154(b) by 398 days.

(21) Appl. No.: 11/792,135

(22) PCT Filed: Dec. 2, 2005

(86) PCT No.: PCT/FR2005/051032
§ 371 (c)(1),
(2), (4) Date: Apr. 2, 2008

(87) PCT Pub. No.: WO2006/059052
PCT Pub. Date: Jun. 8, 2006

(65) Prior Publication Data
US 2008/0261237 A1 Oct. 23, 2008

(30) Foreign Application Priority Data
Dec. 2, 2004 (FR) ...................................... 04 12797

(51) Int. Cl.
*C07F 9/02* (2006.01)
*G01N 33/53* (2006.01)
(52) U.S. Cl. ............ 554/79; 568/833; 435/7.1; 435/7.9; 422/61
(58) Field of Classification Search .................... 554/79; 568/833; 435/7.1, 7.9; 422/61
See application file for complete search history.

(56) References Cited

U.S. PATENT DOCUMENTS

| | | | |
|---|---|---|---|
| 4,927,923 A | 5/1990 | Mathis et al. | |
| 5,264,605 A | 11/1993 | Ozaki et al. | |
| 5,457,184 A | 10/1995 | Lehn et al. | |
| 5,527,684 A | 6/1996 | Mabile et al. | |
| 2001/0056072 A1 | 12/2001 | Martin-Lomas et al. | |
| 2004/0106158 A1 | 6/2004 | Naqvi et al. | |

FOREIGN PATENT DOCUMENTS

| | | |
|---|---|---|
| EP | 0 180 492 | 5/1986 |
| EP | 0 321 353 | 6/1989 |
| WO | WO-91 00258 | 1/1991 |
| WO | WO-92 13264 | 8/1992 |

(Continued)

OTHER PUBLICATIONS

Berridge, M. J. et al., "Changes in the levels of inositol phosphates after agonist-dependent hydrolysis of memebrane phosphoinositides," Biochem. J., 1983, vol. 212, pp. 437-482.

(Continued)

*Primary Examiner* — Jezia Riley
(74) *Attorney, Agent, or Firm* — Millen, White, Zelano & Branigan, P.C.

(57) ABSTRACT

The present invention relates to inositol phosphate derivatives, in which the inositol phosphate is substituted with one or two reactive groups G or one or two conjugated substances or molecules M, said reactive group(s) G or said substance(s) or molecule(s) M being linked to IP1 via a linkage group L, M being chosen from the following group: a tracer, an immunogen, a member of a binding partner pair, a solid support.
Application: tools allowing the study of the inositol phosphate cycle and therefore, indirectly, the study of seven transmembrane domain receptors coupled to phospholipase C, receptors having a tyrosine kinase activity, and in general enzymes involved in the variations of the intracellular concentration of IP1.

66 Claims, 20 Drawing Sheets

FOREIGN PATENT DOCUMENTS

| | | |
|---|---|---|
| WO | WO-93 05049 | 3/1993 |
| WO | WO-01 85740 | 11/2001 |
| WO | WO-2003 087109 | 10/2003 |

OTHER PUBLICATIONS

Billington, D. C. et al., "The total synthesis of myo-Inositol phosphates via myo-inositol Orthoformate," J. Chem. Soc. Perkin Trans., 1989, pp. 1423-1429.

Brandish, P. E. et al., "Scintillation proximity assay of inositol phosphates in cell extracts: High-throughput measurement of G-protein-coupled receptor activation," Analytical Biochemistry, 2003, vol. 313, pp. 311-318.

Chengalvala, M. et al., "A multi-well filtration assay for quantitation of inositol phosphates in biological simples," J. Biochem. Biophys. Methods, 1999, vol. 38, pp. 163-170.

Dreef, C. E. et al., "Synthesis of Racemic 3-Methylphosphonate Analogues of Myo-Inositol 3,4-bis and 1,3,4-Trisphosphate," Tetrahedron, 1991, vol. 47, No. 26, pp. 4709-4722.

Garegg, P. J. et al., "Synthesis of some mono-O-benzyl- and penta-O-methyl-myo-inositols," Carbohydrate Research, 1984, vol. 130, pp. 322-326.

Gigg, J. et al., "The Allyl Group for Protection in Carbohydrate Chemistry. Part 18.[1] Allyl and Benzyl Ethers of myo-Inositol. Intermediates for the Synthesis of myo-Inositol Trisphophates," J. Chem. Soc. Perkin. Trans., 1987, pp. 423-429.

Gou, D. et al., "An Efficient Chemoenymic access to optically active myo-inositol polyphosphates," Carbohydrate Research, 1992, vol. 234, pp. 51-64.

Hermanson, G. T. et al., Bioconjugate Techniques, 2008, pp. 298-364.

Hermanson, G. T. et al., Bioconjugate Techniques, 2008, pp. 373-400.

Jaramillo, C. et al., "An Effective Strategy for the Synthesis of 6-O-(2-Amino-2-deoxy-alpha-D-glucopyranosyl)-D-chiro- and -D-myo-inositol 1-Phosphate Related to Putative Insulin Mimetics," J. Org. Chem., 1994, vol. 59, pp. 3135-3141.

Kohler, G. et al., "Continuous cultures of fused cells secreting antibody of predefined specificity," Nature Aug. 7, 1975, pp. 495-497.

Kricka, L. J. et al., "Nonisotopic Probing, Blotting, and Sequencing," 1995, Second Edition, pp. 66-72.

Liu, J. J. et al., "An immobilized metal ion affinity adsorption and scintillation proximity assay for receptor-stimulated phosphoinositide hydrolysis," Analytical Biochemistry, 2003, vol. 318, pp. 91-99.

Mathis, Gerard, "Rare earth cryptates and homogeneous fluoroimmunoassays with human sera," Clin. Chem., 1993, vol. 39, No. 3, pp. 1953-1959.

Moitessier, N. et al., "Synthesis and Biological Activities of Inositol 1, 4, 5-Trisphosphate Mimics Related to Xylopyranosides," Tetrahedron Letters, 1995, vol. 36, No. 44, pp. 8023-8026.

Parthasarathy, L. et al., "Biochemical and Molecular Properties of Lithium-Sensitive Myo-inositol Monophosphatase," Life Sciences, 1994, vol. 54, No. 16, pp. 1127-1142.

Prestwich, G. D. et al., "Tethered IP$_3$- Synthesis and Biochemical Applications of the 1-o-(3-Aminopropyl) Ester of Inositol 1,4,5-Trisphosphate," J. Am. Chem. Soc., 1991, vol. 114, pp. 1822-1825.

Ragan, C. I. et al., "The dephosphorylation of inositol 1,4-bisphosphate to inositol in liver and brain involves two distinct Li$^+$-senstive enzymes and proceeds via inositol 4-phosphate," Biochem. J., 1988, vol. 249, pp. 143-148.

Thomson Innovation, English Translation of Description and Claims for EP0321353, Retrieved from Patent Record View on Sep. 16, 2010.

Vacca, J. P. et al., "The Total Synthesis of Myo-Inositol Polyphosphates," Tetrahedron, 1989, vol. 45, No. 17, pp. 5679-5702.

Wang, D. et al., "Synthesis of the D-3 Series of Phosphatidylinositol Phosphates," J. Org. Chem., 1996, vol. 61, pp. 5905-5910.

Wright, J. A. et al., "Sequential removal of the Benzyl-type protecting groups PMB and NAP by oxidative cleavage using CAN and DDQ," Tetrahedron Letters, 2001, vol. 42, pp. 4033-4036.

Zheng, W. et al., "High-throughput Cell-Based Screening Using Scintillation Proximity Assay for the Discovery of Inositol Phosphate Inhibitors," Journal of Biomolecular Screeings, 2004, vol. 9, No. 132.

Berlin, W. K. et al., "Glycosyl-Inositol Derivatives III. Synthesis of Hexosamine-Inositol-Phosphates Related to Putative Insulin Mediators'," Tetrahedron, 1991, vol. 47, No. 1, pp. 1-20.

Chen, J. et al., "Aysmmetric Total Synthesis of Phosphatidylinositol 3-Phosphate and 4-Phosphate Derivatives," J. Org. Chem., 1998, vol. 63, pp. 6511-6522.

Cobb, J. E. et al., "Synthesis of 6-O-(2-Aminoethyl)-D,L-Myo-Inositol-1,2-Cyclic Phosphate: A Model Of A Putatives Insulin Second Messenger," Tetrahedron, 1991, vol. 47, No. 1, pp. 21-30.

Cottaz, S. et al., "Parasite glycoconjugates. Part 3.[1] Synthesis of substrate analogues of early intermediates in the biosynthetic pathway of glycosylphatidylinositol membrane anchors," J. Chem. Soc. Perkin. Trans., vol. 1, 1995, pp. 1673-1678.

Essen, L. O. et al., "Structural Analysis of the Catalysis and Membrane Association of PLC-$\delta^1$," ACS Symposium Series, 1999, pp. 121-136.

Falck, J. R. et al., "Concise synthesis of L-alpha-phosphatidyl-D-myo-inositol 3-phosphate (3-PIP), 5- phosphate (5-PIP), and 3,5-bisphosphate (3,5-PIP$_2$)," Tetrahedron Letters, 2000, vol. 41, pp. 4271-4275.

Greene, T. W. et al., "Protective Groups in Orangic Synthesis," Second Edition, pp. 10-14 & 406-423.

Krauter, T. et al., "Phospholipids as Modulators of K$^{ATP}$Channels: Distinct Mechanisms for Control of Sensitivity to Sulphonylureas, K$^+$ Channel Openers, and ATP," Molecular Pharmacology, 2001, vol. 59, No. 5, pp. 1086-1093.

Watanabe, Y. et al., "An efficient Phosphorylation Method Using a New Phosphitylating Agent, 2-Diethylamino-1,3,2-Benzodioxaphosphepane, "Tetrahedron Letters, 1990, vol. 31, No. 2, pp. 255-256.

Watanabe, Y. et al., "Phosphonium Salt Methodology for the Synthesis of Phosphoric Monoesters and Diesters and its Application to Selective Phosphorylation," 1993, vol. 34, No. 3, pp. 497-500.

FIGURE 1 (CONTINUED)
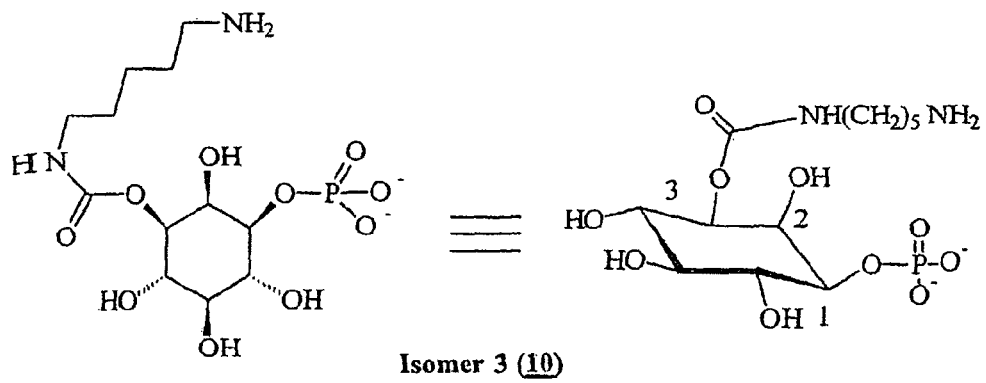
Isomer 3 (10)
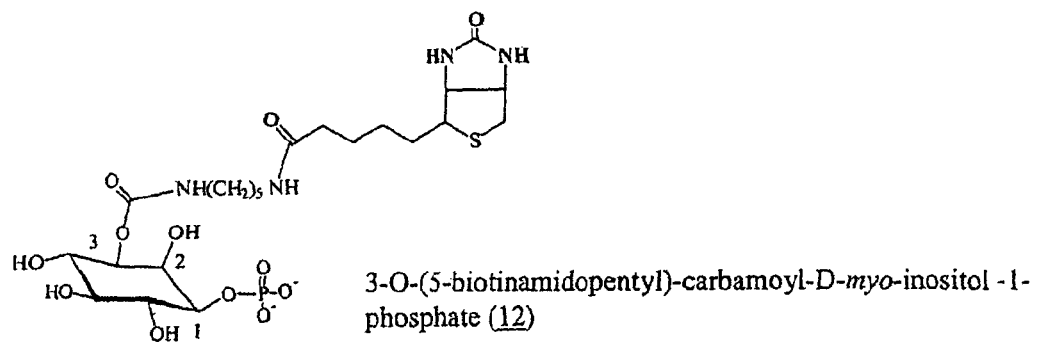
3-O-(5-biotinamidopentyl)-carbamoyl-D-*myo*-inositol-1-phosphate (12)
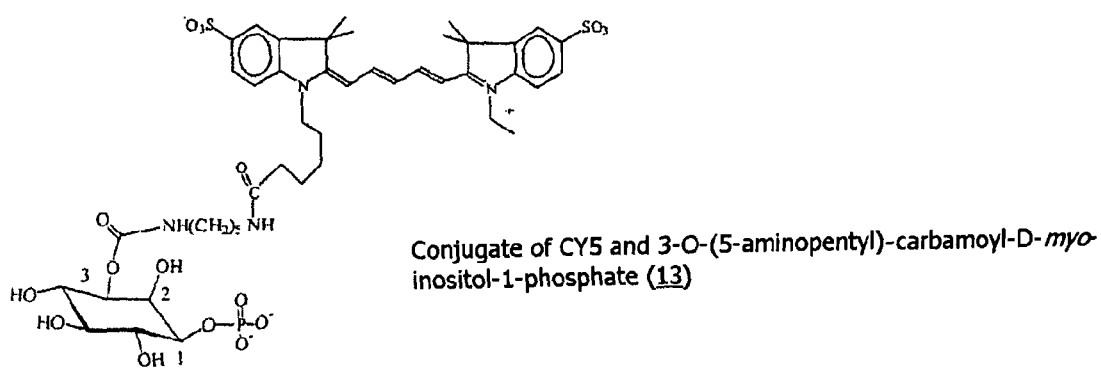
Conjugate of CY5 and 3-O-(5-aminopentyl)-carbamoyl-D-*myo*-inositol-1-phosphate (13)

FIGURE 5
3-O-(4-carboxy-butyramido-5-pentyl)-carbamoyl-D-*myo*-inositol-1-phosphate (31)
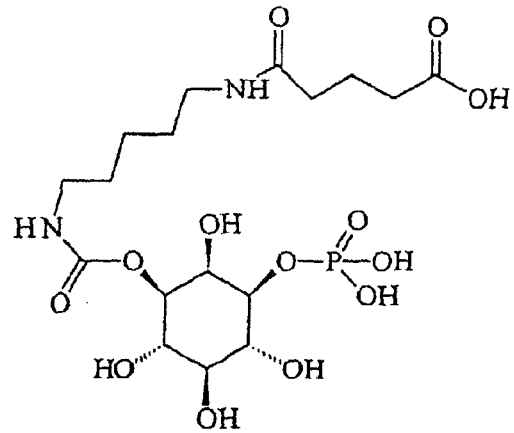
N-hydroxysuccinimide ester of 3-O-(4-carboxy-butyramido-5-pentyl)-carbamoyl-D-*myo*-inositol-1-phosphate (32)
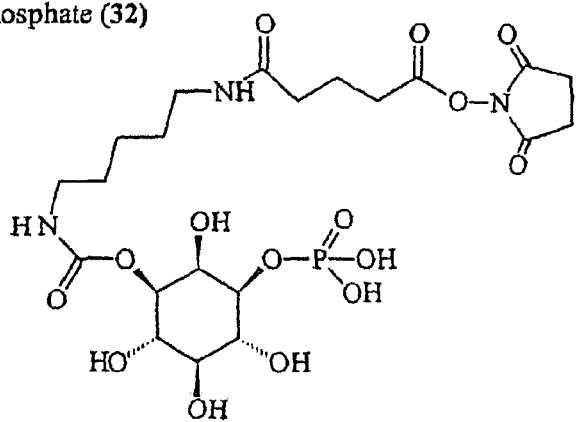
3-O-[5-(3-maleimidopropionamido)pentyl]-carbamoyl-D-*myo*-inositol-1-phosphate (33)
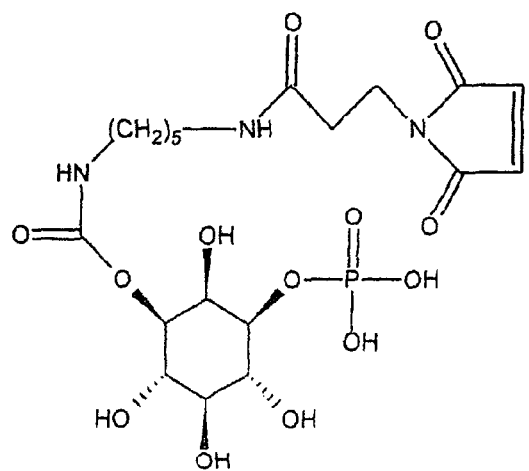

Method for the synthesis of *myo*-inositol-1-phosphate analogs containing a reactive group at the 4 or 5 position 4-O-(5-biotinamidopentyl)-carbamoyl-D-myo-inositol-1-phosphate (43 D)

5-O-(5-biotinamidopentyl)-carbamoyl-D-myo-inositol-1-phosphate (44 D)

Method for the synthesis of *myo*-inositol-4-phosphate analogs containing a reactive group G at the 6-position

50D

Method for the synthesis of *myo*-inositol-4-phosphate analogs containing a reactive group G at the 1-position Method for the synthesis of *myo*-inositol-4-P analogs containing a reactive group at the 2- or 3-position

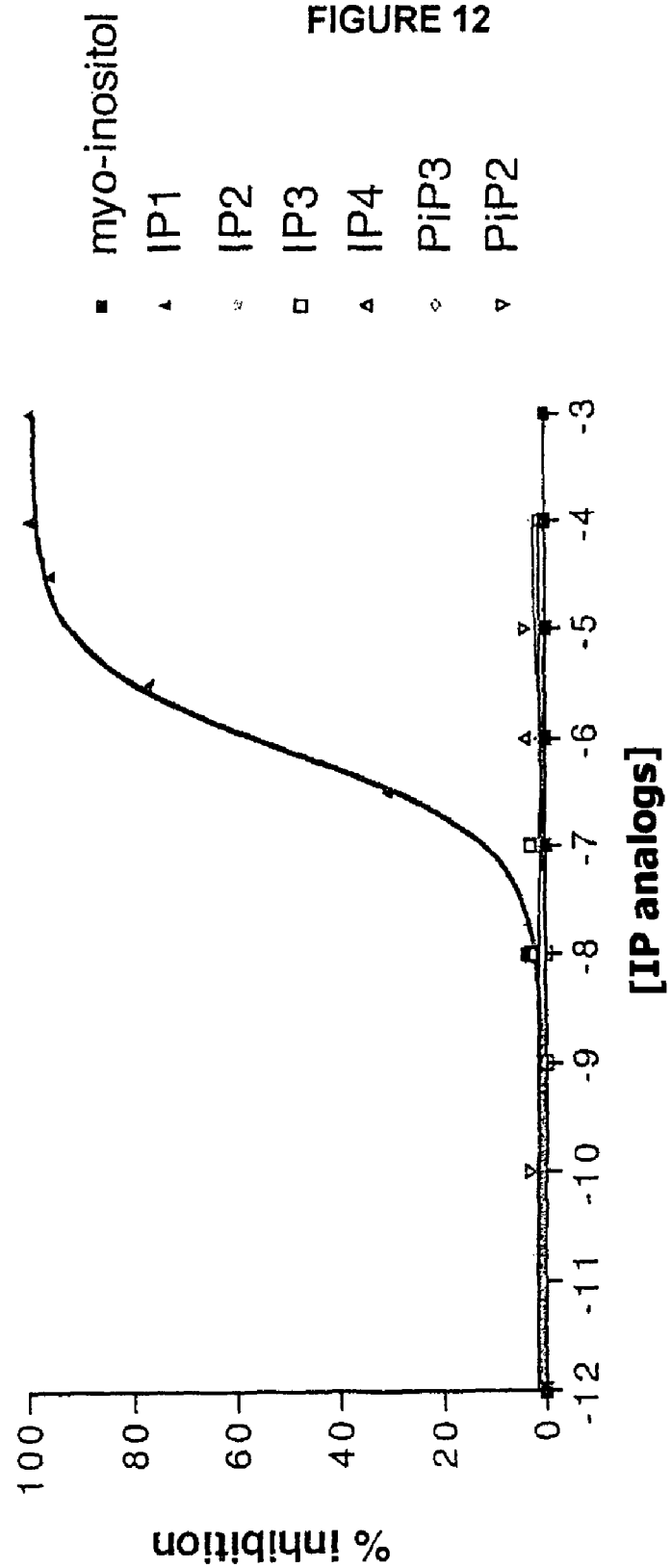

INOSITOL-PHOSPHATE DERIVATIVES AND METHOD OF DETECTING INOSITOL-1-PHOSPHATE

TECHNICAL FIELD AND PRIOR ART

The subject of the present invention is inositol phosphate derivatives and provides novel tools allowing the study of the inositol phosphate cycle and therefore, indirectly, the study of seven transmembrane domain receptors (7TM receptors) coupled to phospholipase C (PLC), receptors having a tyrosine kinase activity, and in general enzymes involved in the variations of the intracellular concentration of IP1.

The term "inositol phosphate" denotes a compound of the cyclitol family of the cyclohexane type containing a hydroxyl group on each carbon (1,2,3,4,5,6-hexahydroxy-cyclohexanes). The natural compound the most widely represented is myo-inositol, whose hydroxyl groups at the 1, 2, 3 and 5 positions are located on one of the faces of the cyclohexane ring and the two hydroxyl groups at the 4 and 6 positions are located on the other face. The natural compounds produced during the inositol phosphate cycle are D-myo-inositol phosphates, in which the phosphate is at the 1, 3, 4 or 5 position of the inositol ring. These compounds are generally called "IP1", by contrast for example to IP2 (inositol bisphosphate) or IP3 (inositol trisphosphate). In the remainder of the text, these compounds will be designated by the following acronyms respectively: IP1(1), IP1(3), IP1(4), IP1(5) and have the formulae:

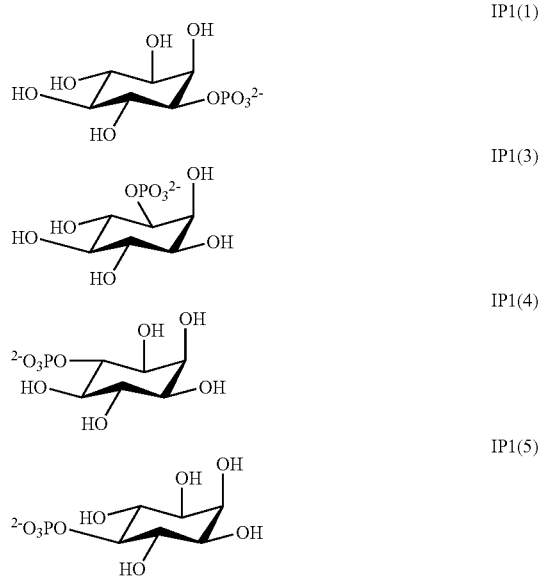

IP1(1) and IP1(4) are the intermediates the most widely studied.

The G protein coupled seven transmembrane domain receptors (GPCR, 7 TM) are involved in numerous pathological processes. They have in particular the function of transmitting signals from the extracellular medium to the intracellular medium across the cell membrane. Molecules playing a role of messenger in the body, such as hormones, growth factors, cytokines or neurotransmitters, will bind to these receptors and trigger a cascade of events inside the cell.

The study of the behavior of these receptors in the presence of compounds capable of being used as medicaments is one of the methods of choice which make it possible to discover novel treatments. One of the routes widely used for studying the activation or deactivation of these receptors consists in measuring the variations in intracellular messenger concentration during the binding of potential medicaments to these receptors. Tools which make it possible to measure the variations in these intracellular messengers are therefore very valuable in pharmaceutical research, but also in basic research work aimed at better understanding the mechanisms of inter-/intracellular signaling.

The binding of an agonist ligand to a 7TM receptor will modify the tertiary structure of the receptor, which in turn induces a modification of the conformation of a G protein coupled to the receptor. The activation of this G protein will in turn cause, depending on the cases, either the activation or the inhibition of an effector which will produce a second intracellular messenger such as CAMP or IP3.

One of these effectors is phospholipase C (PLC) which induces the hydrolysis of membrane phosphatidylinositol 4,5-biphosphate (PIP2) to diacylglycerol (DAG) and to inositol trisphosphate ($IP_3$). $IP_3$ in turn causes an increase in the concentration of intracellular $Ca^{2+}$ by activation of $IP_3$ receptors present on the endoplasmic reticulum. This $IP_3$ has a very rapid half-life time (less than one minute) because it is either immediately phosphorylated at its 3 position, giving inositol 1,3,4,5-tetrakisphosphate ($IP_4$), or degraded to IP2 by a specific phosphatase. IP4 and IP2 are then rapidly degraded by a series of enzymes (5-, 3-, 4- or 1-PPASEs) to give predominantly IP1(1) and IP1(4) but also IP1(3) and IP1(5). These inositol monophosphates have a tendency to accumulate before being degraded to inositol by the action of inositol monophosphatase (IMPase). This final degradation may be artificially slowed down by the use of IMPase inhibiting lithium salts [Parthasarathy et al. *Life Sci.* (1994), 54, 1127-1142], allowing accumulation of IP1 in the cell and facilitating the optional assay of this intermediate. The combination of the conversions of these inositol derivatives is called the inositol cycle. The IP1 produced by the activation of the inositol cycle is one of these intracellular messengers and its assay makes it possible to detect the modulation of the signaling pathway involving phospholipase C.

The IP1 assays described in the literature are based mainly on radioisotope methods [Berridge et al. *Biochem J.* (1983) 212, 473-82]. Cells are incubated in the presence of tritiated inositol (48 h) and of lithium chloride in order to avoid the enzymatic degradation of the IP1 formed. The cells are treated with an agent stimulating the membrane receptors (agonist neuromediator) and are then lysed and the inositol as well as all the inositol phosphates (IP3, IP2, IP4, IP1) of the cytosolic fraction are deposited on an anion-exchange column and this column is eluted with an ammonium formate gradient; the tritium-labeled IP1 is collected at a given ionic strength, the radioactivity measured thus makes it possible to estimate the quantity of the IP1 formed by the stimulation of the cells. This technique, which is quite difficult to control, has the disadvantage of using radioisotopes and does not allow absolute quantification of the IP1 formed; furthermore, this method does not allow a large number of simultaneous assays. Nevertheless, it has been possible to miniaturize it [Chengalvala et al. *J Biochem. Biophys. Methods* (1999), 38, 163-170] in order to partially respond to the needs, such as the high throughput screening of molecules.

Other techniques using tritiated inositides [Zheng W et al. *J Biomol Screen.* (2004) 9(2):132-40], [Brandish P. E. et al. *Anal. Biochem.* (2003) 313, 311-318] and [Liu J J et al. *Anal Biochem.* 2003 Jul. 1; 318(1):91-9] have been proposed; the difference with the preceding isotope technique lies essentially in the measurement. In these techniques, use is made of a scintillation proximity assay (SPA) using a solid phase coated with a metallic complex having affinity for the phosphate groups [Liu et al., Anal Biochem (2003)]. In this case, all the phosphorylated intermediates (IP1, IP2, IP3 etc.) are assayed together and selectivity is only possible between the inositol and the inositol phosphates. This technique is better suited to high throughput screening and makes it possible to carry out many simultaneous assays but obviously lacks selectivity and does not make it possible to assay IP1 alone.

In order to be able to carry out a nonradioactive assay of IP1, it is necessary to have a functionalized analog of IP1 having a defined stereochemistry. As myo-inositol is a molecule which has a plane of symmetry, it is therefore not optically active (so-called "meso" compound whose optical activity is destroyed by the existence of a symmetry), and its phosphorylation can lead, for example, to two possible enantiomers which are D-myo-inositol-1-phosphate and L-myo-inositol-1-phosphate, the D enantiomer being produced in the cell by the inositol cycle. The IP3 derivatives described in the literature [Prestwich et al. *J. Amer. Chem. Soc.* (1991)] are functionalized on the phosphate at the 1 position; as a result, they are scarcely suitable for generating antibodies specific for IP1.

The inventors have developed IP1 derivatives which make it possible to overcome the obstacles and disadvantages encountered during the use of the prior art methods for assaying IP1.

BRIEF DESCRIPTION OF DRAWINGS

FIGS. 1, 2, 3, 4, 5, 6, 7, 8, 9, and 10 depict reaction equations of methods of synthesis of various inositol analogs by structural formulae.

FIG. 12 is a graph showing the high specificity of the anti-IP1 antibody.

DESCRIPTION OF THE INVENTION

Figure 1:
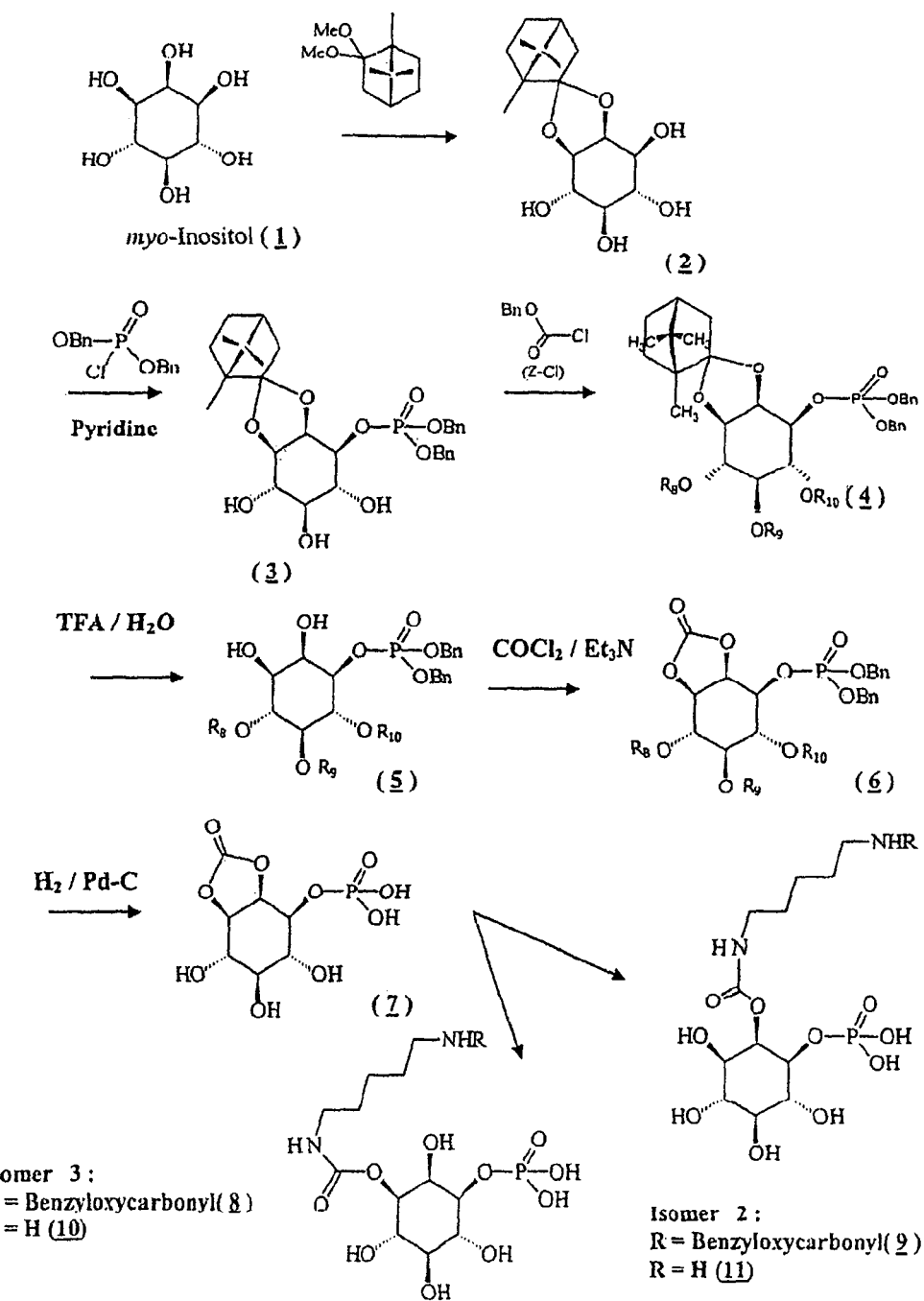

The invention provides functional analogs of IP1(1), IP1 (3), IP1(4) and IP1(5), substituted with a reactive group G or a conjugated substance or molecule M, said reactive group G or substance or molecule M being linked to IP1 via a linkage group L. The compounds according to the invention are functional analogs of IP1 insofar as they possess the same biological properties as the latter but have in addition the advantage of being able to be conjugated with a molecule or substance.

The invention provides in particular IP1 derivatives advantageously substituted on any one of the carbons of the inositol ring not bearing the phosphate group with one or two reactive groups G, or alternatively with one or two substances or molecules M, said reactive groups, substances or molecules being optionally linked to IP1 via a linkage group L.

The substance or molecule M, conjugated with an IP1 derivative of the invention substituted with a reactive group G, may be a marker which makes it possible to detect IP1 in a complex measuring medium. These markers may be, for example, radio isotopes, fluorescent or luminescent compounds or alternatively enzymes whose activity in the presence of their substrate can be easily measured. The substance or molecule M may also be a TAG which will, for example, be recognized by an antibody specifically directed against this TAG.

The derivatives according to the invention may moreover be linked to a solid support, this being covalently at the level of a carbon of the inositol ring not bearing the phosphate group.

The invention also provides immunogenic IP1 derivatives which make it possible to manufacture antibodies specific for IP1. These immunogens consist of the analogs according to the invention covalently linked, at the level of a carbon of the inositol ring not bearing the phosphate group, to a carrier molecule.

The invention additionally provides ligands which specifically recognize IP1, and in particular antibodies specific for IP1, termed anti-IP1 antibodies.

The invention moreover provides methods for detecting IP1, these methods using the IP1 analogs according to the invention or the ligands specific for IP1 according to the invention, and kits containing the components necessary for carrying out these methods.

Finally, the invention provides methods for the synthesis of IP1 analogs.

The IP1 analogs according to the invention have the general formula:

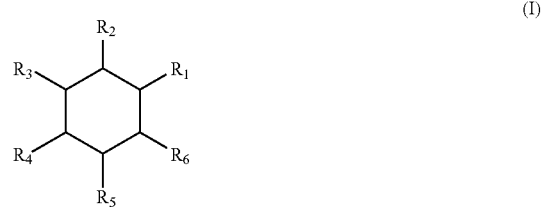

(I)

in which:

the substituents $R_1$, $R_2$, $R_3$, $R_4$, $R_5$, $R_6$ are chosen from: —OH, —OPO$_3^{2-}$, —OPO(OH)$_2$ or —OPO(OH)O$^-$, —(OCONH)$_q$-L-G or —(OCONH)$_q$-L-M, provided that one of the substituents $R_1$ to $R_6$ is a group —OPO$_3^{2-}$, —OPO(OH)$_2$ or —OPO(OH)O$^-$ and one or two of the other substituents $R_1$ to $R_6$ is one of the groups —(OCONH)$_q$-L-G or —(OCONH)$_q$-L-M, the other substituents $R_1$ to $R_6$ being the groups —OH;

where:

L is a linkage group,

G is a reactive group,

M is a conjugated substance or molecule chosen from the following group: a tracer, an immunogen, a member of the pair of binding partners, a solid support, q is equal to 0 or 1.

The preferred families of compounds according to the invention are myo-inositol derivatives of formula (II):

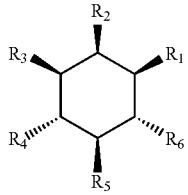

myo-inositol derivatives (II)

in which:
one of the substituents $R_1$, $R_3$, $R_4$ or $R_5$ is chosen from the groups —$OPO_3^{2-}$, —$OPO(OH)_2$ or —$OPO(OH)O^-$,
one or two of the other substituents $R_1$-$R_6$ is chosen from the groups —$(OCONH)_q$-L-G or —$(OCONH)_q$-L-M,
the other substituents are OH groups,
where:
Is L is a linkage group;
G is a reactive group;
M is a conjugated substance or molecule chosen from the following group: a tracer, an immunogen, a member of a pair of binding partners, a solid support;
q is equal to 0 or 1.

The invention also relates to chiro-, neo-, scyllo- and epi-inositol derivatives having the same stereochemistry as the myo-inositol derivatives except on the carbons bearing the substituents $(OCONH)_q$-L-G or —$(OCONH)_q$-L-M.

The chiro-inositol derivatives according to the invention contain a phosphate group at the 1, 4 or 5 position and are functionalized at the 3 position. These derivatives correspond to the formula (III):

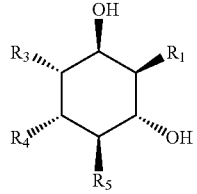

chiro-inositol derivatives (III)

in which:
one of the substituents $R_1$, $R_4$, $R_5$ is chosen from: —$OPO_3^{2-}$, —$OPO(OH)_2$ or —$OPO(OH)O^-$,
$R_3$ is chosen from: —$(OCONH)_q$-L-G or —$(OCONH)_q$-L-M,
the other substituents $R_1$, $R_4$ and $R_5$ are groups OH, —$(OCONH)_q$-L-G or —$(OCONH)_q$-L-M, at least one of them being an —OH group,
where:
L is a linkage group;
G is a reactive group;
M is a conjugated substance or molecule chosen from the following group: a tracer, an immunogen, a member of a pair of binding partners, a solid support;
q is equal to 0 or 1.

The neo-inositol derivatives according to the invention contain a phosphate group at the 1, 3 or 5 position and are functionalized at the 4 position. These derivatives correspond to the formula (IV):

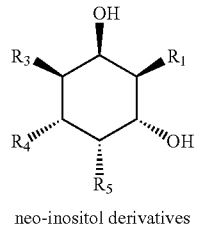

neo-inositol derivatives (IV)

in which:
one of the substituents $R_1$, $R_3$, $R_4$ is chosen from: —$OPO_3^{2-}$, —$OPO(OH)_2$ or —$OPO(OH)O^-$;
$R_5$ is chosen from: —$(OCONH)_q$-L-G or —$(OCONH)_q$-L-M,
the other two substituents $R_1$, $R_3$ and $R_4$ are OH, —$(OCONH)_q$-L-G or —$(OCONH)_q$-L-M groups, at least one of them being an OH group,
where:
L is a linkage group;
G is a reactive group;
M is a conjugated substance or molecule chosen from the following group: a tracer, an immunogen, a member of a pair of binding partners, a solid support;
q is equal to 0 or 1.

The scyllo-inositol derivatives according to the invention contain a phosphate group at the 1, 3, 4 or 5 position and are functionalized at the 2 position. These derivatives correspond to the formula (V):

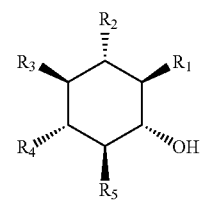

scyllo-inositol derivatives (V)

in which:
one of the substituents $R_1$, $R_3$, $R_4$, $R_5$ is chosen from: —$OPO_3^{2-}$—$OPO(OH)_2$ or —$OPO(OH)O^-$,
$R_2$ is chosen from: —$(OCONH)_q$-L-G or —$(OCONH)_q$-L-M,
the other substituents $R_1$, $R_3$, $R_4$ and $R_5$ are OH, —$(OCONH)_q$-L-G or —$(OCONH)_q$-L-M groups, at least one of them being an OH group,
where:
L is a linkage group;
G is a reactive group;
M is a conjugated substance or molecule chosen from the following group: a tracer, an immunogen, a member of a pair of binding partners, a solid support;
q is equal to 0 or 1.

Finally, the epi-inositol derivatives according to the invention contain a phosphate group at the 1, 3 or 5 position and are functionalized at the 4 position. These derivatives correspond to the formula (VI):

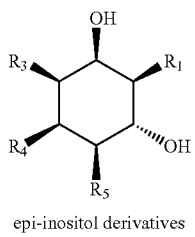

epi-inositol derivatives in which:
one of the substituents $R_1$, $R_3$, $R_5$ is chosen from: $OPO_3^{2-}$, —OPO(OH)$_2$ or —OPO(OH)O$^-$, $R_4$ is chosen from: —(OCONH)$_q$-L-G or —(OCONH)$_q$-L-M, the other substituents $R_1$, $R_3$ and $R_5$ are OH, —(OCONH)$_q$-L-G or —(OCONH)$_q$-L-M groups, at least one of them being an OH group, where:
L is a linkage group;
G is a reactive group;
M is a conjugated substance or molecule chosen from the following group: a tracer, an immunogen, a member of a pair of binding partners, a solid support;
q is equal to 0 or 1.

The compounds of formulae (I) to (VI) according to the invention in which one of the substituents is a phosphate group $OPO_3^{2-}$ or —OPO(OH)O$^-$ are optionally neutralized with any monovalent or divalent cation Z.

Examples of appropriate cations for the purposes of the invention are the cations Li$^+$, Na$^+$, K$^+$, (CH$_3$CH$_2$)$_3$NH$^+$, (C$_6$H$_{11}$)—NH$_3^+$, Ca$^{2+}$ and Ce$^{2+}$.

A family of preferred compounds according to the invention consists of the compounds of formulae (I) to (VI) in which $R_1$ is chosen from the groups —OPO$_3^{2-}$, —OPO(OH)$_2$ or —OPO(OH)O—.

Another family of preferred compounds according to the invention consists of the compounds of formulae (I) to (V) in which $R_4$ is chosen from the groups —OPO$_3^{2-}$, —OPO(OH)$_2$ or —OPO(OH)O$^-$.

Among the compounds of formulae (I) to (VI), there are most particularly preferred:

1) the compounds of formula (I) in which:
   $R_1$ is a group —OPO$_3$Z$_2$, —OPO(OH)$_2$ or —OPO(OH)OZ;
   $R_2$, $R_3$, $R_4$, $R_5$, $R_6$ are chosen from: —OH, —(OCONH)$_q$-L-G or —(OCONH)$_q$-L-M, four of the substituents $R_2$ to $R_6$ being OH groups;

2) the compounds of formula (II) in which:
   $R_1$ is a group —OPO$_3$Z$_2$, —OPO(OH)$_2$ or —OPO(OH)OZ;
   $R_2$, $R_3$, $R_4$, $R_5$, $R_6$ are chosen from: —OH, —(OCONH)$_q$-L-G or —(OCONH)$_q$-L-M, four of the substituents $R_2$ to $R_6$ being OH groups;

3) the compounds of formula (III) in which:
   $R_1$ is a group —OPO$_3$Z$_2$, —OPO(OH)$_2$ or —OPO(OH)OZ;
   $R_3$ is chosen from: —(OCONH)$_q$-L-G or —(OCONH)$_q$-L-M;

4) the compounds of formula (IV) in which:
   $R_1$ is a group —OPO$_3$Z$_2$, —OPO(OH)$_2$ or —OPO(OH)OZ;
   $R_5$ is chosen from: —(OCONH)$_q$-L-G or —(OCONH)$_q$-L-M;

5) the compounds of formula (V) in which:
   $R_1$ is a group —OPO$_3$Z$_2$, —OPO(OH)$_2$ or —OPO(OH)OZ;
   $R_2$ is chosen from: —(OCONH)$_q$-L-G or —(OCONH)$_q$-L-M;

6) the compounds of formula (VI) in which:
   $R_1$ is a group —OPO$_3$Z$_2$, —OPO(OH)$_2$ or —OPO(OH)OZ;
   $R_4$ is chosen from: —(OCONH)$_q$-L-G or —(OCONH)$_q$-L-M.

In each of the above definitions, L, M and q are as defined above for the compounds of formula (I) and Z is a cation chosen from Li$^+$, Na$^+$, K$^+$, (CH$_3$CH$_2$)$_3$NH$^+$, (C$_6$H$_{11}$)—NH$_3^+$.

The IP1 analogs containing a reactive group G may be linked to numerous organic or inorganic molecules which naturally contain, or into which have been introduced, functional groups capable of reacting with the reactive group G, thus allowing the covalent bonding of the substance or molecule M to IP1, optionally via the linkage group L.

1. Reactive Group G:

The expression reactive group G is understood to mean a group capable of reacting with a functional group present on another substance or molecule, to form a covalent bond. In the present case, the reactive group G will react with a functional group present on the molecule or substance which it is desired to conjugate with IP1.

Typically, the reactive group is an electrophilic or nucleophilic group which may form a covalent bond when it is brought into contact with an appropriate nucleophilic or electrophilic group, respectively. The conjugation reaction between the IP1 analog and the substance or molecule to be conjugated M causes the formation of a covalent bond comprising one or more atoms of the reactive group. By way of examples, the pairs of electrophilic/nucleophilic groups and the type of covalent bond formed when they are brought into contact are listed below:

| Electrophilic group | Nucleophilic group | Type of bond |
|---|---|---|
| acrylamides | thiols | thioethers |
| acyl halides | amines/anilines | carboxamides |
| aldehydes | amines/anilines | imines |
| aldehydes or ketones | hydrazines | hydrazones |
| aldehydes or ketones | hydroxylamines | oximes |
| alkyl sulfonates | thiols | thioethers |
| anhydrides | amines/anilines | carboxamides |
| aryl halide | thiols | thiophenols |
| aryl halide | amines | aryl amines |
| aziridines | thiols | thioethers |
| carbodiimides | carboxylic acids | N-acylureas or anhydrides |
| activated esters* | amines/anilines | carboxamides |
| haloacetamides | thiols | thioethers |
| halotriazines | amines/anilines | aminotriazines |
| imido esters | amines/anilines | amidines |
| isocyanates | amines/anilines | ureas |
| isothiocyanates | amines/anilines | thioureas |
| maleimides | thiols | thioethers |
| sulfonate esters | amines/anilines | alkyl amines |
| sulfonyl halides | amines/anilines | sulfonamides |

*the expression activated ester is understood to mean groups of formula COY, where Y is:
a leaving group chosen from succinimidyloxy (—C$_4$H$_4$NO$_2$), sulfo succinimidyloxy (—C$_4$H$_3$O$_2$—SO$_3$H) groups; an aryloxy group that is unsubstituted or substituted with at least one electron-attracting substituent such as nitro, fluoro, chloro, cyano and trifluoromethyl groups, thus forming an activated aryl ester;
a carboxylic acid activated with a carbodiimide group, thus forming a mixed anhydride —OCOR$_a$ or —OCNR$_a$NHR$_b$, in which R$_a$ and R$_b$ are identical or different and are chosen from C$_1$-C$_6$ alkyl, C$_1$-C$_6$ perfluoroalkyl, C$_1$-C$_6$ alkoxy and cyclohexyl groups, 3-dimethylaminopropyl, N-morpholinoethyl.

By way of nonlimiting example, the substance or molecule to be conjugated M comprises at least one of the following functional groups, with which the reactive group G will react:

amines, amides, thiols, aldehydes, ketones, hydrazines, hydroxylamines, secondary amines, halides, epoxides, carboxylate esters, carboxylic acids, double bonds, or a combination of these functional groups.

The functional group carried by the molecule M which will react with the reactive group G will be for example an amine, thiol, alcohol, aldehyde or ketone group. Preferably, the reactive group G will react with an amine or thiol functional group.

Methods for introducing these functional groups are in particular described in C. Kessler, Nonisotopic probing, Blotting and Sequencing, $2^{nd}$ edition, L. J. Kricka (1995), Ed. Academic press Ltd., London, p. 66-72.

Preferably, the reactive group G is a group derived from one of the compounds below: an acrylamide, an activated amine (for example a cadaverine or an ethylenediamine), an activated ester, an aldehyde, an alkyl halide, an anhydride, an aniline, an azide, an aziridine, a carboxylic acid, a diazoalkane, a haloacetamide, a halotriazine, such as monochlorotriazine, dichlorotriazine, a hydrazine (including hydrazides), an imido ester, an isocyanate, an isothiocyanate, a maleimide, a sulfonyl halide, or a thiol, a ketone, an amine, an acid halide, a hydroxysuccinimidyl ester, a hydroxysulfosuccinimidyl ester, an azidonitrophenyl, an azidophenyl, a 3-(2-pyridyldithio)-propionamide, glyoxal and in particular the groups of formula:

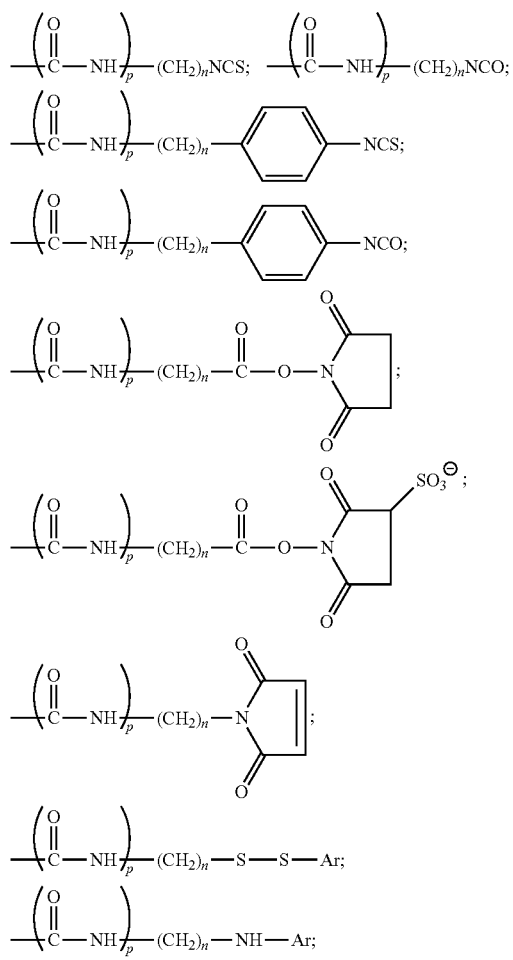

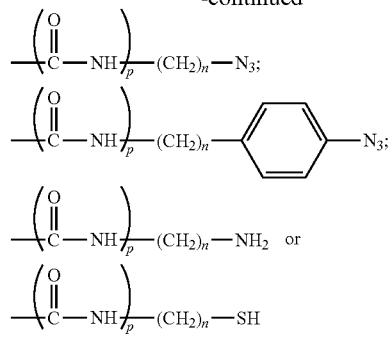

where n varies from 0 to 8 and p is equal to 0 or 1, and Ar is a 5- or 6-membered heterocycle comprising 1 to 3 heteroatoms, optionally substituted with a halogen atom.

Preferably, the reactive group G is a carboxylic acid, a carboxylic acid succinimidyl ester, a haloacetamide, a hydrazine, an isothiocyanate, a maleimide group, an aliphatic amine.

2. Linkage Group L:

The linkage group L which links the reactive group G or the conjugated substance or molecule M to IP1 may be a single covalent bond or a spacer arm comprising from 1 to 20 atoms different from hydrogen, chosen from carbon, nitrogen, phosphorus, oxygen and sulfur atoms, this linkage group being linear or branched, cyclic or heterocyclic, saturated or unsaturated, and consisting of a combination of bonds chosen from: carbon-carbon bonds which may be single, double, triple or aromatic; carbon-nitrogen bonds; nitrogen-nitrogen bonds; carbon-oxygen bonds; carbon-sulfur bonds; phosphorus-oxygen bonds; phosphorus-nitrogen bonds; ether bonds; ester bonds; thioether bonds; amine bonds; amide bonds; carboxamide bonds; sulfonamide bonds; urea bonds; urethane bonds; hydrazine bonds; carbamoyl bonds.

Preferably, the linkage group L comprises from 1 to 20 atoms different from hydrogen and chosen from C, N, O, P and S and may comprise combinations of ether, thioether, carboxamide, sulfonamide, hydrazine, amine and ester bonds and aromatic or heteroaromatic bonds.

Preferably, L consists of a combination of carbon-carbon single bonds and carboxamide or thioether bonds.

By way of example, L may be chosen from the following chains: polymethylene, arylene, alkylarylene, arylenealkyle, or arylthio.

According to an advantageous aspect, the linkage group L consists of a bivalent organic radical chosen from linear or branched $C_1$-$C_{20}$ alkylene groups optionally containing one or more double bonds or triple bonds and/or optionally containing one or more heteroatoms, such as oxygen, nitrogen, sulfur, phosphorus or one or more carbamoyl or carboxamido groups; $C_5$-$C_8$ cycloalkylene groups and $C_6$-$C_{14}$ arylene groups, said alkylene, cycloalkylene or arylene groups being optionally substituted with alkyl, aryl or sulfonate groups.

In particular, the linkage group L is chosen from the groups:

 1)

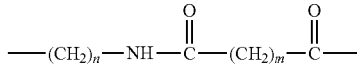 2)

-continued

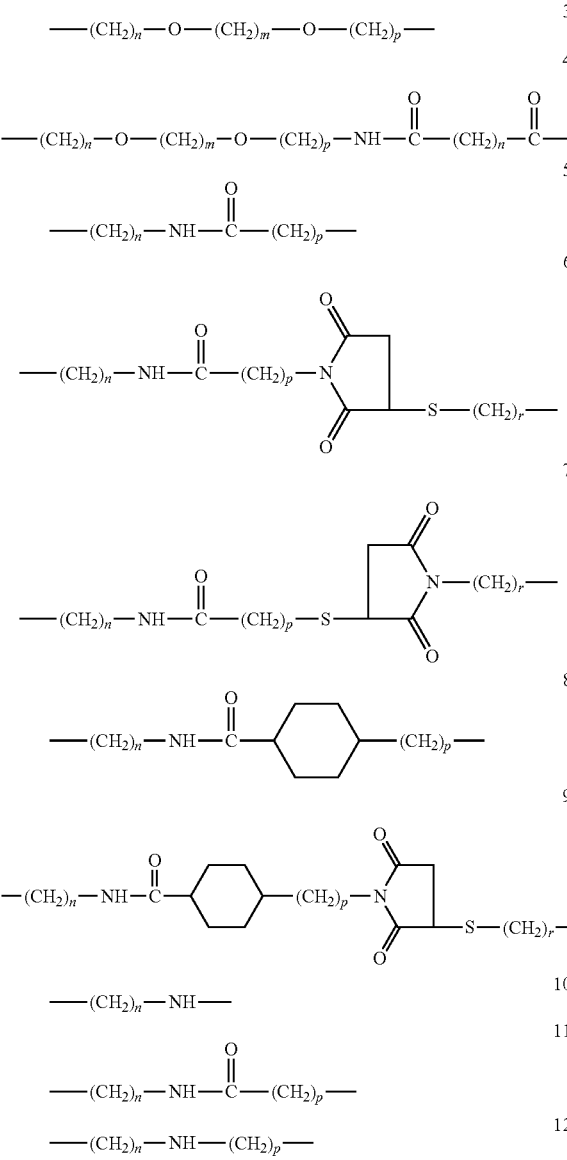

in which:

n and m are integers from 2 to 16, preferably from 2 to 8;
p and r are integers from 1 to 16, preferably from 1 to 5.

The linkage groups L 1) to 5), 7) and 10) to 12) are particularly appropriate when the functional group which makes it possible to connect the linkage group to the molecule that is an IP1 analog is a carbamoyl or ether group and the functional group on the substance or molecule M is an amide group.

The linkage groups L 6) and 9) are particularly appropriate when the functional group which makes it possible to connect the linkage group to the molecule that is an IP1 analog is a carbamoyl or ether group and the functional group on the substance or molecule M is an amide or thioether group.

3. Method of Synthesis:

The methods for synthesizing the analogs of the invention are represented in FIGS. 1 to 9 appended to the present description and explained below.

Method for the Synthesis of Myo-Inositol Analogs (Compound 1) Containing a Reactive Group G at the 2 or 3 Position (FIG. 1).

The present invention also relates to a method for synthesizing IP1 analogs from myo-inositol (compound 1) comprising the following steps:

(i) Protection of the Diol Functional Groups at the Cis Position with a Protecting Group:

The diol functional groups which are adjacent and in the cis configuration may be protected with an acetal derivative of an optically active ketone such as D-camphor dimethylacetal. As inositol carries 2 diols at the cis positions, the reaction of inositol with the protecting group will lead to the formation of two diastereoisomers which may be separated by conventional techniques known to persons skilled in the art.

(ii) Phosphorylation:

myo-Inositol whose cis diol functional groups are protected (compound 2) is then phosphorylated under the usual conditions known to persons skilled in the art. Preferably, dibenzyl phosphorochloridate is preferably used for this purpose under the conditions described in the examples below.

(iii) Protection of the Hydroxyl Functional Groups:

The hydroxyl functional groups of the inositol and those of the phosphate group may be protected by conventional protecting groups commonly used in the field of synthetic organic chemistry. To this effect, reference may be made to the book by Green [Protective Groups in Organic Synthesis, John Wiley & Sons, N.Y. (1981)].

Ester residues, such as pivaloyl, benzoyl, chloroacetyl, phenylacetyl, benzyloxycarbonyl, with silyl ether residues, such as trimethylsilyloxy, triethylsilyloxy, tert-butyldimethylsilyloxy, tert-butyldiphenylsilyloxy, benzyloxy, p-methoxybenzyloxy, 3,4-dimethoxybenzyloxy, allyloxy, allyloxycarboxy.

Preferably, the protecting group is a phenylmethyloxycarbonyl (=benzyloxycarbonyl) group.

(iv) Selective Deprotection of the Hydroxyl Functional Groups at the 2-3 Positions The hydroxyl functional groups at the 2-3 positions protected in step 1 are deprotected using conventional deprotection reagents known to persons skilled in the art. By way of example, in the case where the protecting reagent used is D-camphor dimethylacetal, the compound obtained in the preceding step may be reacted with a TFA/H$_2$O (trifluoroacetic acid) mixture.

This step makes it possible to obtain the intermediate of formula:

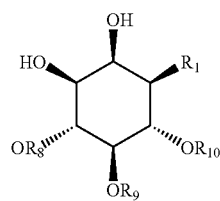

in which:

$R_1$ is a group —OPO(OR$_7$)$_2$;

$R_7$, $R_8$, $R_9$, $R_{10}$ are identical or different and represent a group for protecting the hydroxyl functional groups as defined above.

Preferably, $R_8$, $R_9$, $R_{10}$ are identical and represent the benzyloxycarbonyl group and $R_7$ is the benzyl (Bn) group or alternatively the two groups $R_7$ form together a xylylene group.

These intermediates may be advantageously used to produce the IP1 analogs of the invention.

(v) Formation of a Cyclic Carboxylate

In order to be able to graft the group L-G onto the compound obtained in the preceding step, the cyclic carboxylate functional group is introduced onto the carbons at the 2-3 positions of inositol. By way of example, this functional group may be generated by reacting the compound obtained in the preceding step with a phosgene, under the conditions described in the examples below.

The compound obtained has the formula:

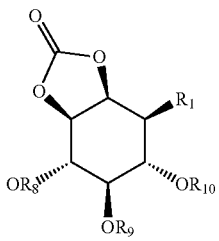

in which $R_1$ is a group —$OPO(OR_7)_2$;

$R_7$, $R_8$, $R_9$, $R_{10}$ are identical or different and represent a group for protecting the hydroxyl functional groups as defined above.

Preferably, $R_8$, $R_9$, $R_{10}$ are identical and represent a benzyloxycarbonyl group and $R_7$ is the benzyl (Bn) group or alternatively the two groups $R_7$ form together a xylylene group.

(vi) Deprotection of the Hydroxyl Functional Groups Protected in Step (iii)

This step is carried out according to conventional methods well known to persons skilled in the art and illustrated in the examples below.

(vii) Opening of the Cyclic Carboxylate and Introduction of the L-G Group

This step is carried out according to conventional methods well known to persons skilled in the art and illustrated in the examples below.

The main steps of this method are therefore:

(i) protection of the diol functional groups at the cis position with a protecting group;

(ii) phosphorylation;

(iii) protection of the hydroxyl functional groups;

(iv) deprotection of the hydroxyl functional groups at the 2-3 positions;

(v) formation of a cyclic carboxylate;

(vi) deprotection of the hydroxyl functional groups protected in step (iii);

(vii) opening of the cyclic carboxylate and introduction of the group L-G as defined above.

This general method is illustrated in Examples 1 to 10 below.

Method for Synthesizing Myo-Inositol-1-P Analogs Containing a Reactive Group G at the 4 and 5 Positions (FIG. 2):

This method is based on the use of synthesis intermediates of general formula:

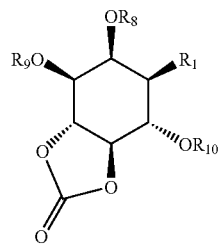

in which:

$R_1$ is a group —$OPO(OR_7)_2$;

$R_7$, $R_8$, $R_9$, $R_{10}$ are identical or different and represent a group for protecting the hydroxyl functional groups as defined above.

Preferably, $R_8$, $R_9$, $R_{10}$ are identical and represent the benzyloxycarbonyl group and $R_7$ is the benzyl (Bn) group or alternatively the two groups $R_7$ form together a xylylene group.

The derivative (compound 14) prepared according to a method described in the literature (Gigg, J. et al. Chem. Soc. Perkin trans I, 1987, 423) is treated with phosgene in pyridine to give the corresponding cyclic carbonate (compound 15). The phosphorylation of the cyclic 1,3,4-tri-O-benzyl-myo-inositol-4,5-O-carbonate may be carried out by treating with phosphorus oxychloride, with dibenzyl-phosphorochloridite or with di-O-benzyl-N,N-diisopropyl-phosphoramidite (in this case the phosphite intermediately obtained is oxidized to a phosphate with the aid of a peroxide, iodine or sodium periodate). Regardless of the method of phosphorylation used, the protected derivative of myo-inositol-1-phosphate (compound 16) thus obtained is subjected to catalytic hydrogenation (palladium on carbon) to give the myo-inositol-1-phosphate derivative (compound 17) possessing a cyclic carbonate at the 4,5 position which represents the key intermediate of this route of synthesis. 4-O-(5-Aminopentyl-carbamoyl)-D-myo-inositol-1-phosphate is obtained by opening the cyclic carbonate with the aid of a monobenzyloxycarbonyl derivative of a diamine, followed by catalytic hydrogenation; a mixture of the two regioisomers bearing the aminopentylcarbamoyl arm either at the 4-position (compound 18) or at the 5-position (compound 19) is obtained, these two isomers are then separated by reverse phase HPLC using an acetonitrile gradient in an aqueous triethylammonium acetate solution.

Method for Synthesizing Myo-Inositol-1-P Analogs Containing a Reactive Group G at the 4-Position (FIG. 3):

The 2,3:5,6-di-O-cyclohexylidene-myo-inositol derivative (compound 20) prepared according to a method described in the literature (Watanabe et al. Tetr. Lett. 1993, 34, 497) is treated with tribenzyl phosphate in the presence of pyridinium perbromide and triethylamine in a dichloromethane to predominantly give the 1-(dibenzyl phosphate) derivative (compound 21) according to the phosphorylation protocol described by Watanabe (see above); the desired compound is separated from the by-products such as the minor isomer phosphorylated at the C-4 position, by chromatography on silica. The phosphorylated derivative is then treated with carbonyldiimidazole in dimethylformamide, the intermediate imidazolyl derivative is not isolated and the product still in solution in DMF is treated with an excess (5 equivalents) of a mono-benzyloxycarbonyl derivative of a diamine. The inositol-1-phosphate analog bearing an aminopentylcarbamoyl chain at the 4-position thus obtained in a protected form (compound 23) R2=benzyloxycarbonyl) is successively treated in an acid medium in order to hydrolyze the cyclohexylidene protective groups and then subjected to catalytic hydrogenation to give the "deprotected" form (R2=H) of the desired inositol-1-phosphate analog bearing an aminopentylcarbamoyl chain at the 4-position (compound 24).

Figure 4:
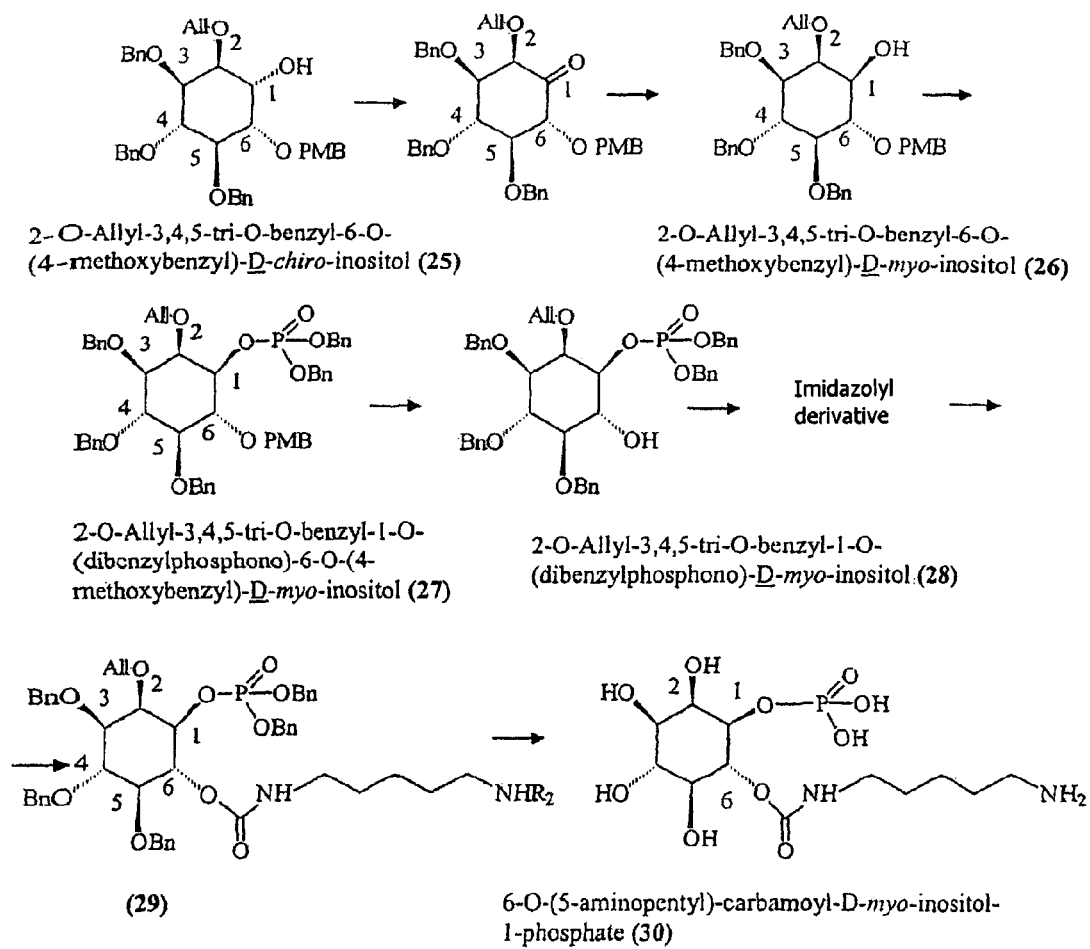

Method for the Synthesis of Chiro-Inositol-1-P Analogs Containing a Reactive Group G at the 6-Position (FIG. 4):

The 1-O-allyl-2,3,4-tri-O-benzyl-5-O-(p-methoxybenzyl)-D-chiro-inositol derivative (the product may also be named 2-O-allyl-3,4,5-tri-O-benzyl-6-O-(4-methoxybenzyl)-D-chiro-inositol (compound 25) in order to show its structural relationship with myo-inositol-1-phosphate; this numbering is used in FIG. 4 and the following description) prepared according to a method described in the literature (Jaramillo, C. et al J. Org. Chem. 1994, 59, 3135) is oxidized with pyridinium chlorochromate to give the corresponding ketone, which is purified by chromatography on silica gel. The ketone is stereoselectively reduced with a chiral hydride. The product of reduction is purified by chromatography on silica gel in order to separate the desired myo-inositol derivative from the by-product having a chiro configuration. The 2-O-allyl-3,4,5-tri-O-benzyl-6-O-(4-methoxybenzyl)-D-myo-inositol derivative (compound 26) thus obtained is phosphorylated with di-O-benzyl-N,N-diisopropylphosphoramidite in the presence of tetrazole; after oxidation with sodium periodate, the product is extracted and purified on silica gel. 2-O-Allyl-3,4,5-tri-O-benzyl-1-O-(dibenzylphosphono)-6-O-(p-methoxybenzyl)-D-myo-inositol (27) is thus obtained which is treated with 2% trifluoracetic acid in dichloromethane to give 2-O-allyl-3,4,5-tri-O-benzyl-1-O-(dibenzylphosphono)-D-myo-inositol (compound 28). This compound is then treated with carbonyldiimidazole in dimethylformamide, the intermediate imidazole derivative is not isolated and the product in solution in DMF is treated with an excess (5 equivalents) of a monobenzyloxycarbonyl derivative of a diamine. The inositol-1-phosphate analog bearing an aminopentylcarbamoyl chain at the 6-position thus obtained in a protected form ((compound 29), R2=benzyloxycarbonyl) is purified by chromatography on silica gel and then subjected to catalytic hydrogenation to give the "deprotected" form ((compound 30), R2=H) of the desired inositol-1-phosphate analog bearing an aminopentylcarbamoyl chain at the 6-position.

Figure 2:
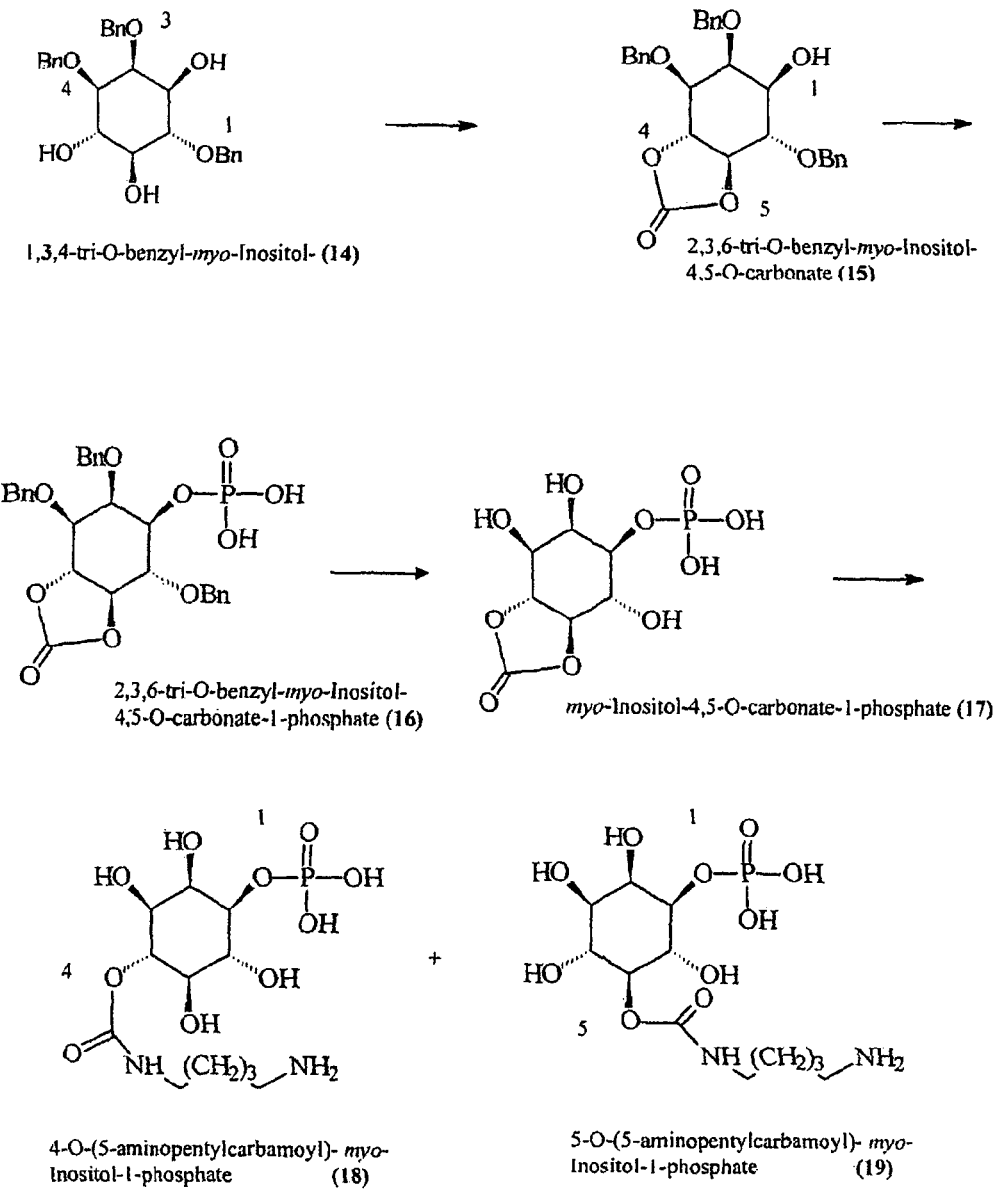
Figure 6:
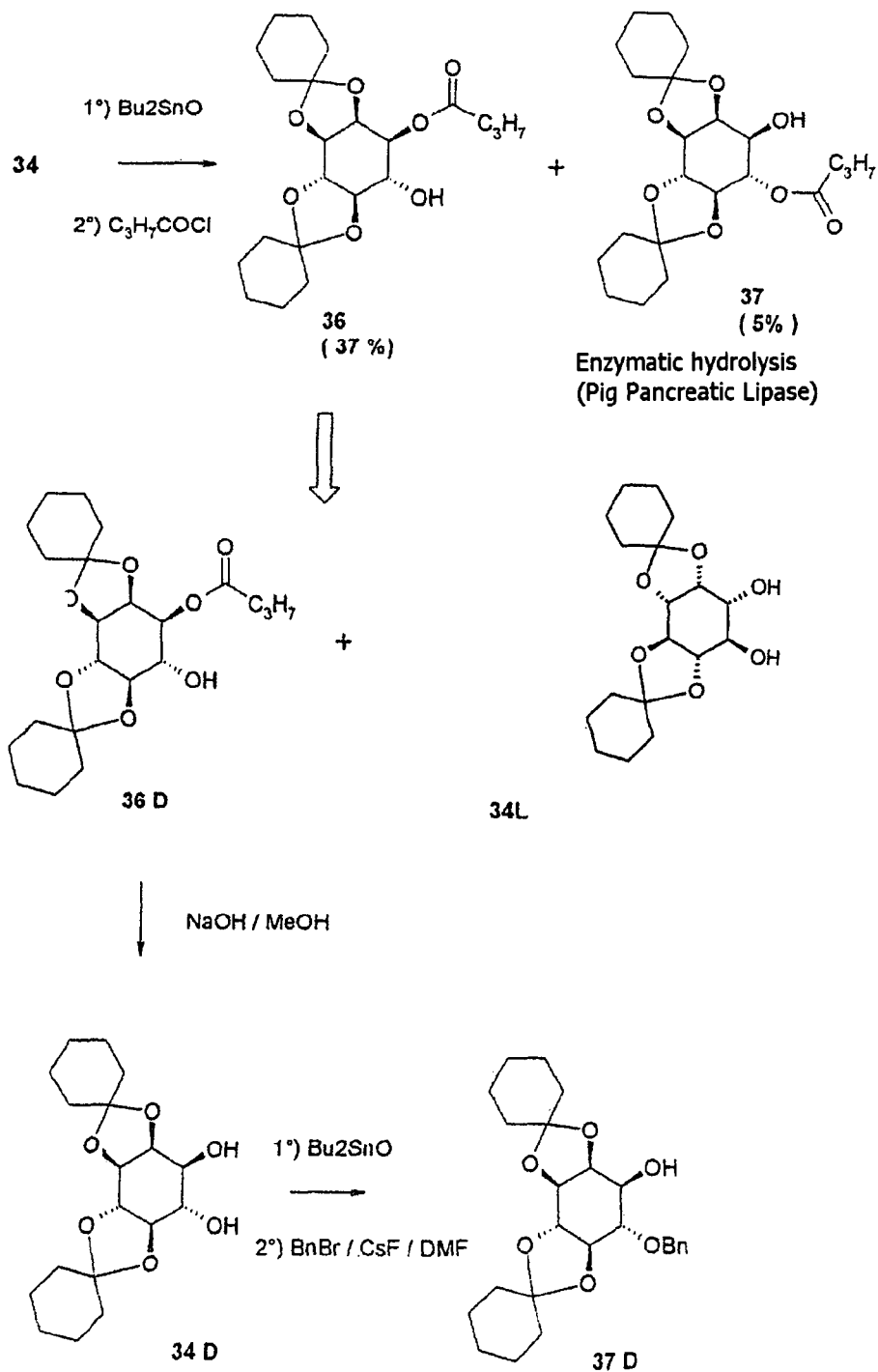
Figure 6:
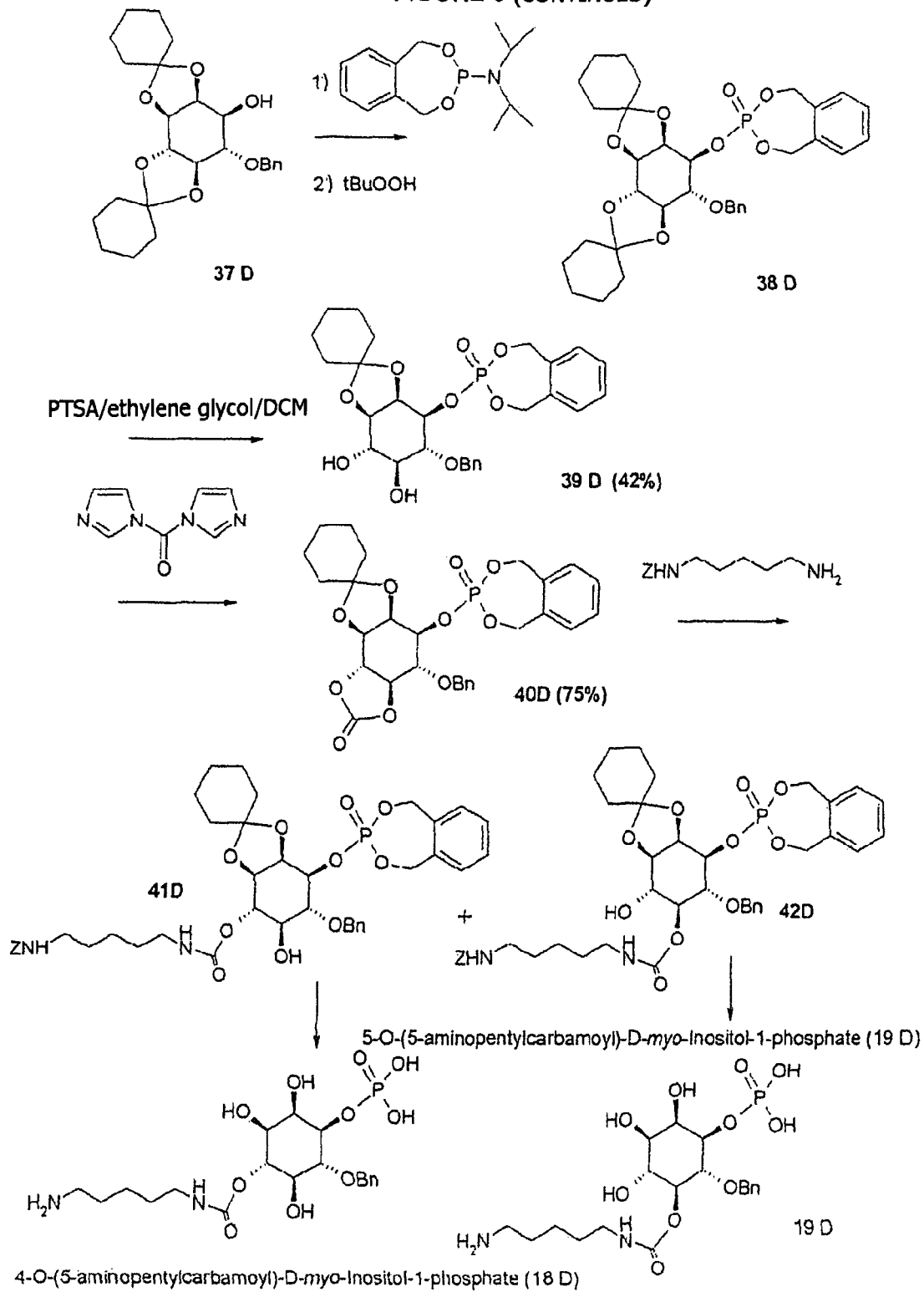
Figure 6:
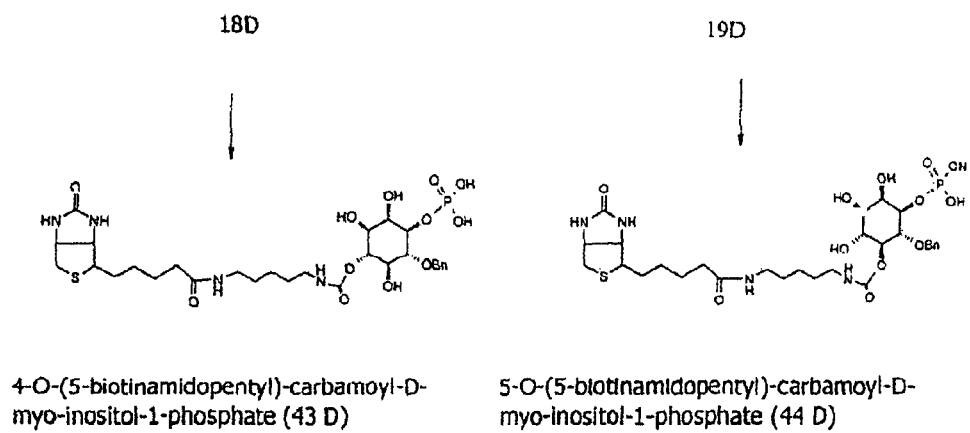

Method for the Synthesis of Myo-Inositol-1-P Analogs Containing a Reactive Group G at the 4- or 5-Position (FIG. 6):

D-myo-inositol-1-phosphate [IP1(1)] analogs containing the reactive group G at the 4- or 5-position (compounds 18 and 19 respectively) are described in the synthesis scheme (FIG. 2) and in the above text relating to FIG. 2, the route of synthesis starts with compound 14 prepared according to the method described in the literature from commercial myo-inositol (Gigg, J. et al. J. Chem. Soc. Perkin trans I, 1987, 423). It is possible to prepare the derivative 14 in an enantiomerically pure form in order to obtain the derivatives 18 and 19 in an enantiomerically pure form (18D and 19D) by introducing an optical resolution step. An alternative synthesis which makes is possible to more easily obtain these same compounds 18D and 19D in an enantiomerically pure form using an enzymatic resolution is proposed. The synthesis scheme is described in FIG. 6 starting with 2,3:4,5-di-O-cyclohexylidene-myo-inositol (compound 34), one of the isomers obtained during the protection of the commercial myo-inositol with two cyclohexylidene groups according to the protocol by Garegg et al. (Carbohydr. Chem. 130, 1984, 322-326). In FIG. 6, the enantiomer having the D configuration is arbitrarily used to designate the racemate and when only one of the enantiomers (for example the one having the D configuration) is designated, the compound number is followed by the letter D.

Thus, for example, 2,3:4,5-di-O-cyclohexylidene-myo-inositol (racemate) (compound 34) and the corresponding enantiomers L and D (compounds 34 L and 34 D) are represented as follows:

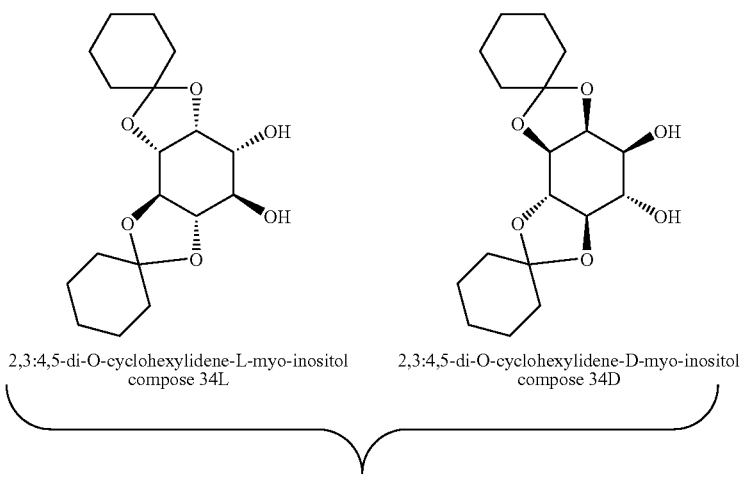

2,3:4,5-di-O-cyclohexylidene-L-myo-inositol
compose 34L 2,3:4,5-di-O-cyclohexylidene-D-myo-inositol
compose 34D

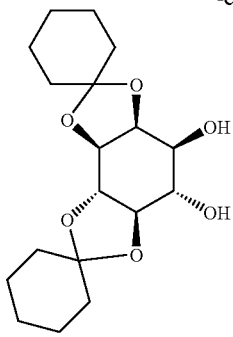

2,3:4,5-di-O-cyclohexylidene-myo-inositol (racemate)
compose 34

The 2,3:4,5-di-O-cyclohexylidene-myo-inositol derivative 34 in racemate form is treated with dibutyltin oxide and then with n-butyryl chloride as described by Gou et al. (*Carbohydr. Res.* 234, 1992, 51-64). Contrary to what is described in the article by Gou et al., the NMR data (the $H_1$ proton resonates at 4.98 ppm for compound 36 and at 3.89 for 37 and the H6 proton resonates at 4.09 ppm for compound 36 and at 5.21 ppm for compound 37) show that the predominant isomer is the derivative bearing the butyryl group at the 1-position (compound 36) and not the derivative bearing the butyryl group at the 6-position (compound 37) as described in the article by Gou et al. (*Carbohydr. Res.* 234, 1992, 51-64).

The monobutyric ester 36 (racemic) is subjected to an enzymatic resolution step according to the method described in the publication by Gou et al. (*Carbohydr. Res.* 234, 1992, 51-64), pancreatic lipase selectively hydrolyzes the L isomer to give 2,3:4,5-di-O-cyclohexylidene-L-myo-inositol (34L) leaving the 36D isomer (1-butyryl-2,3:4,5-di-O-cyclohexylidene-D-myo-inositol) unchanged, which makes it possible to obtain the 36D product in an enantiomerically pure form. The 36D product is saponified to give the 34D diol which is treated with dibutyltin oxide and then with benzyl bromide to give the monobenzylated 37D derivative; the latter is then treated with o-xylylene N,N-diisopropylphosphoramidite (prepared in a manner similar to o-xylylene N,N-diethylphosphoramidite (also called 1,5-dihydro-N,N-bis(1-methylethyl)-2,4,3-benzodioxaphosphepin-3-amine) according to the protocol by Watanabe et al. *Tetrahedron Letters*, 1990, 31, 255-256) and in the following documents: WO 9100258 A1 and *Tetrahedron Letters*, 1995, 36, 8023-8026) to give an unstable intermediate phosphate which is oxidized in situ with tert-butyl hydroperoxide, thus producing 6-O-benzyl-2,3:4,5-di-O-cyclohexylidene-5-O-(o-xylylenedioxyphosphoryl)-D-myo-inositol 38D. The cyclohexylidene protective group blocking the hydroxyls 4 and 5 of compound 38D is selectively removed by a treatment in an acid medium (transacetalation in the presence of ethylene glycol) to give the diol 39D which is then treated with 1,1'-carbonyldiimidazole to give the cyclic carbonate 40D. In a manner similar to what is described in Example 7, the cyclic carbonate of 40D is opened with a mono-protected derivative (protecting group Z=benzyloxycarbonyl) of pentylamine by generating the two position isomers: 41D (isomer bearing the arm at the 4-position) and 42D (isomer bearing the arm at the 5-position). Each of the isomers 41D and 42D is then deprotected to give respectively the compound 18D an analog of D-myo-inositol-1-phosphate bearing a reactive group at the 4-position of the inositol ring, and the compound 19D, an analog of D-myo-inositol-1-phosphate bearing a reactive group at the 5-position of the inositol ring. Example 19 describes the synthesis of the compounds 18D and 19D, which may be used in a manner similar to compounds 10 and 11 of Example 8 (note that the compounds 10 and 11 are enantiomerically pure because in the synthesis route described in FIG. 1, as the optical resolution occurs as early as the first step, all the derivatives starting from compound 2 are of the D series and are optically active). In a manner similar to that which is described in Example 9 for compound 10, compounds 18D and 19D may be conjugated with biotin by means of the reactive group which they carry respectively at the 4-position and at the 5-position of the myo-inositol-1-phosphate backbone; thus, compounds 18D and 19D are converted to their biotinylated conjugates 43D and 44D, respectively.

Figure 7:
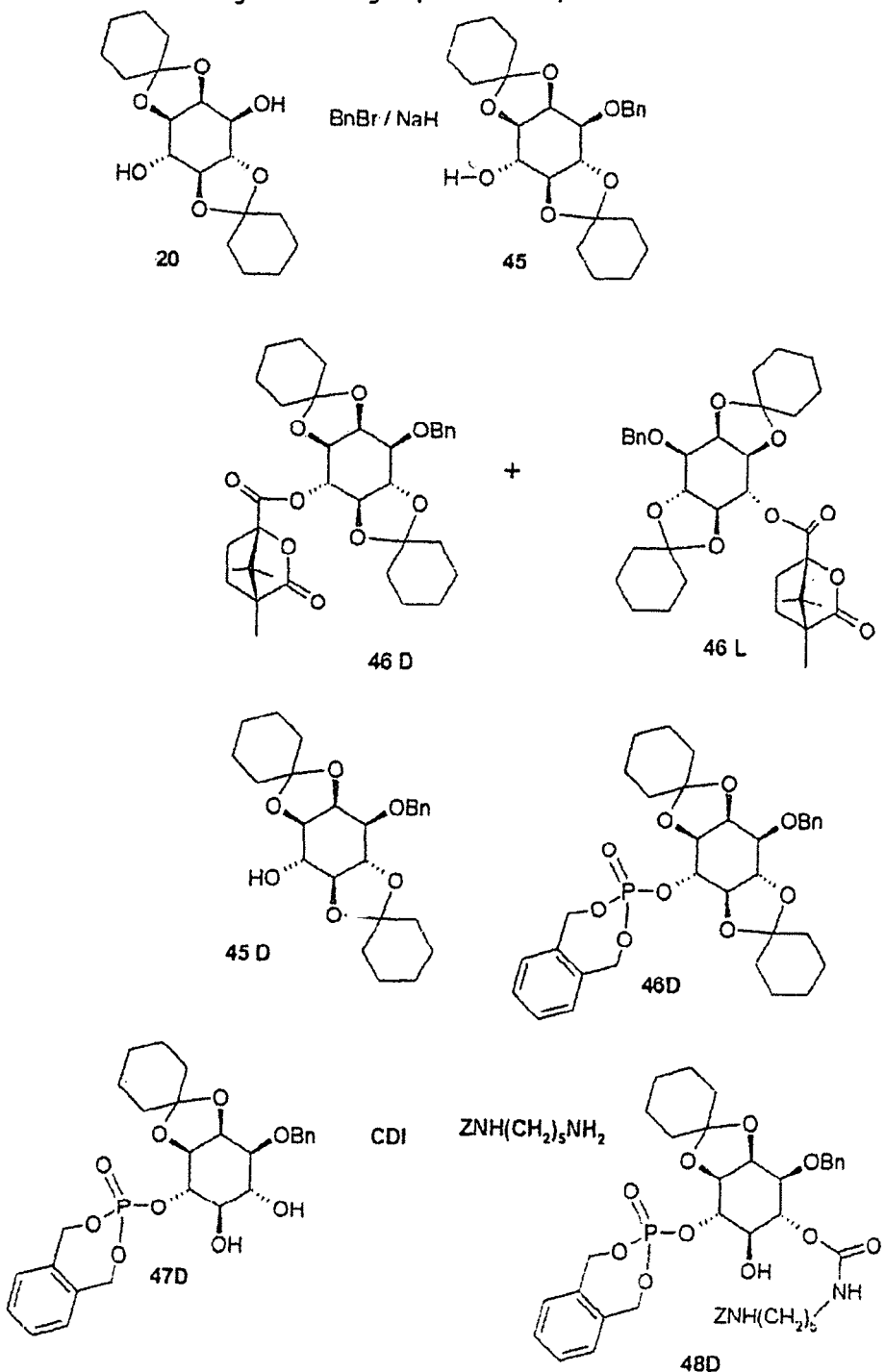
Figure 7:
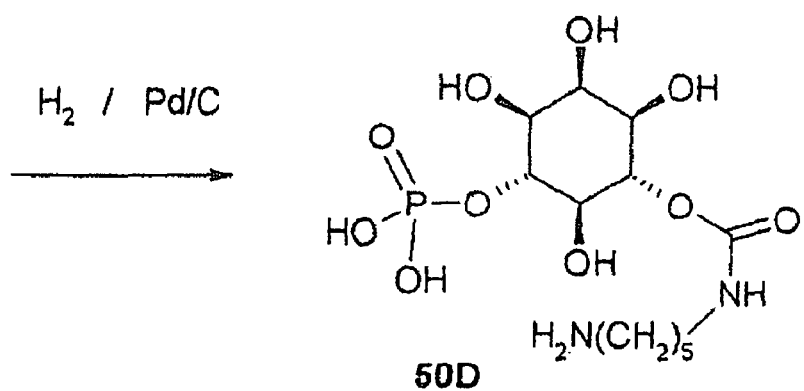
Figure 8:
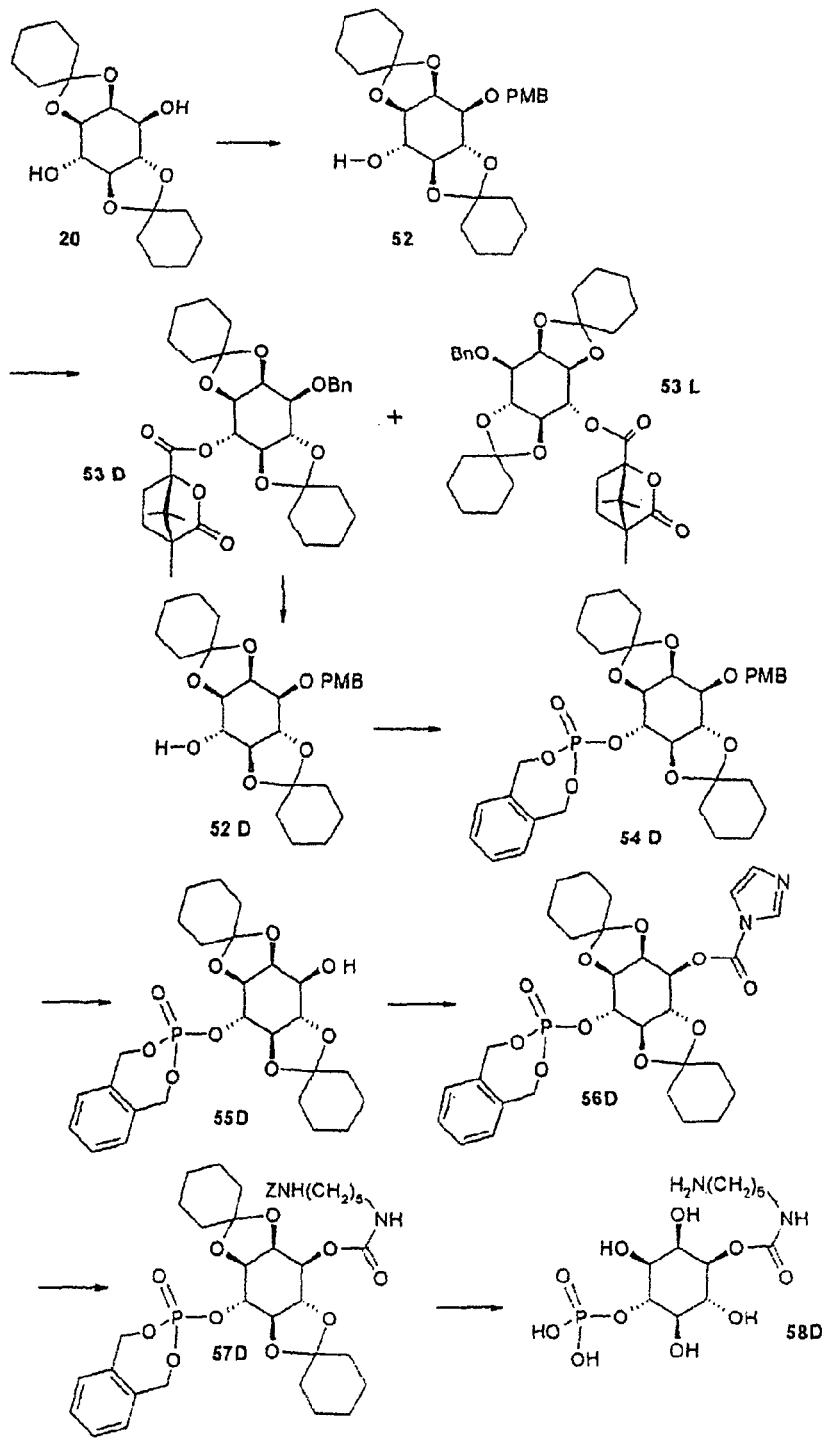
Figure 9:
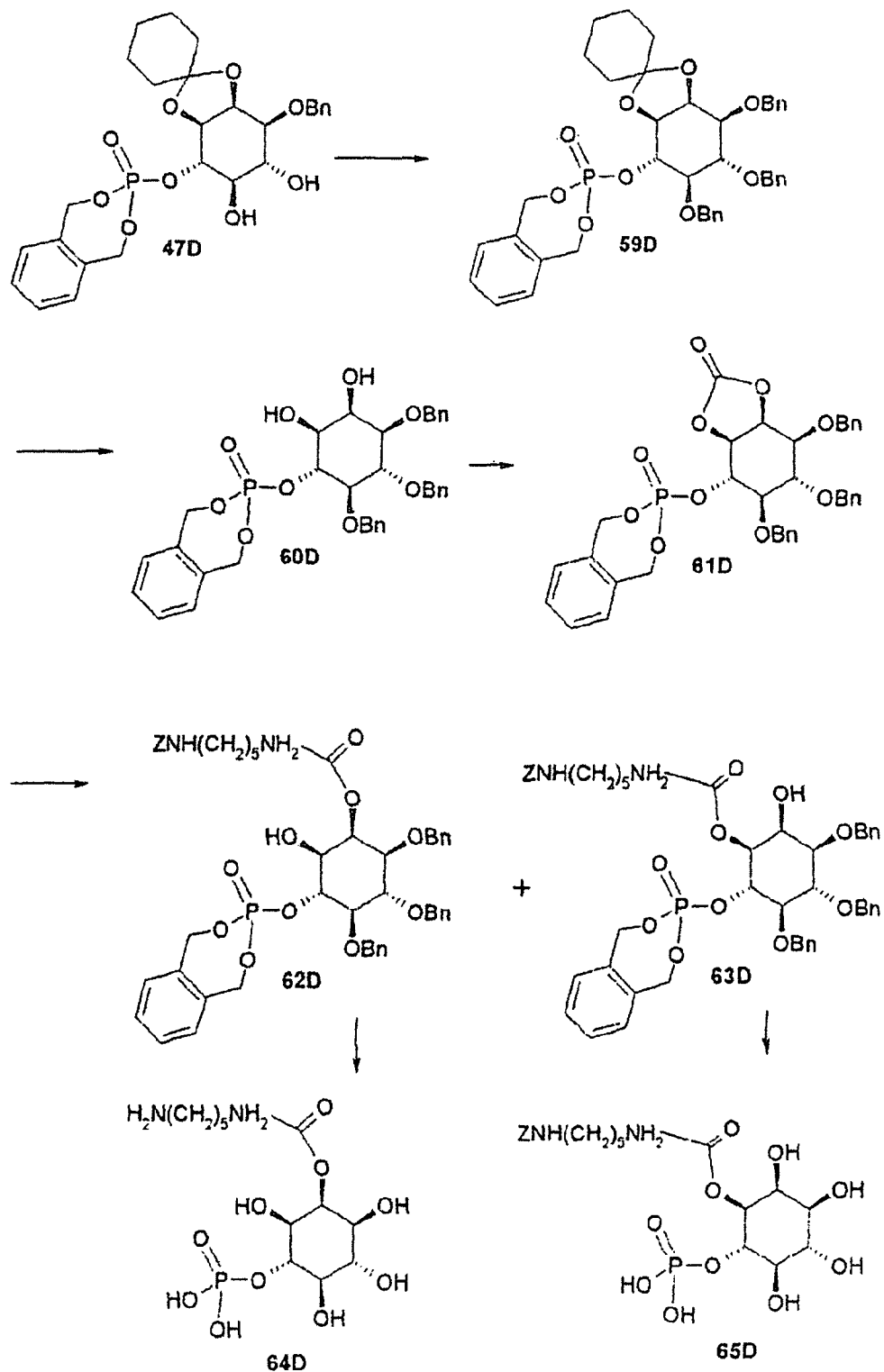

Method for the Synthesis of Myo-Inositol-4-Phosphate Analogs Containing a Reactive Group G at the 5 or 6 Position (see FIG. 7):

One of the inositol monophosphate forms, other than D-myo-inositol-1-phosphate and capable of accumulating during the activation of the inositol phosphate cycle, is D-myo-inositol-4-phosphate (see the article by Ragan et al. *Biochem J.* (1988) 249(1)143-148 relating to the formation of D-myo-inositol-4-phosphate and the article by Billington et al. *J. Chem. Soc. Perkin Trans.* 1, (1989) 8, 1423-1429 relating to a brief nomenclature of the various myo-inositol derivatives present in cells) it is therefore advantageous to have D-myo-inositol-4-phosphate analogs bearing a reactive arm at the 1, 2, 5 or 6 position. FIG. 7 shows a route for the synthesis of D-myo-inositol-4-phosphate bearing a reactive arm at the 6-position. 1,2:4,5-di-O-Cyclohexylidene-myo-inositol 20 (which may also be named 2,3:5,6-di-O-cyclohexylidene-myo-inositol in order to show its structural relationship with D-myo-inositol-4-phosphate, see FIG. 3) in racemic form, prepared according to the protocol by Vacca et al. is treated with benzyl bromide in order to obtain the monobenzylated derivative 45 as described by Vacca et al. [Vacca, J. P. *Tetrahedron*, 1989, 45(17), 5679-5702]. The derivative 45 (racemic) is treated with S(−)-camphanic acid chloride to give the mixture of two diastereomers (camphanate) 46D and 46L and the compound 46D (the most polar) is isolated by crystallization and recrystallization [Vacca, J. P. *Tetrahedron*, 1989, 45(17), 5679-5702]. The compound 46D is saponified with potassium hydroxide in ethanol to give the 4-hydroxyl derivative 45D which is phosphorylated with o-xylylene N,N-diisopropylphosphoramidite according to the protocol described for 37D (see FIG. 6 and Example 19) to give an intermediate phosphate which is oxidized in situ with tert-butyl hydroperoxide thus, giving 1-O-benzyl-2,3:5,6-di-O-cyclohexylidene-4-O-(o-xylylenedioxyphosphoryl)-

D-myo-inositol 46D. The compound 46D is treated according to the same protocol as the derivative 38D (see FIG. 6 and Example 19) in order to selectively remove the cyclohexylidene protective group blocking the hydroxyls 4 and 5, by a treatment in an acid medium to give the diol 47D.

Compound 47D is then treated successively with 1,1'-carbonyldiimidazole (CDI) and then with a monoprotected derivative (protecting group Z=benzyloxycarbonyl) of the pentylamine, generating the two position isomers: 48D (isomer bearing the arm at the 6-position) and 49D (isomer bearing the arm at the 5-position). Compounds 48D and 49D are separated by chromatography, and compounds 48D and 49D are independently deprotected by catalytic hydrogenation as described for compounds 41D and 42D (see FIG. 6 and Example 19), giving, respectively, compound 50D, an analog of D-myo-inositol-4-phosphate bearing a reactive group at the 6-position of the inositol ring, and compound 51D, an analog of D-myo-inositol-4-phosphate bearing a reactive group at the 5-position of the inositol ring (only compounds 48D and 50D having the arm at the 6-position are represented in FIG. 7).

Figure 3:
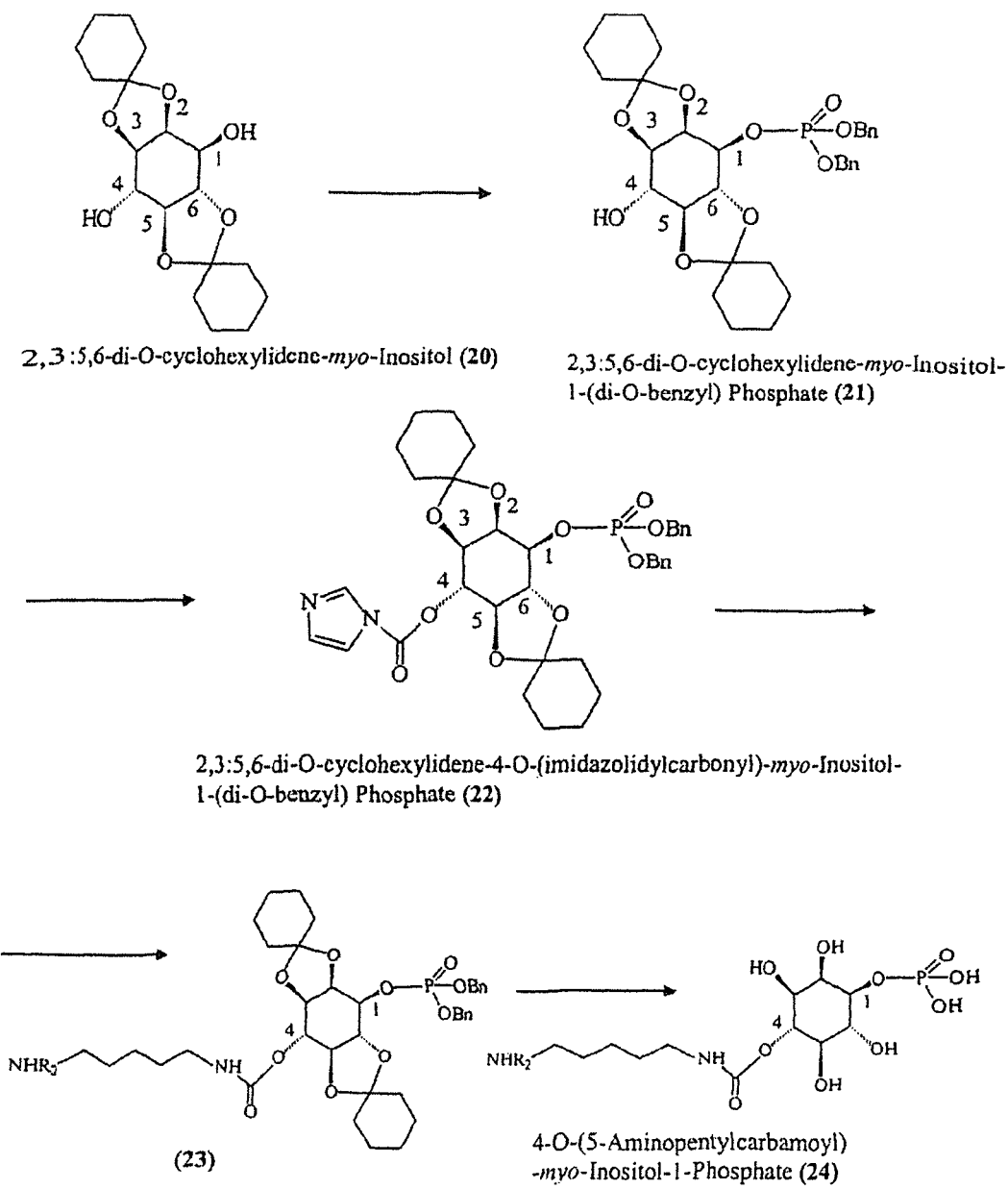

Method for the Synthesis of a Myo-Inositol-4-Phosphate Analog Containing a Reactive Group G at the 1-Position (see FIG. 8):

1,2:4,5-di-O-Cyclohexylidene-myo-inositol 20 (which may also be named 2,3:5,6-di-O-cyclohexylidene-myo-inositol to show its structural relationship with D-myo-inositol-4-phosphate, see FIG. 3) in racemic form, prepared according to the protocol by Vacca et al. [Vacca, J. P. *Tetrahedron*, 1989, 45(17), 5679-5702] is treated with 4-methoxybenzyl bromide according to a protocol described by Wang et al. [*J. Org. Chem.* 1996, 61, 5905-5910] in order to obtain the monoPMB derivative (protecting group PMB=p-methoxybenzyl=4-methoxybenzyl sometimes named MPM=p-methoxyphenylmethyl) 52. The derivative 52 (racemic) is treated with S(−)-camphanic acid chloride in order to give the mixture of the two diastereomer isomers (camphanate) 53D and 53L and the compound 53D is isolated by carrying out the procedure in a manner similar to what is described for compound 46D (see FIG. 7 and the corresponding text). In a similar manner, the enantiomerically pure compound 53D is saponified to give compound 52D. Compound 52D is phosphorylated with o-xylylene N,N-diisopropylphosphoramidite according to the protocol described for 37D (see FIG. 6 and Example 19) in order to give an intermediate phosphate which is oxidized in situ with tert-butyl hydroperoxide thus providing the derivative 2,3:5,6-di-O-cyclohexylidene-4-O-(o-xylylenedioxyphosphoryl)-D-myo-inositol 54D which is treated with CAN (Cerium Ammonium Nitrate) in an acetone-water mixture according to the protocol by Wright et al. [*Tetrahedron Lett.* 2001, 42, 4033] in order to remove the protecting group PMB and thus give the compound 55D possessing a free hydroxyl at the 1-position of the inositol ring. Compound 55D is then treated with 1,1'-carbonyldiimidazole (CDI) to give the imidazolide intermediate 56D which is then treated with a monoprotected derivative (protecting group Z=benzyloxycarbonyl) of the pentylamine to give the carmamate 57D bearing an arm at the 1-position of the inositol ring. Compound 57D is then deprotected by catalytic reduction in a manner similar to compounds 41D and 42D in order to give compound 58D, an analog of D-myo-inositol-4-phosphate bearing a reactive group at the 1-position of the inositol ring.

Method for the Synthesis of D-Myo-Inositol-4-Phosphate Analogs Containing a Reactive Group G at the 2 or 3 Position (see FIG. 9):

1-O-Benzyl-2,3-O-cyclohexylidene-4-O-(o-xylylenedioxyphosphoryl)-D-myo-inositol, compound 47D (see FIG. 7 and the corresponding text) is treated with benzyl bromide in order to protect the hydroxyls at the 5 and 6 positions in order to give compound 59D which is then treated in an acid medium to remove the 2,3-cyclohexylidene group, giving compound 60D. The latter is treated with phosgene (as in Example 5) or with 1,1'-carbonyldiimidazole (as in Example 19) to give a cyclic carbonate 61D which is then treated with a monoprotected derivative (protecting group Z=benzyloxycarbonyl) of the pentylamine, generating the two position isomers: 62D (isomer bearing the arm at the 2-position) and 63D (isomer bearing the arm at the 3-position). Compounds 62D and 63D are separated by chromatography, and compounds 62D and 63D are independently deprotected by catalytic hydrogenation as described for compounds 41D and 42D (see FIG. 6 and Example 19), giving, respectively, compound 64D, an analog of D-myo-inositol-4-phosphate bearing a reactive group at the 2-position of the inositol ring, and compound 65D, an analog of D-myo-inositol-4-phosphate bearing a reactive group at the 3-position of the inositol ring.

Figure 10:
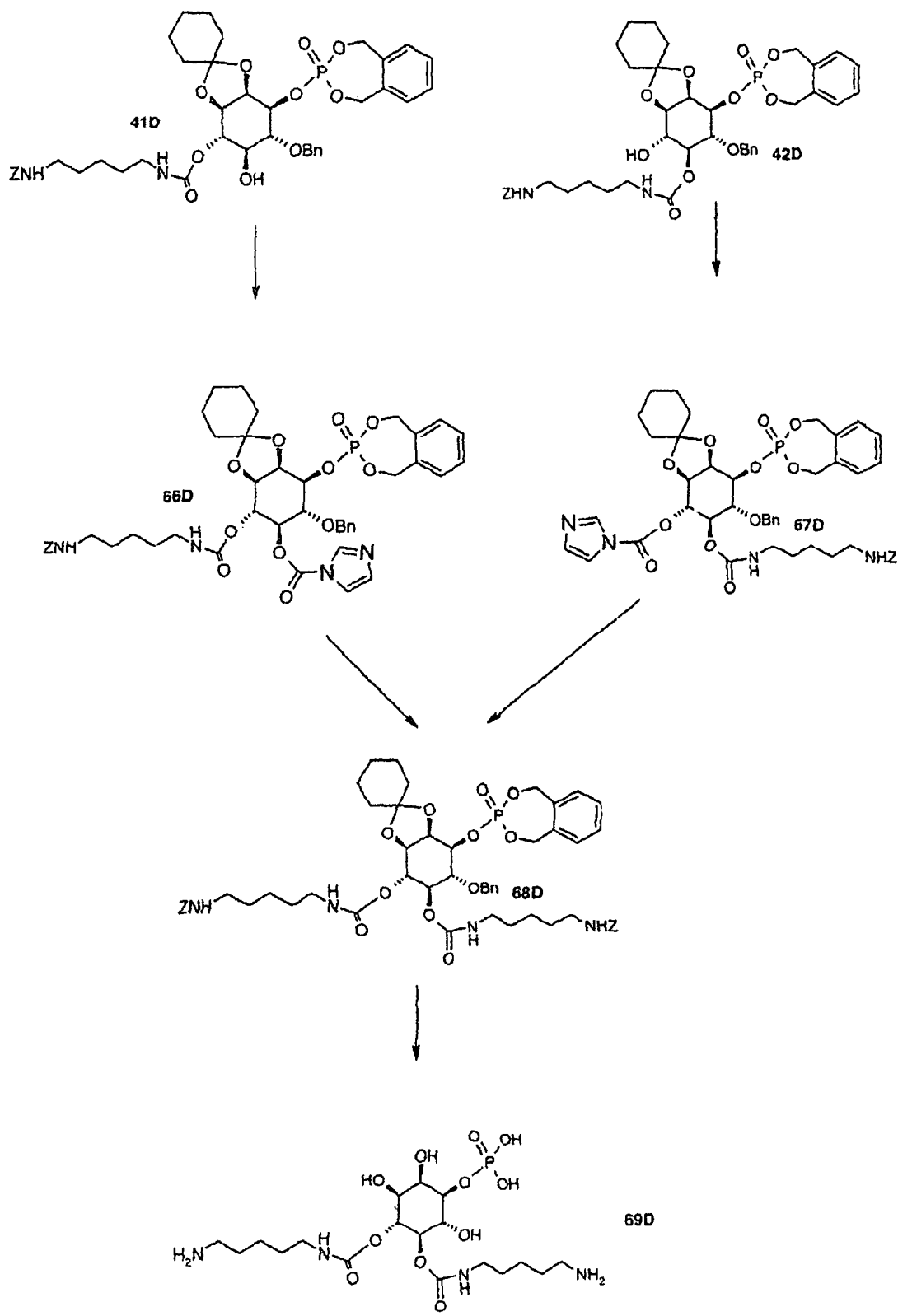

Method for the Synthesis of Myo-Inositol-1-P Analogs Containing Two Reactive Groups G at the 4 and 5 Positions (FIG. 10):

A D-myo-inositol-1-phosphate [IP1(1)] analog containing reactive groups G at the 4 and 5 positions (68D) is described in the synthesis scheme represented in FIG. 10. The general principle of the synthesis of these disubstituted analogs D-myo-inositol-1-phosphate is based on the routes for the synthesis of the monosubstituted analogs described above, using intermediates possessing a phosphate in its protected form (benzyl ester or o-xylyl ester) and possessing three protected hydroxyls and two free hydroxyls. The synthesis route described (FIG. 10) starts with compound 41D or with compound 42D or with a mixture of these two compounds prepared according to the method described in Example 19. Either the hydroxyl at the 5-position of compound 41D or the hydroxyl at the 4-position of compound 42D is activated by treating with carbonyldiimidazole (CDI), forming the corresponding imidazolyl derivative 66D and 67D, respectively. Each compound is then treated with a monoprotected derivative (protecting group Z=benzyloxycarbonyl) of the pentylamine (Example 7), generating the same compound 68D containing two arms at the 4 and 5 positions. Compound 68D is separated by chromatography and then deprotected by catalytic hydrogenation as described for compounds 41D or 42D (see FIG. 9 and Example 19), giving 4,5-di-O-(5-aminopentycarbamoyl)-D-myo-inositol-1-phosphate 69D, analog of D-myo-inositol-1-phosphate bearing two reactive groups at the 4 and 5 positions of the inositol ring. This analog may then be conjugated with a marker such as biotin as described in Example 9 or a fluorescent marker as described in Example 10.

4. Conjugates: Nature of M

The IP1 derivatives containing a reactive group G at one of the 2 to 6 positions of inositol may thus be coupled with a substance or molecule M.

Tracers

This substance or molecule M may be a tracer, and in this case the IP1 derivative obtained may be used to detect the IP1 present in a biological sample of interest.

The tracers commonly used for the study of biological or biochemical phenomena are fluorescent tracers, radioactive tracers, or alternatively molecules having themselves affinity or being recognized by a partner molecule. Certain enzymes, such as peroxidase or luciferase, which promote the appearance of a colored substrate or of a luminescence signal, respectively, may also be used.

The substance or molecule M may therefore be chosen from the following group: a radio element, a fluorescent compound, a luminescent compound, an enzyme, fluorescent chromophore, a light-absorbing chromophore, or any other molecule or substance allowing direct or indirect quantitative measurement, provided that when M is a radioelement, L is a single bond, then M is different from tritium.

The IP1 analogs according to the invention may thus be coupled to radioisotopes such as $^{125}$I, $^{32}$P, $^{35}$S or to a molecule labeled with one of the following isotopes: $^{125}$I, $^{32}$P, $^{35}$S or $^{3}$H.

The inventors indeed provide persons skilled in the art with IP1 analogs which may be easily coupled to radioisotopes or to labeled molecules using conventional radio labeling techniques.

Iodine-125 for example, which is highly electrophilic, will react with the analogs of the invention whose reactive group G contains nucleophilic groups, such as for example activated aryl groups. In particular, the analogs according to the invention whose reactive group G contains aromatic structures substituted with electron-donating substituents can allow labeling of IP1 by electrophilic substitution reactions on the aromatic nucleus. By way of example, phenols, aniline or alkylaniline derivatives containing primary or secondary amine or alcohol functional groups are capable of being labeled with iodine-125.

The analogs according to the invention may also be coupled to molecules which are themselves radiolabeled. In this indirect radiolabeling method, the substance or molecule to be conjugated M comprises the radioisotope and a functional group capable of reacting with the reactive group G of the IP1 analog according to the invention.

The IP1 analogs may also be coupled to fluorescent or luminescent molecules containing a functional group capable of reacting with the reactive group G carried by the IP1 analog. These fluorescent molecules are for example rhodamines, cyanines, squaraines, fluorophores known under the name BODIPY, fluoresceins, compounds known under the name AlexaFluor, rare-earth chelates, rare-earth cryptates, quantum dots, fluorescent proteins such as the green fluorescent protein (GFP) or its variants, fluorescent proteins extracted from corals, phycobiliproteins, such as B-phycoerythrin, R-phycoerythrin, C-phycocyanin, allophycocyanins, in particular those known under the name XL665. These compounds and the methods which make it possible to introduce reactive groups or functional groups therein are widely described in the literature, see, for example "Bioconjugate Techniques", Greg T. Hermanson, Academic press, 1996, p. 298-364.

The IP1 analogs may also be coupled to enzymes such as luciferase or peroxidase which generate a luminous or colored product, respectively, in the presence of their substrate.

The IP1 analogs according to the invention may also be coupled to a member of a pair of binding partners. Such binding partners may be the pairs avidin or streptavidin/biotin, haptene/antibodies such as for example 6HIS/anti-6HIS antibodies, FLAG/anti-FLAG antibodies, DNP/anti-DNP antibodies, GST/anti-GST antibodies, Cmyc/anti-Cmyc antibodies, HA/anti-HA antibodies, single-stranded oligonucleotide/complementary single-stranded oligonucleotide. In this case, the IP1 thus labeled may be indirectly detected via the addition of the second member of the binding partner pair, itself labeled with a tracer, which is for example radioactive or fluorescent.

Reagents which make it possible to label the analogs according to the invention with biotin groups are described in "Bioconjugate Techniques", Greg T. Hermanson, Academic press, 1996, p. 373-398.

Solid Support

The IP1 analogs according to the invention make it possible to couple IP1 to solid supports which are particularly useful for carrying out methods for detecting IP1 in a heterogeneous phase.

In this case, the group M may be a magnetic or nonmagnetic microbead, the well of a microplate, a tube, a fluorescent microbead, or any other solid phase system necessary for a detection system.

Immunogen

The IP1 analogs according to the invention also make it possible to prepare immunogenic conjugates which may be used to manufacture antibodies specific for IP1. For that, the analogs according to the invention are coupled to highly immunogenic carrier molecules. These molecules may be chosen from: bovine serum albumin (BSA) or cationic BSA (cBSA), KLH (Keyhole Limpet Hemocyanin) thyroglobulin, ovalbumin. The carrier molecules may also be liposomes or synthetic carrier molecules such as polymers of L-lysine, or of L-glutamic acid, ficoll, dextran, or alternatively polyethylene glycol.

These carrier molecules generally contain functional groups which will react with the reactive group G of the IP1 analogs according to the invention, or alternatively such groups may be introduced by conventional techniques.

It is important to note that the immunogenics according to the invention will make it possible to obtain antibodies specific for IP1 since the phosphate functional group of inositol, which is the only difference between IP1 and inositol, remains intact during the coupling with the carrier molecule.

5. Ligands Specific for IP1:

The IP1 analogs or the IP1 immunogens according to the invention may be used to select or produce ligands which specifically recognize IP1. These ligands, whose production is made possible by the provision of the IP1 derivatives according to the invention, therefore form an integral part of the invention.

These ligands may be in particular aptamers, peptides or proteins, in particular antibodies or antibody fragments (Fab or Fab'). The selection systems requiring the use of the IP1 analogs or the IP1 immunogens may in particular be selection systems using phages or ribosomes ("phage display" or "ribozomal display"). All these systems require the use of IP1 derivatives according to the invention.

The invention relates in particular to anti-IP1 monoclonal or polyclonal antibodies. The production of such antibodies is made possible by the IP1 analogs developed by the inventors. These antibodies specific for IP1 are a particularly useful tool for specifically detecting IP1. As the cellular medium generally contains numerous other inositol derivatives (PIP2, PIP3, IP3, IP2, IP4, inositol), the anti-IP1 antibodies must exhibit cross-reactions with these derivatives which are as weak as possible. The anti-IP1 antibodies according to the invention exhibit a cross-reaction with the inositol derivatives (PIP2, IP3, IP2, IP4, inositol) that is less than 5%. The anti-IP1 antibodies for which the cross-reaction of the antibodies with these inositol derivatives is less than 1% are particularly preferred.

Moreover, the anti-IP1 antibodies according to the invention exhibit a selectivity for attachment of IP1 which is at least 10 times higher than their attachment to the other inositol derivatives such as PIP2, PIP3, IP3, IP2, IP4, inositol. Antibodies having a selectivity for IP1 that is at least 100 times higher than is their selectivity for the other inositol derivatives are preferred. In other words, when the anti-IP1 antibodies according to the invention are incubated with IP1, their binding to IP1 remains stable when said derivatives are added to the incubation medium. This can be easily measured by determining, by conventional biochemical techniques, the quantity of IP1/anti-IP1 antibody complex in the presence or in the absence of one of the said derivatives. In particular, the binding of the anti-IP1 antibodies according to the invention to IP1 is not displaced in the presence of 50 μM of one of the following compounds: PIP2, PIP3, IP3, IP2, IP4, inositol.

The antibodies according to the invention are manufactured according to a method comprising a step of immunizing a mammal with an immunogenic conjugate according to the invention, as described above, which have the specific feature of presenting to the immune system a unique motif specific for IP1, namely an inositol substituted with a single phosphate group at the 1-position.

Anti-IP1 polyclonal antibodies are obtained by injecting immunogen into a mammal and, after a period necessary for the induction of immunity, the sera of the animals may be collected and the polyclonal antibodies purified, for example by affinity chromatography.

Anti-IP1 monoclonal antibodies may be produced using various techniques known to persons in the art. By way of example, there may be mentioned the technique obtained from the work by Köhler and Milstein. It consists in immunizing a mammal, for example mice, with an antigen. In the case where the antigen is of a small size, as is the case for IP1, it should be coupled to an immunogenic carrier molecule. Persons skilled in the art will therefore advantageously use the IP1-carrier molecule conjugates according to the invention. A few weeks after the immunization, the spleen of the mouse immunized with the antigen is removed. A mixture of lymphocytes and plasmocytes from this spleen is fused in vitro with myelomatous cells in the presence of an inducer of cell fusion, such as polyethylene glycol. A mutant myelomatous cell line, lacking hypoxanthine guanosin phosphoribosyl transferase (HGPRT), is used to allow easy selection of the hybrid cells. These cells are cultured in a medium containing hypoxanthine, aminopterin (methotrexate) and thymine (HAT medium) in order to eliminate the nonfused myelomatous cells and select the hybridomas of interest. The nonfused spleen cells die because they are not capable of proliferating in vitro. The hybrid cells, on the other hand, survive. The hybridomas thus obtained are cultured in the wells of a cell culture plate. The supernatants of these wells are tested for the presence of antibodies specific for IP1 in a screening test such as ELISA or RIA as described below. The hybridomas are then cloned and may be injected into mammals in order to induce myelomas secreting the anti-IP1 antibody in a large quantity in the ascitic fluid.

ELISA Test (Enzyme-Linked Immunoabsorbent Test) Allowing the Presence of Antibodies Specifically Recognizing IP1 to be Detected Indirect format after dilutions, the serum samples containing the anti-IP1 polyclonal antibodies (or the hybridoma culture supernatants in the case of anti-IP1 monoclonal antibodies) are incubated in wells of a microtiter plate coated with streptavidin and incubated beforehand with a solution of biotin-IP1 conjugate (obtained from an IP1 analog according to the invention) and then washed. After incubation in the presence of dilute sera, the wells are washed and incubated in the presence of peroxidase-labeled anti-species antibodies (Ac-HRP conjugate). After washing the conjugate Ac-HRP in excess, a revealing step is performed by adding the substrate. An optical density value at 450 nm indicating the presence of anti-IP1 antibodies in the sera or the culture supernatants is measured by photometric reading. The intensity of the OD measured at 450 nm is proportional to the quantity of anti-IP1 antibodies present in the well.

RIA Test (Radioimmunological Test) Allowing the Presence of Antibodies Specifically Recognizing IP1 to be Detected:

Semi-direct format after dilutions, the serum samples (or the hybridoma clone culture supernatants) are incubated in plastic tubes or wells of a microtiter plate coated with anti-species antibodies (for example anti-mouse antibodies if the anti-IP1 antibodies were made by immunization of mice) in the presence of a functionalized IP1 analog according to the invention labeled with a radioisotope (tracer). After incubation and washing, the radioactivity bound to the support is measured and shows that the radioisotope-labeled functionalized IP1 analog is recognized by anti-IP1 antibodies present in the sera or the culture supernatants.

6. Use of the Conjugates and Ligands Specific for IP1:

The various IP1 analogs and ligands specific for IP1 described above may be used in methods for detecting IP1 present in the biological sample. As indicated above, the assay of IP1 makes it possible to study the biochemical mechanisms involving the inositol phosphate signaling pathway. The tools provided by the inventors may be for example used in methods for screening compound libraries in order to identify molecules having an action on GPCR-type receptors, receptors having a tyrosine kinase activity, or for studying compounds having a regulatory (activating or inhibitory) activity on the enzymes responsible for the production of IP1 (phospholipase, inositol phosphatases). These methods always comprise a step for introducing the test molecule (obtained for example from a compound library) into the biological sample, followed by the detection of a qualitative or quantitative variation of the IP1 produced in said biological sample.

According to the invention, the method of detecting the IP1 contained in a sample comprises the following steps:
  bringing the sample into contact with a ligand specific for IP1;
  detecting the complexes formed between said ligand and the IP1 present in the sample.

The expression biological sample is understood to mean for example a membrane preparation, a cell suspension, a cell culture, or alternatively a preparation comprising GPCRs, G proteins and phospholipases.

The expression "detecting the complexes formed by the ligand specific for IP1 and the IP1 present in the sample" is understood to mean the direct detection of these complexes or alternatively indirect detection involving the detection of another species whose concentration is correlated with that of the ligand/IP1 complexes in the sample. The competition assay methods are a good example of indirect determination of the presence of IP1 in a sample. In these methods, there is competition between the IP1 present in the sample and the tritiated IP1 or the labeled IP1 for binding to the ligand specific for IP1. In these methods, the variation in the quantity of ligand/labeled IP1 complex introduced into the measuring medium is detected. The formation of a ligand/labeled IP1 complex will decrease when the quantity of ligand/IP1 complexes in the sample increases.

In a specific implementation of this method of detecting IP1, the ligand specific for IP1 is labeled with a tracer.

In another specific implementation, the method therefore comprises the addition, to the sample, of a known quantity of tritiated IP1 or of IP1 labeled directly or indirectly with a tracer. In other words, the method comprises the following steps:

bringing the sample into contact with a ligand specific for IP1;
bringing the sample into contact with a known quantity of tritiated IP1 or of IP1 labeled directly or indirectly with a tracer;
detecting the complexes formed between said ligand and the IP1 present in the sample.

The expression direct labeling is understood to mean covalent labeling optionally via a spacer arm such as the linkage group L described above.

The expression indirect labeling is understood to mean labeling via a pair of binding partners, as defined above. A ligand specific for IP1 or an IP1 analog may be indirectly labeled if they are bound to a member of a binding partner pair, and if the second member of this pair, labeled with a tracer, is added to the measuring medium. For example, IP1 may be bound to biotin and indirectly labeled with allophycocyanin (APC) if streptavidin coupled to APC is added to the medium, the streptavidin having a very high affinity for the biotin.

The tracer which may be conjugated with IP1 or with the ligand specific for IP1 may be chosen from: a radioelement, a fluorescent compound, a luminescent compound, an enzyme, a fluorescent chromophore, a light-absorbing chromophore, or any other molecule or substance allowing a direct or indirect quantitative measurement.

In another particular embodiment, the ligand specific for IP1 and the IP1 are both directly or indirectly labeled with tracers. That is for example the case in methods of detection based on an energy transfer between a donor fluorescent compound and an acceptor fluorescent compound (FRET).

In a particular implementation of this method, the ligand specific for IP1 is directly or indirectly conjugated with a donor compound, the sample is brought into contact with IP1 directly or indirectly conjugated with an acceptor compound, and the signal emitted by the acceptor compound is measured, this signal resulting from a proximity transfer between the donor and the acceptor and being inversely proportional to the quantity of IP1 present in the sample.

In another implementation, the ligand specific for IP1 is directly or indirectly conjugated with an acceptor compound, the sample is brought into contact with IP1 directly or indirectly conjugated with a donor compound, and the signal emitted by the acceptor compound is measured, this signal resulting from a proximity transfer between the donor and the acceptor and being inversely proportional to the quantity of IP1 present in the sample.

Preferably, the donor compound and the acceptor compound are fluorescent compounds, the proximity transfer is an energy transfer and the emitted signal is a fluorescent signal.

The fluorescent donor compound may be a rare-earth cryptate or chelate and the fluorescent acceptor compound may be chosen from: cyanines, rhodamines, squaraines, BODIPYs, fluoresceins, AlexaFluors, quantum dots, phycobiliproteins, such as B-phycoerythrin, R-phycoerythrin, C-phycocyanin, allophycocyanin, GFP and its derivatives, a coral fluorescent protein.

The ligands specific for IP1 used in the methods for detecting IP1 according to the invention are obtained using the IP1 derivatives as described above: these ligands specific for IP1 may be polyclonal or monoclonal antibodies produced by immunizing mammals with the IP1 derivatives according to the invention, or alternatively proteins, aptamers, or peptides specifically recognizing IP1, and selected by the "phage display" or "ribozomal display" techniques as mentioned above. Preferably, the ligand specific for IP1 used is a monoclonal or polyclonal antibody whose selectivity for IP1 is at least 10 times higher, preferably 100 times higher, than its selectivity for each of the following compounds: inositol, IP2, IP3, IP4, PIP2, PIP3.

In a particular embodiment of the method for detecting IP1 according to the invention, the ligand specific for IP1 or labeled IP1 is directly or indirectly linked to a solid support. That is for example the case when the SPA (scintillation proximity assay) technique is used: the ligand specific for IP1 will be covalently bound to SPA beads. That is also the case in the ELISA assay described in Example 17.

In the case where the IP1 analog is coupled to a solid support, it may be covalently linked, as described above. The IP1 analog may also be indirectly linked to the solid support: that is for example the case if the IP1 analog is IP1-biotin, and the solid support is coated with streptavidin. In this particular implementation of the method for assaying IP1, the ligand specific for IP1 is labeled with a tracer (radioactive, fluorescent or enzymatic tracer or the like) which will allow the detection of the IP1 analog/ligand specific for IP1 complex. If the ligand specific for IP1 is an anti-IP1 antibody, the latter may also be detected by adding to the sample an anti-species antibody labeled with a tracer.

A particular implementation of the method for detecting IP1 according to the invention therefore consists in bringing the sample into contact with an antibody specific for IP1 and an IP1 analog attached to a solid support, and additionally carrying out the following steps:

washing the solid support;
adding an anti-species antibody recognizing the anti-IP1 antibody, said anti-species antibody being labeled with a tracer;
detecting the anti-species antibody, the quantity of anti-species antibody being inversely proportional to the quantity of anti-IP1 antibody/IP1 complex present in the sample.

The ligand specific for IP1 may also be covalently bound to the solid support, or indirectly if the solid support is coated with an anti-species antibody, for example an anti-rat antibody if the ligand specific for IP1 is an anti-IP1 antibody obtained by immunizing rats. In this particular implementation, the IP1 analog will be labeled with a tracer (radioactive, fluorescent or enzymatic tracer) which will allow the detection of the IP1 analog/ligand specific for IP1 complex.

A variant of the method therefore consists in bringing the sample into contact with an antibody specific for IP1 attached to a solid support and with an IP1 analog labeled with a tracer, and then carrying out the following steps:

bringing the sample into contact with an anti-IP1 antibody attached to a solid support and with an IP1 analog labeled with a tracer, and additionally comprising the following steps:
washing the solid support;
detecting the labeled IP1;
the quantity of labeled IP1 being inversely proportional to the quantity of anti-IP1 antibody/IP1 complex present in the sample.

Other techniques known to persons skilled in the art may be used to carry out the methods for detecting IP1 according to the invention. There may be mentioned in particular polarization or alternatively fluorescence correlation spectroscopy techniques. In any case, these techniques are based on the formation of a ligand specific for IP1-IP1 complex, followed by a step for detection of the complexes formed.

The following examples of tests illustrate the method for assaying IP1 according to the invention:

ELISA Tests Using the IP1 Assay:

During the development of an ELISA assay, two assay formats may be envisaged:

- in a first format, a functionalized IP1 analog according to the invention is attached beforehand to a solid phase. The biological sample containing the IP1 to be assayed is then incubated in the presence of the complex formed on the solid phase with a first anti-IP1 antibody. After a washing step eliminating the species not attached to the solid phase, a second anti-species antibody labeled with an HRP-type enzyme, directed against the anti-IP1 antibody, is then added to the reaction well. After a washing step eliminating the excess of the unbound second antibody, a substrate of the HRP enzyme carried by the second antibody is added to the reaction well so as to generate the appearance of a colorimetry signal. The intensity of this signal, measured on a spectrophotometer, will be inversely proportional to the quantity of IP1 contained in the biological sample.
- in a second format, an anti-IP1 antibody will be attached beforehand to the solid phase. This attachment may be obtained in two ways: either by passive adsorption or using an immunologically reactive solid phase bearing a second anti-species antibody. The biological sample containing the IP1 to be assayed is then incubated in the presence of a functionalized IP1 analog, according to the invention. In this format, the use of an IP1 analog-biotin will be preferred. After a washing step eliminating the species not attached to the solid phase, streptavidin labeled with an HRP-type enzyme is then added to the reaction well. After a washing step eliminating the excess of unbound streptavidin, a substrate for the HRP enzyme carried by streptavidin is added to the reaction well so as to generate the appearance of a colorimetric signal. The intensity of this signal, measured on a spectrophotometer, will be inversely proportional to the quantity of IP1 contained in the biological sample.

HTRF Test (Homogeneous Time-Resolved Fluorometric Test) Detecting IP1 by Competition.

These tests may be carried out in various formats:

Direct format: samples containing the IP1 to be assayed are incubated in wells of a microtiter plate in the presence of an IP1-cyanin conjugate (or more generally of an IP1-FRET acceptor conjugate) and of an antibody anti-IP1 labeled with a europium cryptate conjugate (or more generally a lanthanide complex which can be used as FRET donor). The expression FRET acceptor is understood to mean any fluorescent molecule exhibiting spectral overlapping between its excitation spectrum and the emission spectrum of the lanthanide used as FRET donor.

A positive control containing only the IP1-cyanin conjugate and the anti-IP1-europium cryptate conjugate and a negative control containing only the anti-IP1-europium cryptate conjugate are also incubated in wells of a microtiter plate.

The fluorescence emitted at the wavelength of emission of the FRET acceptor (665 nm in the case of cyanin) and at the wavelength of emission of the FRET donor (620 nm in the case of the FRET acceptor) are time-resolved detected after excitation of the FRET donor (337 nm in the case of europium cryptate). The (fluorescence from the acceptor)/(fluorescence from the donor) ratio is then calculated for all the wells containing the samples to be assayed or the positive control or the negative control. The difference in ratio observed between the positive control and the negative control (reference DR) indicates the presence of a specific interaction between the anti-IP1 antibody and the IP1 analog. In the case where a sample contains IP1, it will enter into competition with the acceptor-IP1 analog in its binding to the antibody-europium cryptate conjugate. The DR value obtained in the presence of such a sample (sample DR) will be lower than that of the reference DR. The higher the difference between the reference DR and the sample DR, the higher the IP1 contained in the sample.

The same type of HTRF test may be performed using a donor-IP1 conjugate and an acceptor-antibody conjugate.

Semidirect format samples containing the IP1 to be assayed are incubated in wells of a microtiter plate in the presence of a conjugate IP1-biotin, streptavidin-XL665 (or more generally of an FRET acceptor conjugate) and of an antibody anti-IP1 labeled with a europium cryptate conjugate (or more generally a lanthanide complex which can be used as FRET donor).

The expression FRET acceptor is understood to mean any fluorescent molecule exhibiting spectral overlapping between its excitation spectrum and the emission spectrum of the lanthanide used as FRET donor.

A positive control containing only the conjugate IP1-biotin, streptavidin-XL665 and the conjugate anti-IP1-europium cryptate and a negative control containing only the conjugate anti-IP1-europium cryptate and streptavidin-XL665 are also incubated in wells of a microtiter plate.

The detection of the fluorescence emitted by the FRET donor and acceptor and the calculation of the results are identical to what was described above for a direct format.

"XL665" denotes a cross-linked allophycocyanin marketed by Cis Bio International.

Indirect format: samples containing the IP1 to be assayed are incubated in wells of a microtiter plate in the presence of a conjugate IP1-biotin, streptavidin-XL665 (or more generally of an FRET acceptor conjugate) and of an anti-IP1 antibody and an anti-species antibody recognizing the anti-IP1 antibody and labeled with a europium cryptate (or more generally a lanthanide complex which can be used as FRET donor).

The expression FRET acceptor is understood to mean any fluorescent molecule having spectral overlapping between its excitation spectrum and the emission spectrum of the lanthanide used as FRET donor.

A positive control containing only the conjugate IP1-biotin, streptavidin-XL665, the anti-IP1 antibody and the conjugate anti-species-europium cryptate and a negative control containing only the anti-IP1 antibody, the conjugate anti-species-europium cryptate and streptavidin-XL665 are also incubated in wells of a microtiter plate.

The detection of the fluorescence emitted by the FRET donor and acceptor and the calculation of the results are identical to what has been described above for the direct format.

These direct, semidirect or indirect HTRF tests are particularly suitable for the screening of chemical compound libraries for which it is desired to test for example the agonist, antagonist or inverse agonist effect on a given membrane receptor whose activation causes a rise in the intracellular IP1 level. These tests may be performed on cells using the IP1 analogs and the anti-IP1 antibodies according to the invention.

The invention therefore provides a method for screening compounds which are agonists for a membrane receptor whose activation causes the production of IP1 in the cell, this method comprising the following steps:

(i) addition of the test compound to the culture medium comprising cells expressing a receptor whose activation causes the production of IP1, (ii) determination of the quantity of IP1 using the methods according to the invention, (iii) comparison of the quantity of IP1 determined in the presence and in the absence of this compound, an increase in the quantity of IP1 which makes it possible to identify the test compound as an agonist of said receptor.

In a preferred implementation of this method, step (ii) comprises the addition, to the medium, of an anti-IP1 antibody labeled with a donor or acceptor fluorescent compound and the addition of IP1 labeled with an acceptor or, respectively donor, fluorescent compound, and the determination of the quantity of IP1 consists in measuring the light signal resulting from the energy transfer between the two fluorescent compounds, and step (iii) comprises the comparison of the signal measured in the presence and in the absence of the test compound, a reduction in the signal measured in the presence of a test compound making it possible to identify this compound as an agonist of said receptor.

The invention also provides a method of screening compounds that are antagonists of a membrane receptor whose activation causes the production of IP1 in the cell, this method comprising the following steps:

(i) addition of the test compound to a culture medium comprising cells expressing a receptor whose activation causes the production of IP1, (ii) addition of a known agonist of said receptor, (iii) determination of the quantity of IP1 using the methods according to the invention, (vi) comparison of the quantity of IP1 determined in the presence and in the absence of the test compound, a reduction in the quantity of IP1 making it possible to identify the test compound as an antagonist of said receptor.

Step (iii) comprises the addition, to the medium, of an anti-IP1 antibody labeled with a donor or acceptor fluorescent compound and the addition of IP1 labeled with an acceptor or, respectively donor, fluorescent compound, and the determination of the quantity of IP1 consists in measuring the light signal resulting from the energy transfer between the two fluorescent compounds, and step (iv) comprises the comparison of the signal measured in the presence and in the absence of a test compound, an increase in the signal measured in the presence of a test compound making it possible to identify this compound as an antagonist of said receptor.

The invention also provides a method for screening compounds that are inverse agonists of a constitutively active membrane receptor. A receptor is considered as being constitutively active when it possesses an intrinsic and basal G protein coupling activity and/or associated with a production of second messengers in the absence of stimulation by its agonist. In this case, an inverse agonist will have the effect of decreasing the magnitude of this basal response, in other words, of reducing or abolishing the permanent production of IP1 by this receptor in the absence of stimulation by its agonist.

A method of screening compounds causing a reduction in this constitutive activity can make it possible to identify novel medicaments.

The method of screening compounds that are inverse agonists of a constitutively active membrane receptor comprises the following steps:

(i) addition of the test compound to a culture medium comprising cells expressing a constitutively active receptor, and whose activity causes the production of IP1, (ii) determination of the quantity of IP1 using the methods according to the invention, (iii) comparison of the quantity of IP1 determined in the presence and in the absence of the test compound, a reduction in the quantity of IP1 making it possible to identify the test compound as an inverse agonist of said receptor.

In a preferred implementation of this method, step (ii) comprises the addition, to the medium, of an anti-IP1 antibody labeled with a donor or acceptor fluorescent compound and the addition of IP1 labeled with an acceptor or, respectively donor, fluorescent compound, and the determination of the quantity of IP1 consists in measuring the light signal resulting from the energy transfer between the two fluorescent compounds, and step (iii) comprises the comparison of the signal measured in the presence and absence of the test compound, an increase in the signal measured in the presence of a test compound making it possible to identify this compound as an inverse agonist of said receptor.

Persons skilled in the art are capable of adapting these methods so as to demonstrate other types of regulators of the activity of transmembrane receptors, such as for example positive allosteric modulators which potentiate the agonist effects.

7. Kits

The invention also relates to kits which make it possible to carry out these IP1 assay techniques. These kits comprise (i) an IP1 analog according to the invention or tritiated IP1, and (ii) a ligand specific for IP1, at least one of these components being labeled directly or indirectly with a tracer such as a radioelement, a fluorescent compound, a luminescent compound, an enzyme, a fluorescent chromophore, a light-absorbing chromophore, or any other molecule or substance allowing direct or indirect quantitative measurement.

The kits according to the invention may contain a donor compound and an acceptor compound emitting a signal resulting from a proximity transfer with the donor compound, the donor compound being directly or indirectly linked to the IP1 analog, and the acceptor compound being directly or indirectly linked to the ligand specific for IP1. In another embodiment of these kits, the acceptor compound is directly or indirectly linked to the IP1 analog, and the donor compound is directly or indirectly linked to the ligand specific for IP1. Advantageously, the donor compound and the acceptor compound are fluorescent compounds, the proximity transfer is an energy transfer and the emitted signal is a fluorescent signal.

A donor fluorescent compound is a fluorescent compound which, after excitation at a determined wavelength, will emit a fluorescent signal which, by performing an energy transfer, will excite the acceptor fluorescent compound. Numerous donor fluorescent compounds may be used in the context of the present invention. By way of example, there may be mentioned the rare-earth (europium, terbium) cryptates described in patents EP 180 492, EP 321 353, EP 601 113, and rare-earth chelates.

An acceptor fluorescent compound is a fluorescent compound which, after excitation by energy transfer from the donor compound, will emit a fluorescent signal at a given wavelength. Numerous acceptor compounds exist which are capable of being used to carry out the methods according to the invention, among which are: allophycocyanins, cross-linked allophycocyanin such as XL665 (CIS bio international), cyanines such as CY5, rhodamines, squaraines, BODIPYs, fluoresceins, AlexaFluors.

Preferably, the ligand specific for IP1 contained in these kits is an anti-IP1 polyclonal or monoclonal antibody obtained by immunizing a mammal with an IP1-carrier molecule conjugate.

The kits according to the invention may also contain lithium chloride or any other product which makes it possible to block certain enzymes of the inositol cycle and thus promotes the accumulation of IP1 in the sample.

According to the type of assay technique used, these kits will contain additional conventional components, namely solid supports, anti-species antibodies or any other component known and widely used in this type of product.

The following examples illustrate a route for the synthesis of the compounds according to the invention and their use.

Example 1

Synthesis of 2,3-O-[(1R,4R)-1,7,7-trimethylbicyclo[2.2.1]-hept-2-ylidene]-D-myo-inositol (inositol-camphor) (Compound 2)

Commercial myo-inositol (compound 1) (4.2 g) is suspended in anhydrous DMSO (50 ml) with D-camphor dimethylacetal (9.3 g). The mixture is stirred at 50° C. for 3 h, neutralized with triethylamine and concentrated under vacuum. The residue is taken up in a solution containing 18 mg of para-toluenesulfonic acid hydrate in a mixture of methanol and chloroform. After stirring overnight at 20° C., triethylamine is added and the precipitate obtained is filtered, washed with chloroform and then suspended in water, stirred for 15 min, and then filtered. The precipitate is washed with water and chloroform and then dried.

Yield 4.8 g (65%).
TLC (silica) Rf=0.51 (10% MeOH/AcOEt).
MS-ESI(+): m/z=315 [M+H]+, 337 [M+Na]+
$[\alpha]_D$=+19.3 (c=1, DMSO)

Example 2

Synthesis of [1R-(1α,2α,4α)-2,3-O-(1R,4R)-1,7,7-trimethylbicyclo[2.2.1]-hept-2-ylidene]-1-[bis(phenylmethyl)phosphate]-myo-inositol (Compound 3)

Compound 2 of Example 1 (2.5 g) is made anhydrous and taken up in anhydrous pyridine (30 ml). The solution is cooled (4° C.) under a nitrogen atmosphere and dibenzyl phosphochloridate (3.5 g) is added dropwise, with stirring. After stirring for 3 h, the mixture is diluted with ethyl acetate and then washed with a saturated aqueous sodium hydrogen carbonate solution. The organic phase is concentrated and then coevaporated with toluene, the residue is purified by chromatography on a silica column (2-15% MeOH/CH$_2$Cl$_2$). The desired compound is then crystallized from an AcOEt/heptane (1:4) mixture.

Yield 1.4 g (30%).
TLC (silica) Rf=0.25 (5% MeOH/AcOEt).
$[\alpha]_D$=−8.3 (c=1, CHCl$_3$).
$^{31}$P NMR (CDCl$_3$): δ (ppm)=−1.61.

Example 3

Synthesis of 4,5,6-tri-O-phenylmethyloxycarbonyl-[1R-(1α,2α,4α)-2,3-O-[(1R,4R)-1,7,7-trimethylbicyclo[2.2.1]-hept-2-ylidene]-1-[bis(phenyl-methyl)phosphate]-D-myo-inositol (Compound 4, Z=benzyloxycarbonyl)

Compound 3 of Example 2 (0.7 g) is taken up in dichloromethane, and then triethylamine (340 µl) and DMAP (6 mg) are added and the stirred solution is cooled (0° C.) under nitrogen. 1.04 ml of benzyloxycarbonyl chloride is added over a period of 30 min and then the mixture is kept stirring for 18 h at room temperature. The reaction mixture is washed with an aqueous sodium hydrogen carbonate solution (at 10%) and then with a saturated NaCl solution; the organic phase is concentrated under vacuum and the residue purified by chromatography on a silica column (2-10% AcOEt/toluene). The desired compound is obtained in the form of a gum.

Yield 0.7 g (57%).
TLC (silica) Rf=0.49 (20% AcOEt/toluene).
$[\alpha]_D$=−19.6 (c=1, CHCl$_3$).

Example 4

Synthesis of 4,5,6-tri-O-phenylmethyloxycarbonyl-1-[bis(phenylmethyl)phosphate]-D-myo-inositol (Compound 5)

Compound 4 of Example 3 (0.2 g) is dissolved in dichloromethane, the solution is cooled (0° C.) and 400 µl of a TFA/H$_2$O 95/5 mixture are added. After stirring for 3 h at 0° C., the mixture is evaporated and coevaporated four times in the presence of toluene. The residue is purified by chromatography on a silica column (AcOEt/toluene and then MeOH/toluene). The desired compound is obtained in the form of a foam.

Yield 0.16 g (57%).
TLC (silica) Rf=0.41 (MeOH/AcOEt/toluene, 1/2/7).
$[\alpha]_D$=−7.69 (c=1, CHCl$_3$).

Example 5

Synthesis of 2,3-O-carbonate-4,5,6-tri-O-phenylmethyloxycarbonyl-1-[bis(phenylmethyl)phosphate]-D-myo-inositol (Compound 6)

Compound 5 of Example 4 (0.42 g) is dissolved in anhydrous dichloromethane in the presence of triethylamine (210 µl) and the solution is cooled (0° C.) and then 430 µl of phosgene are added, and the mixture is kept stirring for 18 h at room temperature. The reaction mixture is diluted with dichloromethane and washed with a dilute HCl solution, and then with water. The organic phase is concentrated and the residue purified by chromatography on a silica column (15-50% AcOEt/hexane).

Yield 0.33 g (76%).
TLC (silica) Rf=0.46 (50% AcOEt/hexane).
$[\alpha]_D$=−16.3 (c=1, CHCl$_3$).

Example 6

Synthesis of 2,3-O-carbonate-1-phosphate-D-myo-inositol (Compound 7)

Compound 6 of Example 5 (0.2 g) in a THF/EtOH/H2O mixture is hydrogenated for 5 h in the presence of a 10% palladium on carbon catalyst (0.2 g) at room temperature. After filtration on celite, the filtrate is freeze-dried.

Yield 65 mg (100%).
HPLC (ODS; gradient (10 nm) 0-2% ACN/TEAAc 30 mM pH 6.8): Rt=4.52 min.
MS-ESI(−): m/z=285 [M−H]−.
$^{31}$P NMR (D$_2$O): δ ppm)=3.54.

Example 7

Synthesis of the derivatives 3-O-(5-benzyloxycarbamidopentyl)carbamoyl-D-myo-inositol-1-phosphate (Compound 8) (Isomer 3) and 2-O-(5-benzyloxycarbamidopentyl)carbamoyl-D-myo-inositol-1-phosphate (Compound 9) (Isomer 2)

Compound 7 of Example 6 (60 mg) is reacted with 150 mg of 5-benzyloxycarbamidopentylamine (monoBoc derivative of pentylamine) in 1.8 ml of anhydrous DMF. After 48 h, the solvent is evaporated and the product is purified by preparative HPLC in order to separate compounds 8 and 9.

Yield of compound 8 (isomer 3): 40 mg (35%), of compound 9 (isomer 2): 37 mg (34%).

HPLC (ODS; gradient (10 min) 0-2% and then (15 min) 2 to 60% ACN/TEAAc 30 mM pH 6.8): Rt=18.6 min (isomer 2)

$^{31}$P NMR (D$_2$O): δ ppm)=2.35.

Example 8

Synthesis of the derivatives 3-O-(5-aminopentyl)carbamoyl-D-myo-inositol-1-phosphate (Compound 10) or 2-O-(5-aminopentyl)carbamoyl-D-myo-inositol-1-phosphate (Compound 11)

Twenty one milligrams of compound 8 or of compound 9 of Example 7 are dissolved in 2 ml of an ethanol/water (1/1) mixture and are hydrogenated for 5 h in the presence of a 10% palladium on carbon catalyst (0.2 g) at room temperature. After filtration on celite, the filtrate is freeze-dried.

Yield of compounds 10 or 11: 15 mg (90%).

Compound 10: HPLC (ODS; gradient (10 min) 0-2% ACN/TEAAc 30 mM pH 6.8): Rt=3.75 min.

Compound 10 is 3-O-(5-aminopentylcarbamoyl-D-myo-inositol-1-phosphate (in the form of a triethylammonium salt).

HPLC (ODS; gradient (10 min) 0-2% ACN/TEAAc 30 mM pH 6.8): Rt=3.75 min.

MS-ESI(−): m/z=387 [M−H]−. MS-ESI(+): m/z=389 [M−H]+.

$^{31}$P NMR (D$_2$O): δ ppm)=3.79.

$^{1}$H NMR: (D$_2$O, 400 MHz, (ppm)): 5.21 (dd, 1H, H$_2$); 3.97 (ddd, 1H, H$_1$); 3.76-3.57 (m, 2H, H$_3$+H$_6$); 3.50 (dd, 1H, H$_4$); 3.29 (m, 1H, H$_5$); 3.19-2.96 (m, 8H, CH$_2$ (arm)+CH$_2$ (Et$_3$N)); 2.90 (dd, 2H, CH$_2$ (arm)); 1.59 (m, 2H, CH$_2$ (arm)); 1.47 (m, 2H, CH$_2$(arm)); 1.34 (m, 2H, CH$_2$(arm)); 1.18 (t, 9H, CH$_3$ (Et$_3$N)).

$^{13}$C NMR: (D$_2$O, δ2.9 MHz, (ppm)): 161.0 (C=O); 77.2 (C2); 76.9 (C5); 76.0 (C1); 75.3 (C3); 75.1 (C4); 72.5 (C6); 42.8, 42.2, 31.0, 29.1 and 25.5 (CH$_2$ arm).

Compound 11 is 2-O-(5-aminopentylcarbamoyl)-D-myo-inositol-1-phosphate (in the form of a triethylammonium salt).

HPLC (ODS; isocratic 2 min at 5% and then gradient (20 min) 5-45% ACN/TEAAc 30 mM pH 6.8): Rt=3.84 min.

MS-ESI(−): m/z=387 [M−H]−. MS-ESI(+): m/z=389 [M+H]+.

$^{1}$H NMR: (D$_2$O, 400 MHz, (ppm)): 4.52 (dd, 1H, H$_3$); 4.24 (dd, 1H, H$_2$); 3.88 (ddd, 1H, H$_1$); 3.71-3.68 (m, 2H, H$_4$ and H$_6$); 3.33 (m, 1H, H$_5$); 3.11-2.06 (m, 5H, CH$_2$ (arm)+CH2 (Et$_3$N)); 2.90 (dd, 2H, CH$_2$ (arm)); 1.58 (m, 2H, CH$_2$ (arm)); 1.46 (m, 2H, CH$_2$(arm)); 1.31 (m, 2H, CH$_2$(arm)); 1.18 (t, 9H, CH$_3$ (Et$_3$N)).

$^{13}$C NMR: (D$_2$O, 62.9 MHz, (ppm)): 160.4 (C=O); 77.2-76.6-75.7-74.8-73.1-72.5 (C inositol); 42.8, 42.1, 31.0, 29.1 and 25.4 (CH$_2$ arm).

$^{31}$P NMR (D$_2$O): δ ppm)=2.31.

Example 9

Synthesis of a derivative 3-O-(5-biotinamidopentyl)carbamoyl-D-myo-inositol-1-phosphate (Compound 12)

To a solution of 2.35 mg (5.23 μmol) of 3-O-(5-aminopentyl)carbamoyl-1-phosphate-D-myo-inositol (compound 10) prepared according to Example 8 in 500 μl of phosphate buffer pH 8 are added 1.92 mg (5.6 μmol) of biotin-NHS ester (Aldrich) in a mixture of 200 μl of phosphate buffer and 300 μl of acetonitrile. By HPLC, the conversion is observed of the starting product peak (tR=16.5 min) to a novel compound (tR=16.9 min) [Lichrospher Merck RP18 E (5 μm) 125×4 mm, 1 ml/mn, A: water containing 0.05% TFA, B: acetonitrile, gradient 0 to 2% of B in 10 min, 2% to 15% B in 5 min, 15% to 100% B in 8 min, detection at 190 nm]. The compound is purified by RP-HPLC, after evaporation and drying under vacuum, 2.29 mg (70%) of IP1-biotin derivative (compound) are obtained. MS (ES+) [MH]+=615 (100%) (Calc: C$_{22}$H$_{39}$N$_4$O$_{12}$PS).

Example 10

Labeling of 3-O-(5-aminopentyl)carbamoyl-D-myo-inositol-1-phosphate with CY5: CY5-IP1 Conjugate (Compound 13)

0.96 mg (1.96 μmol) of 3-O-(5-aminopentyl)carbamoyl-D-myo-inositol-1-phosphate (compound 10), prepared according to Example 8, is weighed in an Eppendorf tube, 400 μl of carbonate buffer pH 9 are added, followed by 2 equivalents of sulfonated CY5-monoNHS (Amersham Pharmacia) in 163 μl of DMF. The mixture is analyzed and purified by RP-HPLC (Vydac RP18; 1 ml/min; gradient (30 min) 10-27% ACN/H2O at 1% TFA); the peak is collected at tR ~17 min. 0.64 μmol of compound 13 is obtained.

Yield=32%.

Example 11

Preparation of 3-O-(4-carboxybutyramido-5-pentyl)carbamoyl-D-myo-inositol-1-phosphate (Compound 31) and N-hydroxysuccinimide Derivative (Compound 32) (FIG. 5)

2 mg (4.0 μmol) of 3-O-(5-aminopentyl)carbamido-1-phosphate-D-myo-inositol (compound 10), prepared according to Example 8, are weighed in an Eppendorf tube, 200 μl of 0.1 M triethylammonium bicarbonate buffer pH 8 and 200 μl (that is 5 equivalents) of a glutaric anhydride solution in dimethylformamide (12 mg/ml) are added, after incubating for one hour, the pH is brought to 10 by adding triethylamine and after 15 min, the mixture is evaporated, neutralized (pH 7) with aqueous acetic acid (at 20%, V/V). The mixture is analyzed and purified by RP-HPLC (Vydac RP18; 1 ml/min; gradient (20 min) 0-10% ACN/50 mM triethylammonium bicarbonate) light scattering detector. The fraction corresponding to the predominant peak is collected, the fraction is evaporated to dryness (speed-vac) and then co-evaporated several times, adding each time 200 μl of water. 3.0 μmol of compound 31 are obtained. Yield=75%.

Compound 31 thus obtained is evaporated to dryness in an Eppendorff tube, taken up in DMF (200 μl) containing 1.75 μl of diisopropylethylamine, 1.3 mg of TSTU [O—(N-succinimidyl)-N,N,N',N'-tetramethyluronium tetrafluoroborate] dissolved in 200 µl of DMF are added. The formation of NHS derivative is monitored by RP-HPLC HPLC (Vydac RP18; 1 ml/min; gradient (20 min) 0-10% ACN/trifluoroacetic acid at 0.1% in water detection at 190 nm). After reacting for 4 h, part of the DMF is evaporated (speed-vac) and the reaction medium is diluted with an aqueous trifluoroacetic acid solution at 0.1% (about 3 ml) and purified by RP-HPLC using the same conditions as for the analysis. The main fraction is collected, it is evaporated to dryness and dried under vacuum. 1.5 µmol of NHS derivative (32) are obtained. This compound is taken up in a minimum of water, aliquoted in Eppendorf tubes provided with screw caps and evaporated to dryness. The tubes are stored at −20° C. up to the time of use.

Example 12

Synthesis of a 3-O-[5-(3-maleimidopropionamido)pentyl]carbamoyl-D-myo-inositol-1-phosphate derivative. (Compound 33) (FIG. 5)

To a solution of 4.04 mg (9 µmol) of 3-O-(5-aminopentyl)carbamoyl-1-phosphate-D-myo-inositol (compound 10) prepared according to Example 8 in 2 ml of 0.1 M phosphate buffer pH 7 cooled in an ice bath are added 5.54 mg (20 µmol) of N-hydroxysuccinimidyl 3-maleimidopropionate (Aldrich) dissolved in 400 µl of acetonitrile in 100 µl fractions every 5 min, allowing the mixture to return to 20° C., and then the mixture is left to react for two hours. The conversion of the starting material peak to a novel compound (tR=12.7 min) [Lichrospher Merck RP18 E (5 µm) 125×4 mm, 1 ml/min, A: water containing 0.05% of TFA, B: acetonitrile, gradient 0 to 2% of B over 10 min, 2% to 15% B over 5 min, 15% to 100% B over 8 min, detection at 190 nm] is observed by HPLC. The compound is purified by RP-HPLC using the same solvents, after evaporation and drying under vacuum, 1.15 mg (21%) of IP1 maleimide derivative (compound 33) are obtained. MS (ES$^+$) [MH]$^+$=420 (30%) [M+Na]$^+$=562 (50%) (Calc: $C_{19}H_{30}N_3O_{13}P$). The product is aliquoted and stored at −20° C. up to the time of use.

Example 13

Coupling of IP1-maleimide with XL665

The allophycocyanin XL665 (CIS BIO INTERNATIONAL) is activated beforehand with 5 equivalents of SPDP (N-hydroxysuccinimidyl 3-[2-pyridylthio]propionate) in 0.1 M phosphate buffer pH=7 for 30 minutes at room temperature. The reaction mixture is then reduced with 20 mM DTT (dithiothreitol) in the same buffer. The activated XL665 (XL665-SH) is then purified by exclusion chromatography using an Amersham Biosciences G25 super fine HR10/30 column. The elution buffer for the purification step is a 0.1 M phosphate buffer pH=7.

The coupling step is performed by adding 5 equivalents of IP1-maleimide of Example 12 to 1 equivalent of XL665-SH and allowing the mixture to react overnight at 4° C.

The IP1-XL665 conjugate is then purified by exclusion chromatography using a G25 super fine HR10/30 column (Amersham Biosciences). The elution buffer for the purification step is a 0.1 M phosphate buffer pH=7.

Example 14

Preparation of an Immunogen by Coupling between BSA and 3-O-(5-aminopentyl)carbamoyl-D-myo-inositol-1-phosphate A BSA (bovine serum albumin) solution at 10 mg/ml is prepared in PBS (phosphate buffered saline: 11 mM phosphate 140 mM NaCl pH 7.2). In an Eppendorf tube: 240 µl of BSA solution (that is 2.4 mg) and 300 µl of 3-O-(5-aminopentyl)carbamido-1-phosphate-D-myo-inositol analog prepared according to Example 8 and then 60 µl of glutaraldehyde (that is 1% of the final volume) are mixed. The mixture is incubated for two hours at 20° C., with stirring, and then 600 µl of a freshly prepared aqueous NaBH4 (sodium borohydride) solution are added, followed by dialysis overnight at 4° C. against PBS buffer. The conjugate is then aliquoted and stored at −20° C.

Example 15

Immunization

Mice are immunized (6 subcutaneous injections each performed using 50 µl of a solution of immunogen prepared according to Example 14 emulsified with the same volume of Freund's adjuvant). Blood samples are collected regularly and the antisera obtained are stored at −20° C.

Example 16

ELISA Test Allowing the Presence of Antibodies Specifically Recognizing IP1 to be Detected NUNC 96-well microtiter plates coated with streptavidin (13 pmol/wells) are used. 100 µl of IP1-biotin conjugate prepared according to Example 9 at a concentration of 0.25 µg/ml in PBS buffer containing 0.3% BSA are distributed. Incubation for 1 h 30 min at 20° C., followed by three washes with PBS 0.1% Tween20. The antisera which are diluted 1/10, 1/100 ... 1/10 000 are collected and distributed (100 µl/well) in the microtiter plate; control wells "blanks" are also prepared by distributing buffer alone. Incubation for 16 h at 4° C., followed by three washes with PBS 0.1% Tween20. 100 µl of conjugate anti-IgG (mouse)-peroxidase (Sigma # A 0168) diluted 1/60 000 in PBS 0.3% BSA are distributed. The mixture is incubated for 1 h at room temperature with stirring, and then three washes with PBS 0.1% Tween are performed. 100 µl of TMB (Sigma # T 8665) are distributed, the mixture is incubated for 30 min at room temperature with stirring and then 100 µl of stop reagent (Sigma # S5814) are distributed and the optical densities are measured at 450 nm.

$OD_{450nm}$ values>0.5 are observed in the wells containing serum dilutions below 1/10 000, which shows the presence, in these sera, of mouse antibodies directed against the IP1 analog.

Example 17

Specificity of the Anti-IP1 Antibodies Evaluated by ELISA (FIG. 10)

NUNC 96-well microtiter plates coated with streptavidin (13 pmol/well) are used. 100 µl of IP1-biotin conjugate prepared according to Example 9 at a concentration of 0.25 µg/ml are distributed and the mixture is incubated for 2 h 30 min at room temperature with stirring. The mixture is washed three times with water containing 0.1% Tween20. 50 µl of solutions of competitors are added so as to prepare the following final concentration ranges: myo-inositol (10 nM at 1 mM), IP1 Sigma (1 nM to 100 µM), IP2 (1 nM to 100 µM), IP3 (1 nM to 100 µM), PiP2 (1 nM to 100 µM) as well as 50 µl of culture supernatants secreting anti-IP1 antibodies. The mixture is incubated for 16 h at 4° C. and then washed three times with water containing 0.1% Tween20. 100 µl of conjugate anti-IgG (mouse)-peroxidase (Sigma # A 0168) diluted 1/60 000 in PBS 0.3% BSA are added. The mixture is incubated for 1 h at room temperature with stirring and then three washes are performed with 10 PBS 0.1% Tween20. 100 µl of TMB substrate (Sigma # T 8665) are distributed and the mixture is incubated for 30 min at room temperature with stirring and then 100 µl of stop reagent (Sigma # S5814) are distributed and the optical densities are measured at 450 nm.

The optical density at 450 nm is plotted against the logarithm of the concentration of compound whose competition it is desired to test. For all the compounds tested in competition, the maximum optical density OD450~1.5 is observed at the lowest concentrations (1 nM). It is observed that myo-inositol does not cause a decrease in the signal even at concentrations of 1 mM whereas IP1 induces a reduction in the signal for concentrations below the micromolar range, which shows that the antibody contained in the serum is capable of specifically recognizing the IP1 molecule by exhibiting a sufficient affinity to be used in an assay. Likewise, the various metabolites, such as PIP2, were tested and are not recognized by the antibody, confirming the specificity of the recognition of IP1 by the anti-IP1 antibodies.

Figure 11:
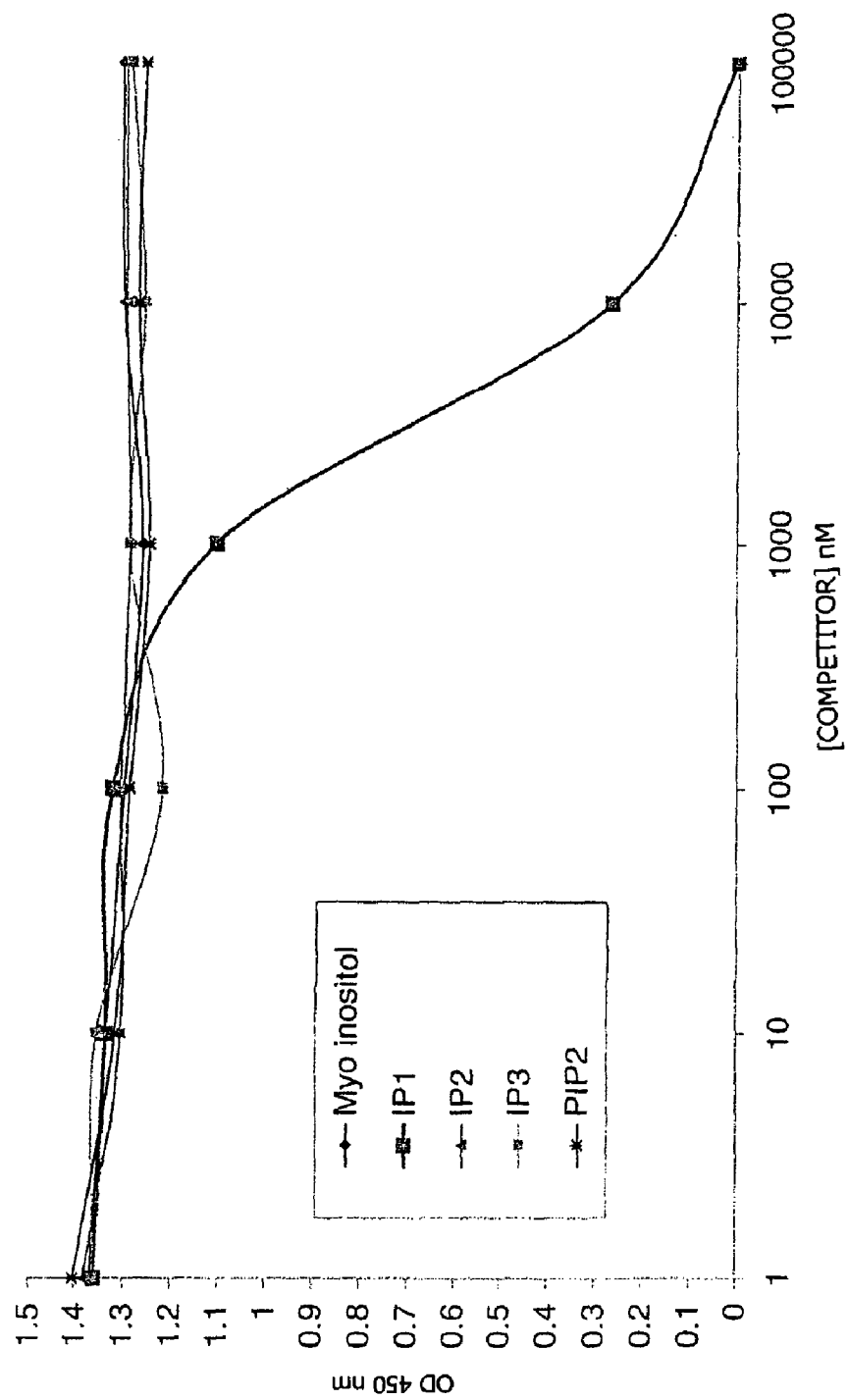
FIG. 11 is a graph showing the specificity of the anti-IP1 antibody used in the ELISA test.

The graph of FIG. 11 shows the specificity of the anti-IP1 antibody used in the ELISA test. Indeed, only the use of IP1 as competitor makes it possible to measure inhibition of the signal.

Example 18

Assay of IP1 by an HTRF Test

Specificity of the Anti-IP1 Antibodies

All the solutions are prepared in 100 mM HEPES buffer pH 7 containing 0.1% BSA and 0.4 M KF.NB. 50 µl of solution of competitors are distributed into the wells of a black bottom microtiter plate so as to obtain the following final concentrations: myo-inositol (10 nM to 1 mM), IP1 Sigma (1 nM to 1 mM), IP2 (1 nM to 100 µM), IP3 (1 nM to 100 µM), PiP2 (1 nM to 100 µM). 50 µl of a 10 nM solution of IP1-CY5 conjugate of Example 10, 50 µl of a solution containing 1.5 nM of an anti-IP1 antibody labeled beforehand with europium cryptate are then distributed in the order indicated. Two wells are also distributed in which the 50 µl of competitors are replaced with 50 µl of buffer so as to constitute blanks (negative controls). The mixture is incubated for 2 h at 4° C. and a time-resolved fluorescence measurement is performed (td=50 µs, tg=400 µs) at 620 nm and 665 nm on a Rubystar® apparatus (BMG Labtech). The $\Delta F$ values are calculated using the blank values as reference. The percentages of inhibition obtained with the various competitors are then calculated with the delta F values taking, as 100% value, the signal obtained in the presence of an excess of the IP1 competitor.

The graph of FIG. 12 shows the high specificity of the anti-IP1 antibody used. Indeed, only the use of IP1 as competitor makes it possible to measure inhibition of the signal.

The conjugate according to Example 13 may be used in the same manner as the IP1-CY5 conjugate in an HTFR test.

Example 19

Synthesis of the Derivatives 4-O-(5-aminopentylcarbamoyl-D-myo-inositol-1-phosphate (Compound 18D) or 5-O-(5-aminopentylcarbamoyl-D-myo-inositol-1-phosphate (Compound 19D)

Commercial myo-inositol (compound 1) is treated with 1,1-diethoxycyclohexane according to the protocol by Dreef et al. (*Tetrahedron*, 1991, 47(26), 4709-4722), purifying the reaction mixture directly and without carrying out the additional acid treatment (designed to increase the proportion of the 1,2:4,5-di-O-cyclohexylidene-myo-inositol isomer), 28% of the 1,2:4,5-di-O-cyclohexylidene-myo-inositol isomer, 47% of the 2,3:4,5-di-O-cyclohexylidene-myo-inositol isomer (34) and 18% of the 1,2:5,6-di-O-cyclohexylidene-myo-inositol isomer are thus obtained.

1-O-Butyryl-2,3:4,5-di-O-cyclohexylidene-myo-inositol (36) and 6-O-butyryl-2,3:4,5-di-O-cyclohexylidene-myo-inositol (37)

Compound 34 (37 g, 11 mmol) is suspended in toluene (250 ml) and then dibutyltin oxide (30 g, 12 mmol) is added. The mixture is heated to reflux temperature in a Dean-Stark apparatus for 3 hours. The solution is then concentrated under vacuum.

The residue is then taken up in 200 ml of anhydrous DMF. This solution is cooled to −40° C., and cesium fluoride (34 g, 22 mmol) and butyryl chloride (12 ml, 11.6 mmol) are added. The reaction medium is stirred at room temperature for 12 hours. The reaction mixture is diluted with 600 ml of dichloromethane and washed with 400 ml of water. The organic phase is dried over $Na_2SO_4$, filtered and then concentrated. Compounds 36 (27.6 g, 62%) and 37 (3.6 g, 8%) are obtained pure by chromatography on silica gel (hexane/ethyl acetate, 4/1).

Rf=0.33 (37) and 0.21 (36) (hexane/ethyl acetate, 4/1).

36: $^1$H NMR ($CDCl_3$, 400 MHz, δ (ppm)): 4.98 (t, 1H, $H_1$, $J_{1-2}=J_{1-6}=4.6$ Hz); 4.59 (dd, 1H, $H_2$, $J_{2-3}=6.1$ Hz); 4.36 (dd, 1H, $H_3$, $J_{3-4}=8.1$ Hz); 4.09 (dd, 1H, $H_6$, $J_{5-6}=9.0$ Hz); 3.87 (dd, 1H, $H_4$, $J_{4-5}=10.5$ Hz); 3.47 (dd, 1H, $H_5$); 2.44-2.32 (m, 4H, 2*$CH_2$); 1.78-1.33 (m, 20H, 10*$CH_2$ of cyclohexylidene); 0.99 (t, 3H, $CH_3$, J=7.4 Hz).

37: $^1$H NMR ($CDCl_3$, 400 MHz, δ (ppm)): 5.21 (dd, 1H, $H_6$, $J_{1-6}=2.9$, $J_{5-6}=8.7$ Hz); 4.46 (dd, 1H, $H_2$, $J_{1-2}=3.9$, $J_{2-3}=7.1$ Hz); 4.39 (dd, 1H, $H_3$, $J_{3-4}=7.7$ Hz); 4.20 (dd, 1H, $H_4$, $J_{4-5}=10.6$ Hz); 3.89 (dd, 1H, $H_1$); 3.61 (dd, 1H, $H_5$); 2.40-2.32 (m, 4H, 2*$CH_2$); 1.79-1.24 (m, 20H, 10*$CH_2$ of cyclohexylidene); 0.99 (t, 3H, $CH_3$).

1-O-Butyryl-2,3:4,5-di-O-cyclohexylidene-D-myo-inositol (36D)

1-Butyryl-2,3:4,5-di-O-cyclohexylidene-myo-inositol 36 (18 g, 43.9 mmol) is dissolved in a hexane/ether (200 ml 10/1) and 0.1 M phosphate buffer (pH~7, 90 ml) mixture. Porcine pancreatic lipase (PLL) (54 g) is added and the reaction medium is kept stirring at 37° C. for 1 week. The medium is left to separate by decantation. The supernatant is removed and the remainder is centrifuged. The supernatant is separated from the pellet. The supernatants are combined, dried over $MgSO_4$, filtered and then concentrated. The diol 34L (4.7 g, 65%) and the ester 36D (8.9 g, 98%) are separated and obtained pure by chromatography on silica gel (open column, hexane/ethyl acetate, 4/1→1/1).

Rf=0.73 (36D) and 0.35 (34L) (hexane/ethyl acetate, 1/1).

[α]D=−8.3 (c=1.06, CHCl3) (36D).

[α]D=−16.47 (c=0.61, CHCl3) (34L).

2,3:4,5-di-O-Cyclohexylidene-D-myo-inositol (34D)

Compound 36D (8.9 g, 21.7 mmol) is dissolved in methanol (70 ml). 45 ml of a 5M sodium hydroxide solution are added dropwise. The reaction mixture is stirred at room temperature for 18 hours. The methanol is evaporated under reduced pressure, the residue is diluted with 200 ml of dichloromethane. The aqueous phase is extracted with 200 ml of ethyl acetate. The organic phases are combined and concentrated. Compound 34D (6.8 g, 92%) is obtained pure by chromatography on silica gel (open column: solid deposit, H/E, 1/1). Yield=92%. Rf=0.35 (hexane/ethyl acetate, 1/1).

6-O-Benzyl-2,3:4,5-di-O-cyclohexylidene-D-myo-inositol (37D)

Compound 34D (1 g, 2.9 mmol) is suspended in toluene (28 ml) and then dibutyltin oxide (0.8 g, 3.2 mmol) is added. The mixture is heated under reflux in a Dean-Stark apparatus for 3 hours. The solution is then concentrated under vacuum. The residue is then taken up in 16 ml of anhydrous DMF. This solution is cooled to −20° C., and cesium fluoride (0.9 g, 5.8 mmol) and benzyl bromide (0.25 ml, 2.9 mmol) are added. The reaction medium is stirred at room temperature for 12 hours. The reaction mixture is diluted with 60 ml of dichloromethane and washed with 30 ml of water. The organic phase is dried over magnesium sulfate, filtered and then concentrated under a high vacuum. Compound 37D (0.96 g, 76%) is obtained pure by chromatography on a silica gel (open column, hexane/ethyl acetate, 1/1). Yield=76%.

6-O-Benzyl-2,3:4,5-di-O-cyclohexylidene-5-O-(o-xylylenedioxyphosphoryl)-D-myo-inositol (38D)

Compound 37D (0.83 g, 1.93 mmol) is dissolved in 45 ml of anhydrous dichloromethane. o-Xylene-N,N'-diisopropylphosphoramidite (1.03 g, 3.86 mmol) and 1-H-tetrazole (0.338 g, 4.83 mmol) are added. The medium is kept stirring at room temperature under argon for 1 hour. The medium is then cooled to 0° C. and 0.36 ml of tert-butyl hydroperoxide is added dropwise. The reaction mixture is allowed to return to room temperature, and then washed with 20 ml of water. The organic phase is dried over magnesium sulfate, filtered and concentrated. The product 38D (980 mg) is obtained pure by chromatography on silica gel (open column, hexane/ethyl acetate, 7/3→1/1).

Yield=83%.
Rf=0.45 (hexane/ethyl acetate, 1/1).
Melting point: 59° C.
$^{31}$P NMR (CDCl$_3$, 161.98 MHz, δ (ppm)): −1.48
$^{13}$C NMR (CDCl$_3$, 100.62 MHz, δ (ppm)): 138.2+135.7 (Cipso); 129.6-128.1 (Caro); 113.7+112.4 (Cipso); 79.6 (C$_6$); 78.6 (C$_5$); 77.9 (C$_1$); 77.6 (C$_4$); 76.5 (C$_3$); 74.4 (C$_2$, J$_{C-P}$=5.1 Hz); 72.4 (CH$_2$Ph); 68.9 (CH$_2$Ph, J$_{C-P}$=3.7 Hz); 37.0+36.9+36.7+34.6+25.5+25.4+24.3+24.2+24.1+23.9 (C$_{cyclo}$).

6-O-Benzyl-2,3-β-cyclohexylidene-5-O-(o-xylylenedioxyphosphoryl)-D-myo-inositol (39D)

The product 38D (0.98 g, 1.6 mmol) is dissolved in 20 ml of a 0.1 Methylene glycol solution in dichloromethane. para-Toluenesulfonic acid (0.13 g) is added. The reaction medium is neutralized after 2 hours by adding triethylamine and concentrated under reduced pressure. The residue obtained is purified by chromatography on a silica gel column (open column, deposition in CH$_2$Cl$_2$/MeOH, 95/5, elution CH$_2$Cl$_2$/MeOH, 99/1→95/5) to give the compounds 39D (0.357 g, 42%) obtained in the form of a gum. Rf=0.6 (pure ethyl acetate).

$^1$H NMR (acetone D$_6$, 400 MHz, δ (ppm)): 7.50-7.17 (m, 9H, Haro); 5.46 (dd, 1H, CH$_2$OP, J$_{AB}$=13.5, J$_{H-P}$=16.5 Hz); 5.42 (dd, 1H, CH$_2$OP, J$_{AB}$=13.5, J$_{H-P}$=16.5 Hz); 5.14-4.90 (m, 3H, 2*H of CH$_2$OP+H of CH$_2$Ph); 4.82 (d, 1H, CH$_2$Ph, J=11.1 Hz); 4.80 (ddd, 1H, H$_1$, J$_{1-2}$=4.2, J$_{1-6}$=8.4, J$_{1-P}$=7.8 Hz); 4.66 (dd, 1H, H$_2$, J$_{2-3}$=5.5 Hz); 4.20 (dd, 1H, H$_3$, J$_{3-4}$=7.0 Hz); 3.91 (dd, 1H, H$_6$, J$_{5-6}$=J$_{1-6}$=8.4 Hz); 3.78 (dd, 1H, H$_4$, J$_{4-5}$=9.2 Hz); 3.58 (dd, 1H, H$_5$); 1.81-1.36 (m, 10H, 5*CH$_2$ of cyclohexylidene).
$^{31}$P NMR (acetone D$_6$, 161.98 MHz, δ (ppm)): −4.11.

6-O-Benzyl-4,5-carbonate-2,3-O-cyclohexylidene-5-O-(o-xylylenedioxyphosphoryl)-D-myo-inositol (40D)

The diol (39D) (0.13 g, 0.24 mmol) is dissolved in 3 ml of anhydrous dichloromethane. 1,1'-Carbonyldiimidazole (120 mg, 0.72 mmol) is added. The reaction mixture is kept stirring under argon overnight. The solution is concentrated. The residue obtained is purified by chromatography on a silica gel column (open column, hexane/ethyl acetate, 7/3→100% ethyl acetate) to give compound 40D in the form of a white gum (118 mg, 87%). Rf=0.63 (hexane/ethyl acetate, 3/7).

[α]D=−6.1 (c=0.97, CHCl3) (40D).
$^1$H NMR (CDCl$_3$, 400 MHz, δ (ppm)): 7.47-7.22 (m, 9H, Haro); 5.30 (dd, 1H, CH$_2$OP, J$_{AB}$=13.6, J$_{H-P}$=16.6 Hz); 5.25 (dd, 1H, CH$_2$OP, J$_{AB}$=13.6, J$_{H-P}$=16.6 Hz); 5.24 (dd, 1H, CH$_2$OP); 5.10 (dd, 1H, CH$_2$OP); 4.84 (td, 1H, H$_1$, J$_{1-2}$=3.0, J$_{1-6}$=2.2, J$_{1-P}$=8.8 Hz); 4.79 (d, 1H, CH$_2$ of benzyl, J$_{AB}$=11.8 Hz); 4.71 (d, 1H, CH$_2$ of benzyl); 4.65-4.52 (m, 3H, H$_2$+H$_3$+H$_4$); 4.26 (dd, 1H, H$_6$, J$_{5-6}$=8.0, J$_{1-6}$=2.2 Hz); 4.15 (m, 1H, H$_5$); 1.80-1.21 (m, 10H, 5*CH$_2$ of cyclohexylidene).
$^{31}$P NMR (CDCl$_3$, 161.98 MHz, δ (ppm)): −1.49
IR: 1812-1840 (C═O); 1284 (P═O); 1007-1021-1091 (P—O).

4-O-(5-Aminopentylcarbamoyl)-6-O-benzyl-2,3-O-cyclohexylidene-1-O-(o-xylylenedioxyphosphoryl)-D-myo-inositol "isomer 4 in protected form" (41D) and 5-O-(5-aminopentylcarbamoyl)-6-O-benzyl-2,3-O-cyclohexylidene-1-O-(o-xylylenedioxyphosphoryl)-D-myo-inositol "isomer 5 in protected form" (42D)

Compound 40D (115 mg, 0.21 mmol) is dissolved in 3 ml of anhydrous dichloromethane and then 5-benzyloxycarbamidopentylamine (monoBoc derivative of the pentylamine as in Example 7) (153 mg, 0.65 mmol) dissolved beforehand in 2 ml of anhydrous dichloromethane is added dropwise. The reaction is allowed to progress at room temperature for 12 hours. The solution is concentrated. The residue is purified by chromatography on silica gel (open column, hexane/ethyl acetate, 1/4→100% ethyl acetate) to give compounds 41D (78 mg, 40%) and 42D (78 mg, 40%).

41D: $^1$H NMR (CDCl$_3$, 400 MHz, δ (ppm)): 7.43-7.17 (m, 19H, Haro); 5.36 (dd, 1H, CH$_2$OP, J$_{AB}$=13.6, P$_{H-P}$=12.1 Hz); 5.27 (dd, 1H, CH$_2$OP, J$_{AB}$=13.6, J$_{H-P}$=16.6 Hz); 5.18-4.80 (m, 8H, 2*H of CH$_2$OP+4*H of CH$_2$Ph+H$_4$+H$_1$); 4.71-4.66 (m, 1H, H$_2$); 4.15 (dd, 1H, H$_3$, J$_{2-3}$=J$_{3-4}$=6.8 Hz); 3.97 (dd, 1H, H$_6$, J$_{5-6}$8.1 Hz); 3.60 (dd, 1H, H$_5$, J$_{4-5}$=8.1 Hz); 3.31-3.11 (m, 4H, 2*CH$_2$N); 1.92-1.31 (m, 16H, 3*CH$_2$ of the arm+5*CH$_2$ of cyclohexylidene).
$^{31}$P NMR (CDCl$_3$, 161.98 MHz, δ (ppm)): −1.76.

4-O-(5-Aminopentylcarbamoyl)-D-myo-inositol-1-phosphate (18D)

A solution of compound 41D (75 mg, 0.094 mmol) in 16 ml of a methanol/chloroform (v/v) mixture is stirred under a hydrogen atmosphere in the presence of 10% palladium on carbon (80 mg) at room temperature for 68 hours at 10 bar.

After filtration on celite and washing with water, the filtrate is evaporated and then taken up in water and freeze-dried to give the compound 18D (18 mg, 53%).

$^1$H NMR (D$_2$O, 400 MHz, δ (ppm)): 4.81 (dd, 1H, H$_4$); 4.20 (bs, 1H, H$_2$); 3.87 (dd, 1H, H$_1$); 3.78 (dd, 1H, H$_6$); 3.68 (dd, 1H, H$_3$); 3.43 (dd, 1H, H$_5$); 3.20-3.05 (m, 2H, 2*H of CH$_2$—N); 2.91 (t, 2H, 2*H of CH$_2$—N, J=7.4 Hz); 1.63 (q, 2H, 2*H of CH$_2$—N, J=7.5 Hz); 1.50 (q, 2H, 2*H of CH$_2$—N, J=6.9 Hz); 1.37 (m, 2H, 2*H of CH$_2$—N).

$^{31}$P NMR (D$_2$O, 161.98 MHz, δ (ppm)): 3.98
MS-ESI (−): m/z 387 [M−H]$^-$.

5-O-(5-Aminopentylcarbamoyl)-D-myo-inositol-1-phosphate (19D)

A solution of compound 13D (58 mg, 73 μmol) in 16 ml of a methanol/chloroform (v/v) mixture, in the presence of 10% palladium on carbon (60 mg), is stirred at room temperature for 68 hours at 10 bar. After filtration on celite and washing with water, the filtrate is evaporated and then taken up in water and freeze-dried to give compound 16D.

$^1$H NMR (D$_2$O, 400 MHz, δ (ppm)): 4.50 (dd, 1H, H$_5$, J$_{4-5}$=9.8, J$_{5-6}$=9.6 Hz); 4.17 (bs, 1H, H$_2$); 3.91 (dd, 1H, H$_1$, J$_{1-6}$=9.6 Hz); 3.78 (dd, 1H, H$_6$); 3.67 (dd, 1H, H$_4$, J$_{3-4}$=10.0 Hz); 3.57 (dd, 1H, H$_3$, J$_{2-3}$=2.1 Hz); 3.20-3.05 (m, 2H, 2*H of CH$_2$—N); 2.91 (t, 2H, 2*H of CH$_2$—N, J=7.4 Hz); 1.59 (q, 2H, 2*H of CH$_2$—N, J=7.7 Hz); 1.47 (q, 2H, 2*H of CH$_2$—N, J=6.9 Hz); 1.32 (m, 2H, 2*H of CH$_2$—N).

$^{31}$P NMR (D$_2$O, 161.98 MHz, δ (ppm)): 3.75
MS-ESI (−): m/z 387 [M−H]$^-$.

5-O-(5-Aminopentylcarbamoyl)-D-myo-inositol-1-phosphate (19D)

A solution of compound 42D (58 mg, 73 μmol) in 16 ml of a methanol/chloroform (v/v) mixture, in the presence of 10% palladium on carbon (60 mg), is stirred at room temperature for 68 hours at 10 bar. After filtration on celite and washing with methanol and then with water, the filtrate is evaporated and then taken up in water and freeze-dried to give compound 19D.

$^1$H NMR (D$_2$O, 400 MHz, δ (ppm)): 4.50 (dd, 1H, H$_5$, J$_{4-5}$=9.8, J$_{5-6}$=9.6 Hz); 4.17 (bs, 1H, H$_2$); 3.91 (dd, 1H, H$_1$, J$_{1-6}$=9.6 Hz); 3.78 (dd, 1H, H$_6$); 3.67 (dd, 1H, H$_4$, J$_{3-4}$=10.0 Hz); 3.57 (dd, 1H, H$_3$, J$_{2-3}$=2.1 Hz); 3.20-3.05 (m, 2H, 2*H of CH$_2$—N); 2.91 (t, 2H, 2*H of CH$_2$—N, J=7.4 Hz); 1.59 (q, 2H, 2*H of CH$_2$—N, J=7.7 Hz); 1.47 (q, 2H, 2*H of CH$_2$—N, J=6.9 Hz); 1.32 (m, 2H, 2*H of CH$_2$—N).

$^{31}$P NMR (D$_2$O, 161.98 MHz, δ (ppm)): 3.75
MS-ESI (−): m/z 387 [M−H]$^-$.

Example 20

Synthesis of the 4-O-(5-biotinamidopentylcarbamoyl)-D-myo-inositol-1-phosphate Derivatives (Compound 43D)

To a solution of 1 mg (2.58 μmol) of 4-O-(5-aminopentylcarbamoyl)-1-phosphate-D-myo-inositol (compound 18D prepared according to Example 19) in 400 μl of HEPES buffer pH 8 are added 1.75 mg (5.16 μmol) of biotin-NHS ester (Aldrich) in 50 μl of DMF. A precipitate forms which is redissolved after addition of 450 μl of acetonitrile, the mixture is kept stirring for 30 min at room temperature. The disappearance of the starting material peak and the appearance of a novel compound having a retention time of 29.2 min [Chromolith Merck, 1.5 ml/min, A: water containing 0.1% of TFA, B: acetonitrile, gradient 0 to 5 min 0% B. 15 min 2% of B, 30 min 15% of B, 40 min 30% of B, detection at 190 nm] are observed by HPLC. The compound is purified by RP-HPLC, after evaporation and drying under vacuum, 1.2 mg (63%) of compound 43D are obtained.

Example 21

Synthesis of the 5-O-(5-biotinamidopentylcarbamoyl)-D-myo-inositol-1-phosphate Derivatives (Compound 44D)

A solution of 5-O-(5-aminopentylcarbamoyl)-1-phosphate-D-myo-inositol (compound 19D prepared according to Example 19) is treated with biotin-NHS ester, and then the reaction mixture is purified by RP-HPLC as described in Example 20, compound 44D is thus obtained.

Example 22

Preparation of an Immunogen by Coupling between BSA and 4-O-(5-aminopentylcarbamoyl)-D-myo-inositol-1-phosphate Following the protocol of Example 14, a conjugate is prepared between BSA (bovine serum albumin) and the 4-O-(5-aminopentylcarbamoyl)-D-myo-inositol-1-phosphate analog 18D (solution at 1 mg/ml in PBS) prepared according to Example 19. The conjugate is then aliquoted and stored at −20° C.

Example 23

Preparation of an Immunogen by Coupling between BSA and 5-O-(5-aminopentylcarbamoyl)-D-myo-inositol-1-phosphate Following the protocol of Example 14, a conjugate is prepared between BSA (bovine serum albumin) and the 5-O-(5-aminopentylcarbamoyl)-D-myo-inositol-1-phosphate analog 19D (solution at 1 mg/ml in PBS) prepared according to Example 19. The conjugate is then aliquoted and stored at −20° C.

Example 24

Assay of IP1 after Stimulation of CHO Cells Expressing the M1 Receptor by Acetylcholine (Agonist of the M1 Receptor)

Figure 13A:
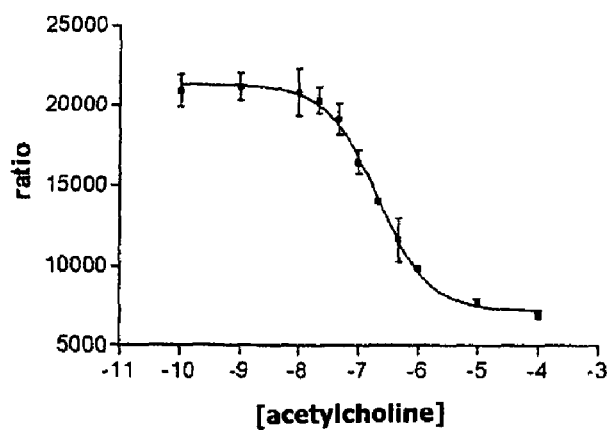
FIG. 13*a* illustrates a graph showing ratio versus acetylcholine.

80 000 CHO cells expressing the M1 muscarinic receptor, in 200 μl of F12 medium supplemented with 10% FCS, penicillin-streptomycin and nonessential amino acids are distributed in a 96-well opaque culture plate and incubated overnight at 37° C., 5% CO2. The culture medium is removed, and 50 μl of acetylcholine solutions (agonist LM1, 1 nM to 100 μM) diluted in KREBS buffer (10 mM HEPES pH 7.4, 150 mM NaCl, 4.2 mM KCl, 0.5 mM MgCl$_2$, 1 mM CaCl$_2$, 1 g/l glucose, 30 M LiCl) are distributed. Six wells are also distributed in which the acetylcholine is replaced with buffer in order, on the one hand, to determine the negative signal (3 wells) corresponding to the background noise, and, on the other hand, to also determine the "basal" signal for the assay (3 wells), that is to say the TR-FRET signal in the absence of stimulation. Incubation is performed for 30 minutes at 37° C., 5% CO$_2$. 25 μl of 4 nM solution of anti-IP1 antibody labeled beforehand with europium cryptate (to have 1 nM final in the assay) are then distributed, followed by 25 µl of a 12 nM solution of IP1 labeled with the fluorophore d2 (hereinafter IP1-d2), to have 3 nM final in the assay. These two reagents are diluted in 50 mM HEPES buffer pH 7, containing 0.2% BSA, 0.8M KF and 1% triton X100. In the wells used to determine the negative signal, IP1-d2 is replaced with buffer. Incubation is performed for 1 h at room temperature and a time-resolved fluorescence measurement (td=50 µs, tg=400 µs) is performed at 620 nm and 665 nm (E620 and E665 respectively) on a Rubystar® apparatus (BMG Labtech). From the E620 and E665 fluorescence intensity values, the E665/E620 intensity ratio is calculated and it is multiplied by 10 000 for the sake of convenience. The delta F values are calculated relative to the ratio measured in a well without IP1-d2, corresponding to the background noise (basal signal, cf. G. Mathis, Clin. Chem. 39 (1993) 1953 and application WO92/13264). The percentages of inhibition obtained as a function of the stimulation of the receptor are calculated from the delta F values with the delta F measured in the "basal signal" well with no drug equivalent to 0% inhibition. In the absence of acetylcholine, the measured signal resulting from the energy transfer between the anti-IP1 antibody labeled with europium cryptate and IP1-d2 is high. When the M1 receptor is stimulated with acetylcholine, IP1 is produced in the cell and the signal will decrease as a function of the acetylcholine concentration (FIG. 13A).

Figure 13B:
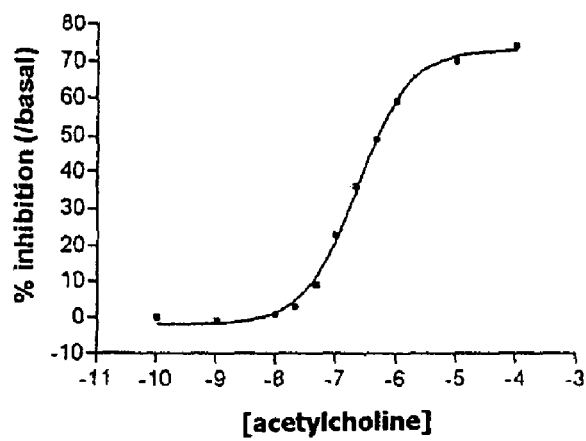
FIG. 13*b* illustrates a graph showing percent inhibition (/basal) versus acetylcholine.

This result may also be expressed by calculating the percentage inhibition of the basal signal (measured in the absence of acetylcholine) induced by the addition of an increasing concentration of acetyl choline (FIG. 13B)

Example 25

IP1 Assay after Stimulation of CHO Cells Expressing the M1 Receptors by Acetylcholine, in the Presence of Atropine (Antagonist of the M1 Receptor)

Figure 14A:
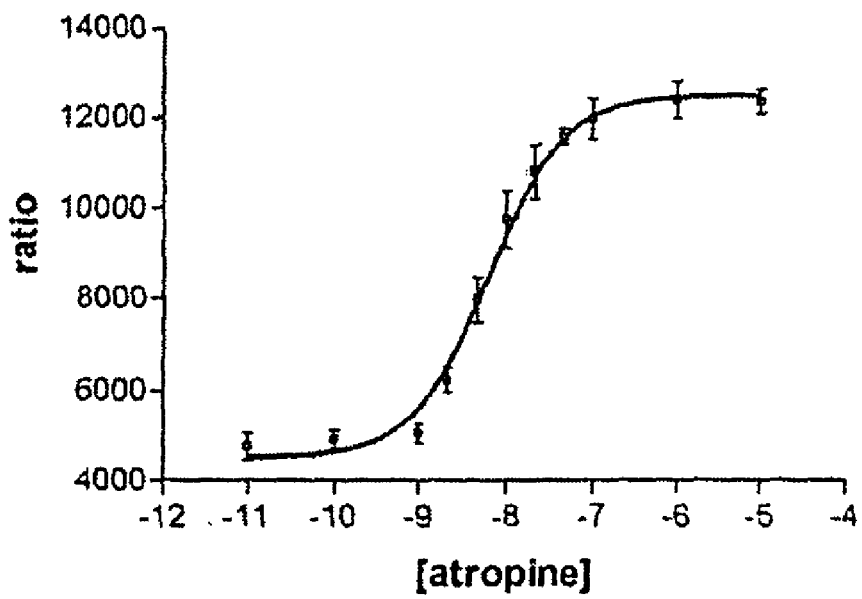
FIG. 14*a* is a graph of the signal from the energy transfer between the anti-IP1 antibody and IP1-d2.

80 000 CHO cells expressing the muscarinic receptor M1, in 200 µl of F12 medium supplemented with 10% FCS, penicillin-streptomycin and nonessential amino acids, are distributed in a 96-well opaque culture plate, and incubated overnight at 37° C., 5% $CO_2$. The culture medium is removed, and 40 µl of atropine solutions (0.125 nM to 12.5 µM) diluted in KREBS buffer (10 mM HEPES pH 7.4, 150 mM NaCl, 4.2 mM KCl, 0.5 mM MgCl2, 1 mM CaCl2, 1 g/l glucose, 30 mM LiCl) are distributed, and incubation is performed for 15 min at 37° C., 5% $CO_2$. Next, 10 µl of 3 µM acetylcholine solution in the same KREBS buffer are distributed. Six wells are also distributed in which the atropine and the acetylcholine are replaced with buffer in order, on the one hand, to determine the negative signal (3 wells) corresponding to the background noise, and, on the other hand, to also determine the "basal" signal for the assay (3 wells), that is to say the TR-FRET signal in the absence of stimulation. Incubation is performed for 30 minutes at 37° C., 5% $CO_2$. 25 µl of a solution containing 4 nM anti-IP1 antibody labeled beforehand with europium cryptate (in order to have 1 nM final in the assay) are then distributed, followed by 25 µl of a solution containing 12 nM IP1-d2 (in order to have 3 nM final in the assay). These two reagents are diluted in 50 mM HEPES buffer pH 7 containing 0.2% BSA, 0.8M KF and 1% triton X100. In the wells used to determine the negative signal, IP1-d2 is replaced with buffer. Incubation is performed for 1 h at room temperature and a time-resolved fluorescence measurement (td=50 µs, tg=400 µs) is performed at 620 nm and 665 nm (E620 and E665 respectively) on a Rubystar® apparatus (BMG Labtech). From the fluorescence intensity values E620 and E665, the E665/E620 intensity ratio is calculated and is multiplied by 10 000 for greater convenience. The delta F values are calculated relative to the ratio measured in a well with no IP1-d2 (negative signal, cf G. Mathis, Clin. Chem. 39 (1993) 1953 and application WO 92/13264). The percentages of inhibition obtained as a function of the stimulation of the receptor are calculated from the delta F values with the delta F for the basal point with no drug equivalent to 0% inhibition. In the presence of an increasing concentration of antagonist M1 (atropine), the activation by the agonist M1 (acetylcholine) will be inhibited. The cell will therefore produce less IP1 and the signal resulting from the energy transfer between the anti-IP1 antibody labeled with europium cryptate and IP1-d2 will increase (FIG. 14A).

Figure 14B:
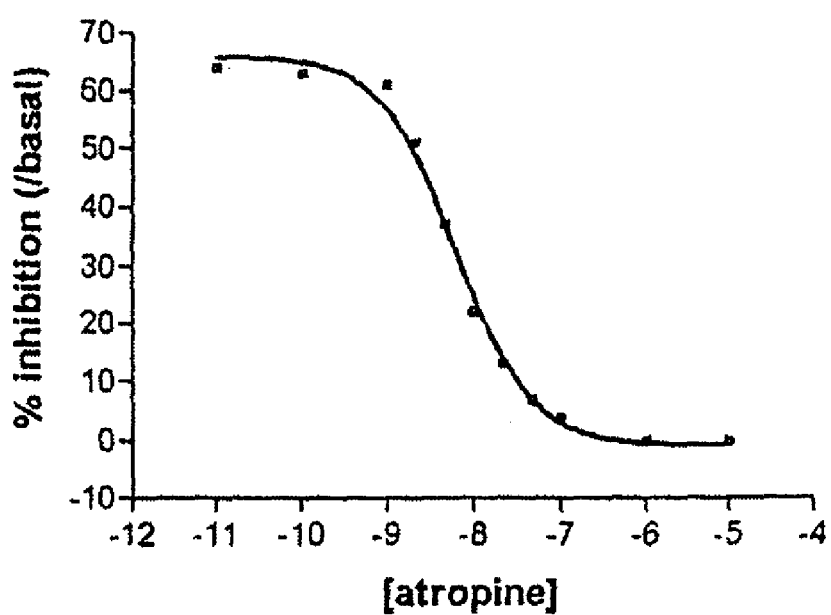
FIG. 14*b* is a graph of the variation of the inhibition of the signal by acetylcholine versus increasing concentrations of atropine.

This result may also be expressed by calculating the variation of the inhibition of the signal by acetylcholine in the presence of increasing concentrations of atropine (FIG. 14B).

Example 26

IP1 Assay on HEK-293 Cells Transiently Expressing the mGlu1 Receptor, Effect of a Positive Allosteric Modulator (PAM)

100 000 HEK-293 cells transfected beforehand by electroporation in order to express the mGluR1 receptor, in 100 µl of DMEM medium supplemented with 10% FCS, penicillin-streptomycin and nonessential amino acids, are distributed in a 96-well opaque culture plate. Incubation is performed for 3 h at 37° C., 5% $CO_2$, saturated with moisture, before changing the medium for 100 µl of DMEM containing glutamax (glutamine not degradable to glutamate) and free of serum. Incubation is performed overnight at 37° C. in an incubator containing 5% $CO_2$, saturated with moisture. The culture medium is removed by suction, and 30 µl of solutions of positive allosteric modulator (PAM) Ro 01-6128 (100 nM to 3 mM) diluted in KREBS buffer (10 mM HEPES pH 7.4, 150 mM NaCl, 4.2 mM KCl, 0.5 mM MgCl$_2$, 1 mM CaCL$_2$, 1 g/l glucose, 50 mM LiCl, 10/0 DMSO) are distributed. Six wells are also distributed in which the PAM is replaced with buffer in order, on the one hand, to determine the negative signal (3 wells) corresponding to the background noise, and, on the other hand, to also determine the "basal" signal for the assay (3 wells), that is to say the TR-FRET signal in the absence of stimulation. Incubation is performed for 30 minutes at 37° C., 5% $CO_2$. 15 µl of a solution containing 4 nM anti-IP1 antibody labeled beforehand with europium cryptate (in order to have 1 nM final in the assay) are then distributed, followed by 15 µl of a solution containing 12 nM IP1 labeled with fluorophore d2 (hereinafter IP1-d2) in order to have 3 nM final in the assay. These two reagents are then diluted in 50 mM HEPES buffer pH 7 containing 0.2% BSA, 0.8M KF and 10/0 triton X100. In the wells used to determine the negative signal, IP1-d2 is replaced with buffer. Incubation is performed for 2 h at 4° C. and a time-resolved fluorescence measurement (td=50 µs, tg=400 µs) is performed at 620 nm and 665 nm (E620 and E665 respectively) on a Rubystar® apparatus (BMG Labtech). From the fluorescence intensity values E620 and E665, the intensity ratio E665/E620 is calculated and is multiplied by 10 000 for greater convenience.

The delta F values are calculated by the ratio measured in a well with no IP1-d2 (negative signal, cf G. Mathis, Clin. Chem. 39 (1993) 1953 and application WO 92/13264). The percentages of inhibition obtained as a function of the stimulation of the receptor are calculated from the delta F values with the delta F measured in the "basal signal" well with no drug equivalent to 0% inhibition.

In the absence of PAM, the measured signal resulting from the energy transfer between the anti-IP1 antibody labeled with europium cryptate and IP1-d2 is high. When the mGlu1 receptor is activated with PAM, IP1 is produced in the cell and the signal will decrease as a function of the PAM concentration. This signal may be either the intensity ratio E665/E620, or the delta F.

This result may also be expressed by calculating the percentage inhibition of the basal signal (measured in the absence of PAM) induced by the addition of an increasing concentration of PAM.

Figure 15A:
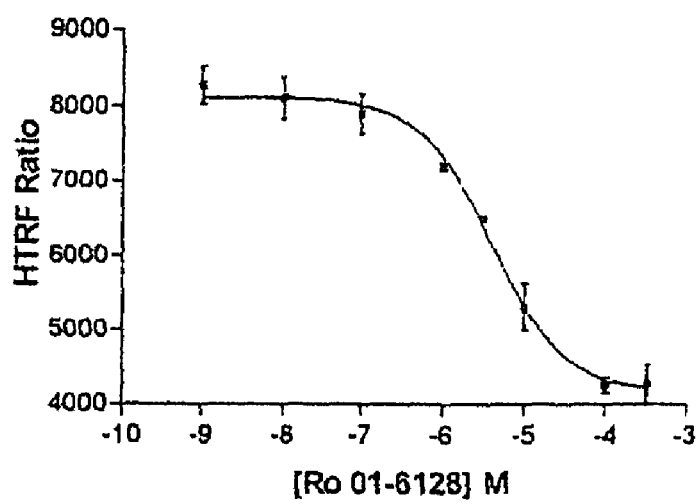
FIGS. 15*a* and 15*b* are graphs indicating the modulation of the signal as a function of a PAM concentration expressed either relative to the intensity are as delta F.
Figure 15B:
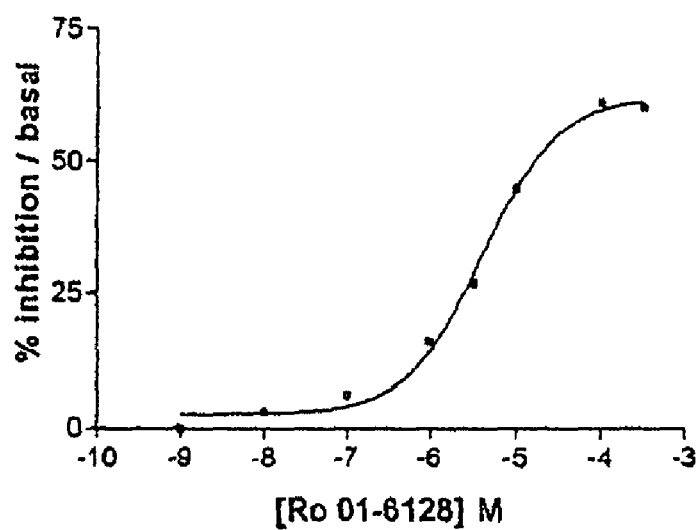

FIGS. 15A and 15B give the modulation of the signal as a function of the PAM concentration expressed either relative to the intensity or as delta F.

Example 27

Assay of IP1 on HEK-293 Cells Expressing the mGlu5 Receptor (Transient Transfection), Effect of an Inverse Agonist on mGluR5

100 000 HEK-293 cells transfected beforehand by electroporation in order to express the mGluR1 receptor, in 100 µl of DMEM medium supplemented with 10% FCS, penicillin-streptomycin and nonessential amino acids, are distributed in a 96-well opaque culture plate.

Incubation is performed for 3 h at 37° C., 5% $CO_2$, saturated with moisture, before changing the medium for 100 µl of DMEM containing glutamax (glutamine not degradable to glutamate) and free of serum.

Incubation is performed overnight at 37° C. in an incubator containing 5% $CO_2$, saturated with moisture. The culture medium is removed by suction, and 30 µl of solutions of inverse agonist (from 5 nM to 100 µM), 2-methyl-6-(phenylethynyl)pyridine (MPEP), diluted in KREBS buffer (10 mM HEPES pH 7.4, 150 mM NaCl, 4.2 mM KCl, 0.5 mM $MgCl_2$, 1 mM $CaCL_2$, 1 g/l glucose, 50 mM LiCl, 1% DMSO) are distributed. Six wells are also distributed in which the MPEP is replaced with buffer in order, on the one hand, to determine the negative signal (3 wells) corresponding to the background noise, and, on the other hand, to also determine the "basal" signal for the assay (3 wells), that is to say the TR-FRET signal in the absence of stimulation.

Incubation is performed for 1 hour at 37° C., 5% $CO_2$. 15 µl of a solution containing 4 nM anti-IP1 antibody labeled beforehand with europium cryptate (in order to have 1 nM final in the assay) are then distributed, and then followed by 15 µl of a solution containing 12 nM IP1 labeled with fluorophore d2 (hereinafter IP1-d2) in order to have 3 nM final in the assay. These two reagents are then diluted in 50 mM HEPES buffer pH 7 containing 0.2% BSA, 0.8M KF and 1% triton X100. In the wells used to determine the negative signal, IP1-d2 is replaced with buffer. Incubation is performed for 1 h at 4° C. and a time-resolved fluorescence measurement (td=50 µs, tg=400 µs) is performed at 620 nm and 665 nm (E620 and E665 respectively) on a Rubystar® apparatus (BMG Labtech). From the fluorescence intensity values E620 and E665, the intensity ratio E665/E620 is calculated and is multiplied by 10 000 for greater convenience.

The delta F values are calculated by the ratio measured in a well with no IP1-d2 (negative signal, cf G. Mathis, Clin. Chem. 39 (1993) 1953 and application WO 92/13264). The percentages of inhibition obtained as a function of the stimulation of the receptor are calculated from the delta F values with the delta F measured in the "basal signal" well with no drug equivalent to 0% inhibition.

In the absence of inverse agonist, the measured signal resulting from the energy transfer between the anti-IP1 antibody labeled with europium cryptate and IP1-d2 is relatively low because the mGluR5 receptor possesses a constitutive activity inducing a moderate production of intracellular IP1 which inhibits the TR-FRET signal. When the constitutive activity of the mGluR5 receptor is blocked by the addition of MPEP, that will lead to a decrease in the production of intracellular IP1. Consequently, the signal for the assay will increase as a function of the concentration of inverse agonist. This signal may be either the intensity ratio E665/E620 or the delta F.

This result may also be expressed by calculating the percentage inhibition of the basal signal (measured in the absence of MPEP) induced by the addition of increasing concentration of MPEP.

Figure 16A:
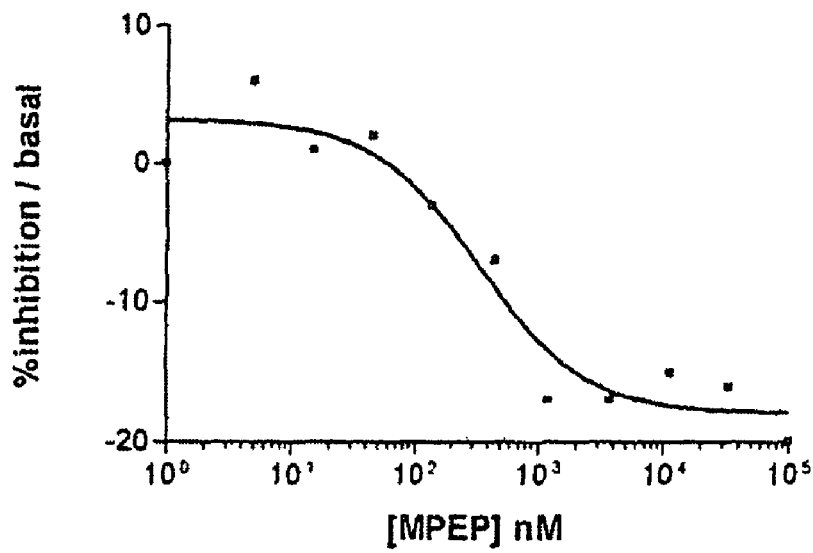
FIGS. 16*a* and 16*b* give the modulation of the signal as a function of the concentration of MPEP expressed either as an intensity ratio or as delta F.
Figure 16B:
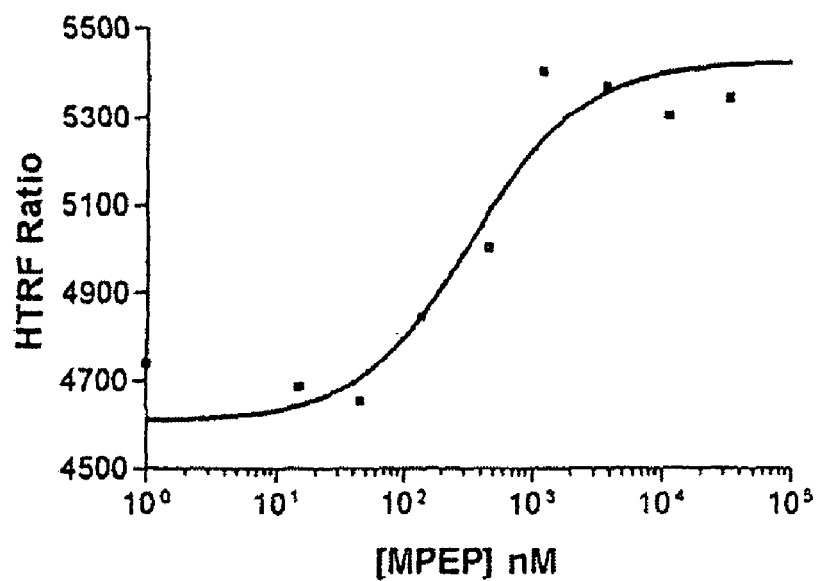

FIGS. 16A and 16B give the modulation of the signal as a function of the concentration of MPEP expressed either as an intensity ratio or as delta F.

The invention claimed is:
1. A compound of formula (I):

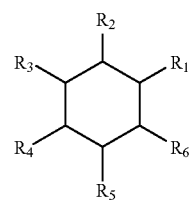

(I)

in which:
the substituents $R_1$, $R_2$, $R_3$, $R_4$, $R_5$, $R_6$ are chosen from:
—OH, —$OPO_3^{2-}$, —OPO(OH)$_2$ or —OPO(OH)O$^-$,
—(OCONH)$_q$-L-G or —(OCONH)$_q$-L-M, provided that only one of the substituents $R_1$ to $R_6$ is a group —$OPO_3^{2-}$, —OPO(OH)$_2$ or —OPO(OH)O$^-$, and one or two of the other substituents $R_1$ to $R_6$ is one of the groups —(OCONH)$_q$-L-G or —(OCONH)$_q$-L-M, the other substituents $R_1$ to $R_6$ being the groups —OH;
where:
L is a linkage group,
G is a reactive group,
M is a conjugated substance or molecule chosen from the following group: a tracer, an immunogen, a member of the pair of binding partners, a solid support,
q is equal to 1.
2. The compound as claimed in claim 1, of formula (II):

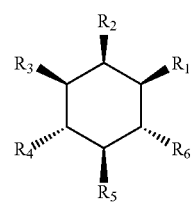

(II)

in which:
one of the substituents $R_1$, $R_3$, $R_4$ or $R_5$ is chosen from the groups —$OPO_3^{2-}$, —OPO(OH)$_2$ or —OPO(OH)O$^-$, one or two of the other substituents $R_1$-$R_6$ is chosen from the groups —(OCONH)$_q$-L-G or —(OCONH)$_q$-L-M, the other substituents are OH groups,
where:
L is a linkage group;
G is a reactive group;
M is a conjugated substance or molecule chosen from the following group: a tracer, an immunogen, a member of a pair of binding partners, a solid support;
q is equal to 1.

3. The compound as claimed in claim 1, of formula (III):

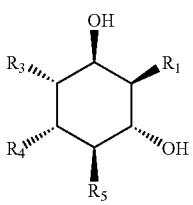

(III)

in which:
one of the substituents $R_1$, $R_4$, $R_5$ is chosen from: —OPO$_3^{2-}$, —OPO(OH)$_2$ or —OPO(OH)O$^-$,
$R_3$ is chosen from: —(OCONH)$_q$-L-G or —(OCONH)$_q$-L-M,
the other substituents $R_1$, $R_4$ and $R_5$ are groups OH, —(OCONH)$_q$-L-G or —(OCONH)$_q$-L-M, at least one of them being an —OH group,
where:
L is a linkage group;
G is a reactive group;
M is a conjugated substance or molecule chosen from the following group: a tracer, an immunogen, a member of a pair of binding partners, a solid support;
q is equal to 1.

4. The compound as claimed in claim 1, of formula (IV):

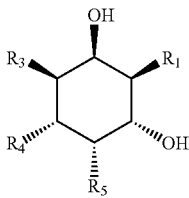

(IV)

in which:
one of the substituents $R_1$, $R_3$, $R_4$ is chosen from: —OPO$_3^{2-}$, —OPO(OH)$_2$ or —OPO(OH)O$^-$;
$R_5$ is chosen from: —(OCONH)$_q$-L-G or —(OCONH)$_q$-L-M,
the other substituents $R_1$, $R_3$ and $R_4$ are OH, —(OCONH)$_q$-L-G or —(OCONH)$_q$-L-M groups, at least one of them being an —OH group,
where:
L is a linkage group;
G is a reactive group;
M is a conjugated substance or molecule chosen from the following group: a tracer, an immunogen, a member of a pair of binding partners, a solid support;
q is equal to 1.

5. The compound as claimed in claim 1, of formula (V):

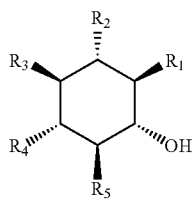

(V)

in which:
one of the substituents $R_1$, $R_3$, $R_4$, $R_5$ is chosen from: —OPO$_3^{2-}$, —OPO(OH)$_2$ or —OPO(OH)O$^-$,
$R_2$ is chosen from: —(OCONH)$_q$-L-G or —(OCONH)$_q$-L-M,
the other substituents $R_1$, $R_3$, $R_4$ and $R_5$ are OH, —(OCONH)$_q$-L-G or —(OCONH)$_q$-L-M groups, at least one of them being an —OH group,
where:
L is a linkage group;
G is a reactive group;
M is a conjugated substance or molecule chosen from the following group: a tracer, an immunogen, a member of a pair of binding partners, a solid support;
q is equal to 1.

6. The compound as claimed in claim 1 of formula (VI):

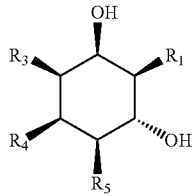

(VI)

in which:
one of the substituents $R_1$, $R_3$, $R_5$ is chosen from: —OPO$_3^{2-}$, —OPO(OH)$_2$ or —OPO(OH)O$^-$,
$R_4$ is chosen from: —(OCONH)$_q$-L-G or —(OCONH)$_q$-L-M,
the other substituents $R_1$, $R_3$ and $R_5$ are OH, —(OCONH)$_q$-L-G or —(OCONH)$_q$-L-M groups, at least one of them being an —OH group,
where:
L is a linkage group;
G is a reactive group;
M is a conjugated substance or molecule chosen from the following group: a tracer, an immunogen, a member of a pair of binding partners, a solid support;
q is equal to 1.

7. The compound as claimed in claim 1, characterized in that the group $R_1$ is chosen from the groups —OPO$_3^{2-}$, —OPO(OH)$_2$ or —OPO(OH)O$^-$.

8. The compound as claimed in claim 1, characterized in that the group $R_4$ is chosen from the groups —OPO$_3^{2-}$, —OPO(OH)$_2$ or —OPO(OH)O$^-$.

9. The compound as claimed in claim 1, characterized in that the linkage group L is a single covalent bond or a spacer arm comprising from 1 to 20 atoms different from hydrogen, chosen from carbon, nitrogen, phosphorus, oxygen and sulfur atoms, this linkage group being linear or branched, cyclic or heterocyclic, saturated or unsaturated, and consisting of a combination of bonds chosen from: carbon-carbon bonds which may be single, double, triple or aromatic; carbon-nitrogen bonds; nitrogen-nitrogen bonds; carbon-oxygen bonds; carbon-sulfur bonds; phosphorus-oxygen bonds; phosphorus-nitrogen bonds; ether bonds; ester bonds; thioether bonds; amine bonds; amide bonds; carboxamide bonds; sulfonamide bonds; urea bonds; urethane bonds; hydrazine bonds; carbamoyl bonds.

10. The compound as claimed in claim 9, characterized in that the linkage group L comprises from 1 to 20 atoms, different from hydrogen, chosen from carbon, nitrogen, phosphorus, oxygen and sulfur atoms and additionally comprises at least one bond chosen from ether, thioether, carboxamide, sulfonamide, hydrazine, amine and ester bonds, and aromatic or heteroaromatic bonds.

11. The compound as claimed in claim 9, characterized in that the linkage group L is chosen from the following substituted or unsubstituted chains: polymethylene, arylene, alkylarylene, arylenealkyl, arylthio or $C_3$-$C_{10}$ alkylenyl.

12. The compound as claimed in claim 1, characterized in that the reactive group G is chosen from the groups derived from the following compounds: an acrylamide, an activated amine including but not limited to a cadaverine or an ethylenediamine, an activated ester, an aldehyde, an alkyl halide, an anhydride, an aniline, an azide, an aziridine, a carboxylic acid, a diazoalkane, a haloacetamide, a halotriazine, such as monochlorotriazine, dichlorotriazine, a hydrazine, including but not limited to hydrazides, an imido ester, an isocyanate, an isothiocyanate, a maleimide, a sulfonyl halide, or a thiol, a ketone, an amine, an acid halide, a hydroxysuccinimidyl ester, a hydroxysulfosuccinimidyl ester, an azidonitrophenyl, an azidophenyl, a 3-(2-pyridyldithio)-propionamide, glyoxal and the groups of formula:

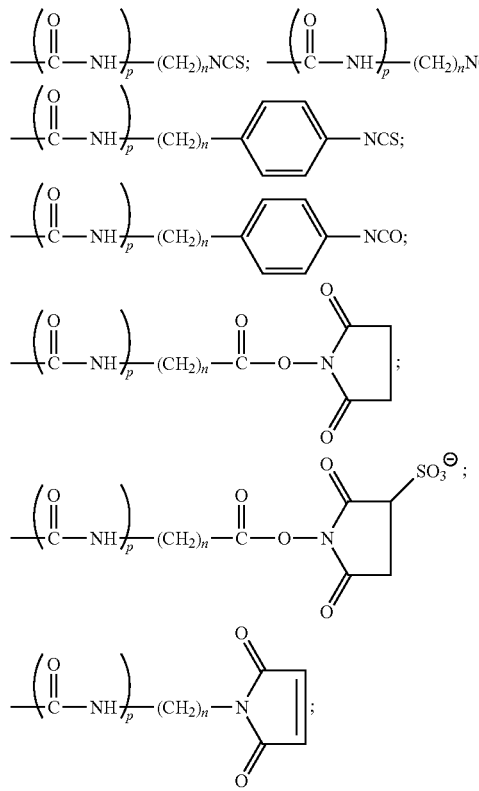

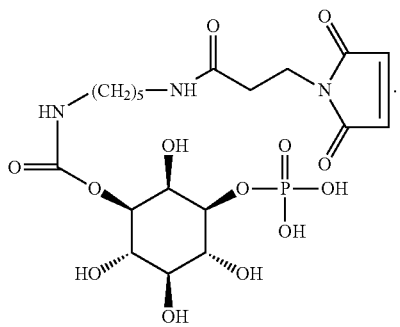

where n varies from 0 to 8 and p is equal to 0 or 1, and Ar is a 5- or 6-membered heterocycle comprising 1 to 3 heteroatoms, optionally substituted with a halogen atom.

13. The compound as claimed in claim 1, characterized in that L is a $C_3$-$C_{10}$ alkylenyl, and in that G is an amine group and M is an enzyme or fluorescent compound.

14. The compound as claimed in claim 1, of formula:

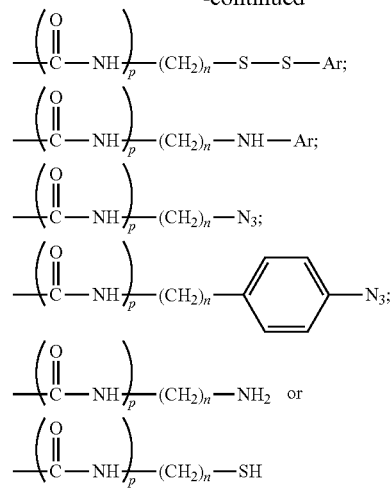

15. The compound as claimed in claim 1, characterized in that the conjugated substance or molecule M is a tracer.

16. The compound as claimed in claim 15, characterized in that the conjugated substance or molecule M is a tracer chosen from: a radioisotope, a radiolabeled molecule, a fluorescent compound, a luminescent compound, an enzyme, a fluorescent chromophore, a light-absorbing chromophore, or any other molecule or substance allowing direct or indirect quantitative measurement, provided that when M is a radioelement and L is a single bond, then M is different from tritium.

17. The compound as claimed in claim 16, characterized in that the conjugated substance or molecule M is a radioisotope chosen from: $^{125}I$, $^{32}P$, $^{35}S$ or a molecule labeled with one of the following isotopes: $^{125}I$, $^{32}P$, $^{35}S$ or $^{3}H$, with the exception of a phosphate group labeled with $^{32}P$.

18. The compound as claimed in claim 16, characterized in that the conjugated substance or molecule M is an enzyme or a fluorescent compound chosen from: rhodamines, cyanines, squaraines, BODIPYs, fluoresceins, compounds of the AlexaFluor family, rare-earth chelates, rare-earth cryptates, quantum dots, phycobiliproteins such as B-phycoerythrin, R-phycoerythrin, C-phycocyanin, allophycocyanin, GFP and its derivatives, a coral fluorescent protein, a peroxidase, a luciferase.

19. The compound as claimed in claim 1, characterized in that the conjugated substance or molecule M is a member of the pair of binding partners chosen from the pairs: avidin or streptavidin/biotin, haptene/antibodies including but not limited to 6HIS/anti-6HIS antibodies, FLAG/anti-FLAG antibodies, haptene/antibodies, DNP/anti-DNP antibodies, GST/anti-GST antibodies, Cmyc/anti-Cmyc antibodies, HA/anti-HA antibodies, single-stranded oligonucleotide/complementary single-stranded oligonucleotide.

20. The compound as claimed in claim 1, characterized in that the conjugated substance or molecule M is an immunogenic compound.

21. The compound as claimed in claim 20, characterized in that the conjugated substance or molecule M is an immunogenic compound chosen from: bovine serum albumin (BSA), cationic BSA (cBSA), KLH (keyhole limpet hemocyanin), thyroglobulin, ovalbumin, a liposome, a polymer of L-lysine or of L-glutamic acid, ficoll, dextran, or even polyethylene glycol.

22. The compound as claimed in claim 1, characterized in that the conjugated substance or molecule M is a solid support.

23. The compound as claimed in claim 22, characterized in that the conjugated substance or molecule M is a solid support chosen from: magnetic or nonmagnetic microbeads, microplate wells, tubes, a solid phase, a fluorescent microsphere.

24. A kit for assaying IP1 comprising:
an IP1 analog as claimed in claim 1, and
a ligand specific for IP1,
at least one of these components being directly or indirectly labeled with a tracer.

25. The kit as claimed in claim 24, characterized in that it additionally comprises an agent blocking certain enzymes of the inositol cycle, in particular lithium chloride.

26. The kit as claimed in claim 24, characterized in that the ligand specific for IP1 is a monoclonal or polyclonal antibody specific for IP1.

27. The kit for assaying IP1 as claimed in claim 24, characterized in that the tracer is chosen from: a radioelement, a fluorescent compound, a luminescent compound, an enzyme, a fluorescent chromophore, a light-absorbing chromophore, or any other molecule or substance allowing a direct or indirect quantitative measurement.

28. The kit as claimed in claim 24, characterized in that it contains a donor compound and an acceptor compound emitting a signal resulting from a proximity transfer with the donor compound, the donor compound being directly or indirectly linked to the IP1 analog, and the acceptor compound being directly or indirectly linked to the ligand specific for IP1.

29. The kit as claimed in claim 24, characterized in that it contains a donor compound and an acceptor compound emitting a signal resulting from a proximity transfer with the donor compound, the acceptor compound being directly or indirectly linked to the IP1 analog, and the donor compound being directly or indirectly linked to the ligand specific for IP1.

30. The kit as claimed in claim 24, characterized in that the donor compound and the acceptor compound are fluorescent compounds, in that the proximity transfer is an energy transfer and in that the emitted signal is a fluorescent signal.

31. The compound as claimed in claim 9, characterized in that L is chosen from the groups:

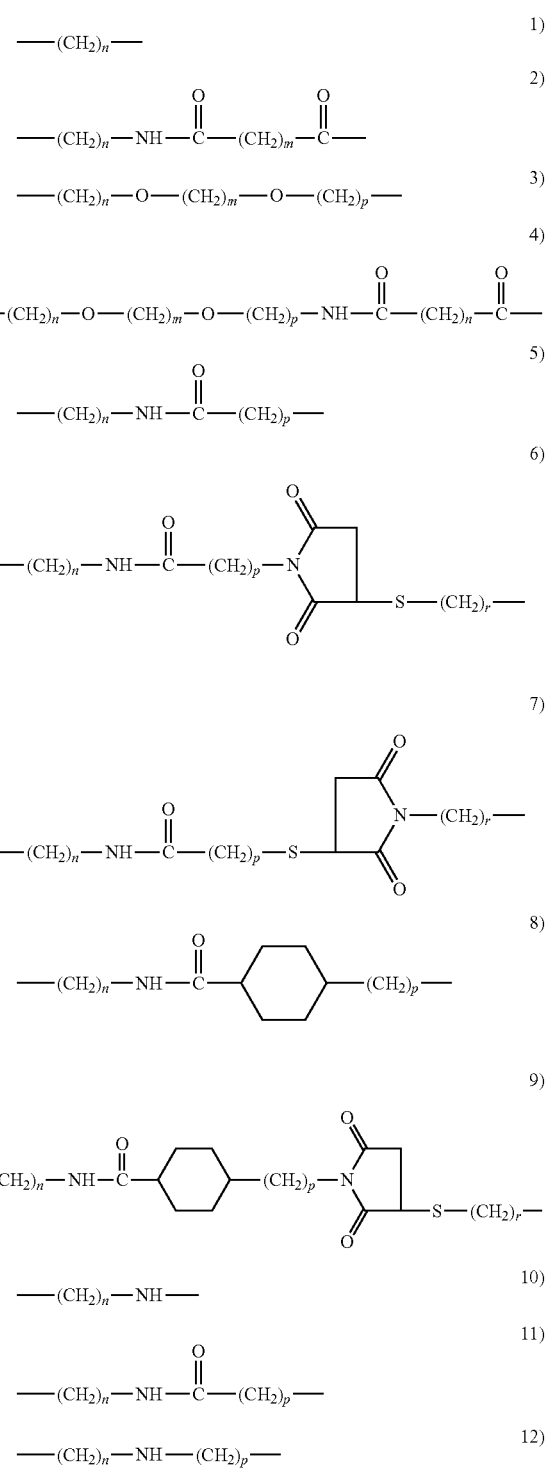

in which:

n and m are integers from 2 to 16;

p and r are integers from 1 to 16.

32. The compound as claimed in claim 31, characterized in that:

n and m are integers from 2 to 8;

p and r are integers from 1 to 5.

33. A compound of formula (I):

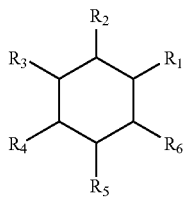
(I)

in which:
the substituents $R_1$, $R_2$, $R_3$, $R_4$, $R_5$, $R_6$ are chosen from: —OH, —OPO$_3^{2-}$, —OPO(OH)$_2$ or —OPO(OH)O$^-$, —(OCONH)$_q$-L-G or —(OCONH)$_q$-L-M, provided that only one of the substituents $R_1$ to $R_6$ is a group —OPO$_3^{2-}$, —OPO(OH)$_2$ or —OPO(OH)O$^-$ and one or two of the other substituents $R_1$ to $R_6$ is one of the groups —(OCONH)$_q$-L-G or —(OCONH)$_q$-L-M, the other substituents $R_1$ to $R_6$ being the groups —OH;
where:
q is equal to 0;
G is a reactive group,
M is a conjugated substance or molecule chosen from the following group: a tracer, an immunogen, a member of the pair of binding partners, a solid support,
L is a linkage group chosen from the groups:

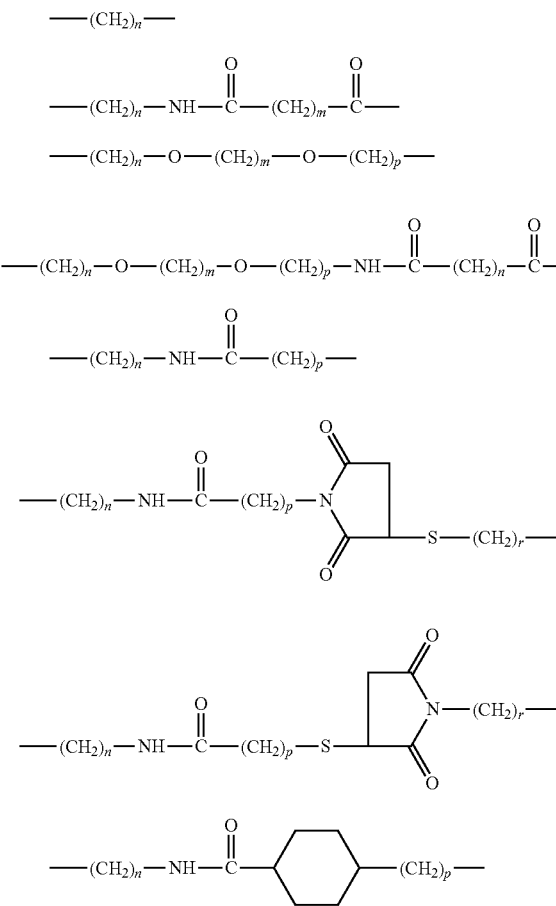

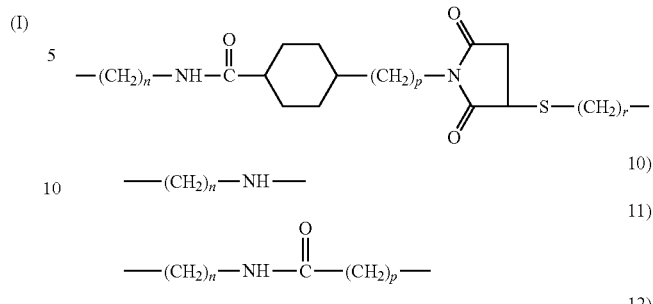

in which:
n and m are integers from 2 to 16;
p and r are integers from 1 to 16.

34. The compound as claimed in claim 33, characterized in that:
n and m are integers from 2 to 8;
p and r are integers from 1 to 5.

35. The compound as claimed in claim 33, of formula (II):

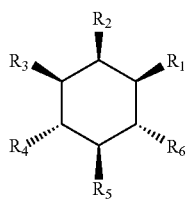
(II)

in which:
one of the substituents $R_1$, $R_3$, $R_4$ or $R_5$ is chosen from the groups —OPO$_3^{2-}$, -OPO(OH)$_2$ or —OPO(OH)O$^-$,
one or two of the other substituents $R_1$-$R_6$ is chosen from the groups —(OCONH)$_q$-L-G or —(OCONH)$_q$-L-M,
the other substituents are OH groups,
where:
L is a linkage group as defined in claim 33;
G is a reactive group;
M is a conjugated substance or molecule chosen from the following group: a tracer, an immunogen, a member of a pair of binding partners, a solid support;
q is equal to 0.

36. The compound as claimed in claim 33, of formula (III):

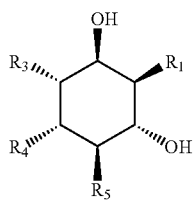
(III)

in which:
one of the substituents $R_1$, $R_4$, $R_5$ is chosen from: —OPO$_3^{2-}$, —OPO(OH)$_2$ or —OPO(OH)O$^-$,
$R_3$ is chosen from: —(OCONH)$_q$-L-G or —(OCONH)$_q$-L-M, the other substituents $R_1$, $R_4$ and $R_5$ are groups OH, —(OCONH)$_q$-L-G or —(OCONH)$_q$-L-M, at least one of them being an —OH group, where:
L is a linkage group as defined in claim 33;
G is a reactive group;
M is a conjugated substance or molecule chosen from the following group: a tracer, an immunogen, a member of a pair of binding partners, a solid support;
q is equal to 0.

37. The compound as claimed in claim 3, of formula (IV):

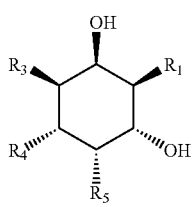

(IV)

in which:
one of the substituents $R_1$, $R_3$, $R_4$ is chosen from: —OPO$_3^{2-}$, —OPO(OH)$_2$ or —OPO(OH)O$^-$,
$R_5$ is chosen from: —(OCONH)$_q$-L-G or —(OCONH)$_q$-L-M,
the other substituents $R_1$, $R_3$ and $R_4$ are OH, —(OCONH)$_q$-L-G or —(OCONH)$_q$-L-M groups, at least one of them being an —OH group,
where:
L is a linkage group as defined in claim 33;
G is a reactive group;
M is a conjugated substance or molecule chosen from the following group: a tracer, an immunogen, a member of a pair of binding partners, a solid support;
q is equal to 0.

38. The compound as claimed in claim 33, of formula (V):

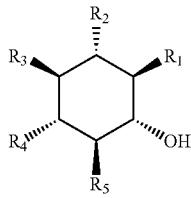

(V)

in which:
one of the substituents $R_1$, $R_3$, $R_4$, $R_5$ is chosen from: —OPO$_3^{2-}$, —OPO(OH)$_2$ or —OPO(OH)O$^-$,
$R_2$ is chosen from: —(OCONH)$_q$-L-G or —(OCONH)$_q$-L-M,
the other substituents $R_1$, $R_3$, $R_4$ and $R_5$ are OH, —(OCONH)$_q$-L-G or —(OCONH)$_q$-L-M groups, at least one of them being an —OH group,
where:
L is a linkage group as defined in claim 33;
G is a reactive group;
M is a conjugated substance or molecule chosen from the following group: a tracer, an immunogen, a member of a pair of binding partners, a solid support;
q is equal to 0.

39. The compound as claimed in claim 33, of formula (VI):

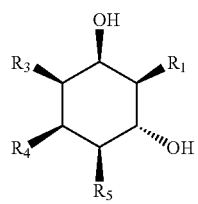

(VI)

in which:
one of the substituents $R_1$, $R_3$, $R_5$ is chosen from: —OPO$_3^{2-}$, —OPO(OH)$_2$ or —OPO(OH)O$^-$,
$R_4$ is chosen from: —(OCONH)$_q$-L-G or —(OCONH)$_q$-L-M,
the other substituents $R_1$, $R_3$ and $R_5$ are OH, —(OCONH)$_q$-L-G or —(OCONH)$_q$-L-M groups, at least one of them being an —OH group,
where:
L is a linkage group as defined in claim 33;
G is a reactive group;
M is a conjugated substance or molecule chosen from the following group: a tracer, an immunogen, a member of a pair of binding partners, a solid support;
q is equal to 0.

40. The compound as claimed in claim 33, characterized in that the group $R_1$ is chosen from the groups —OPO$_3^{2-}$, —OPO(OH)$_2$ or —OPO(OH)O$^-$.

41. The compound as claimed in claim 33, characterized in that the group $R_4$ is chosen from the groups —OPO$_3^{2-}$, —OPO(OH)$_2$ or —OPO(OH)O$^-$.

42. The compound as claimed in claim 33, characterized in that the reactive group G is chosen from the groups derived from the following compounds: an acrylamide, an activated amine including but not limited to a cadaverine or an ethylenediamine, an activated ester, an aldehyde, an alkyl halide, an anhydride, an aniline, an azide, an aziridine, a carboxylic acid, a diazoalkane, a haloacetamide, a halotriazine, such as monochlorotriazine, dichlorotriazine, a hydrazine, including but not limited to hydrazides, an imido ester, an isocyanate, an isothiocyanate, a maleimide, a sulfonyl halide, or a thiol, a ketone, an amine, an acid halide, a hydroxysuccinimidyl ester, a hydroxysulfosuccinimidyl ester, an azidonitrophenyl, an azidophenyl, a 3-(2-pyridyldithio)-propionamide, glyoxal and groups of formula:

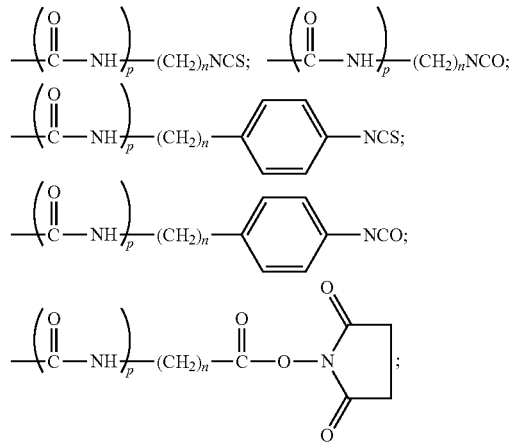

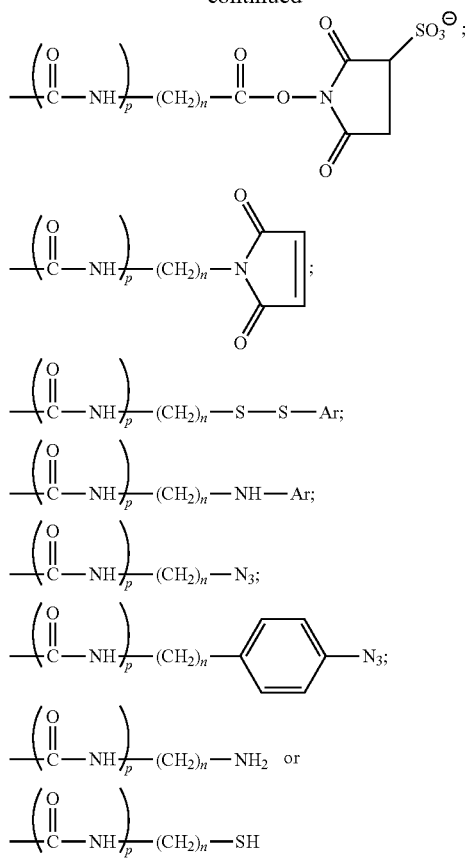

where n varies from 0 to 8 and p is equal to 0 or 1, and Ar is a 5- or 6-membered heterocycle comprising 1 to 3 heteroatoms, optionally substituted with a halogen atom.

43. The compound as claimed in claim 33, characterized in that the conjugated substance or molecule M is a tracer.

44. The compound as claimed in claim 43, characterized in that the conjugated substance or molecule M is a tracer chosen from: a radioisotope, a radiolabeled molecule, a fluorescent compound, a luminescent compound, an enzyme, a fluorescent chromophore, a light-absorbing chromophore, or any other molecule or substance allowing direct or indirect quantitative measurement 45. The compound as claimed in claim 44, characterized in that the conjugated substance or molecule M is a radioisotope chosen from: $^{125}$I, $^{32}$P, $^{35}$S or a molecule labeled with one of the following isotopes: $^{125}$I, $^{32}$P, $^{35}$S or $^{3}$H, with the exception of a phosphate group labeled with $^{32}$P.

46. The compound as claimed in claim 44, characterized in that the conjugated substance or molecule M is an enzyme or a fluorescent compound chosen from: rhodamines, cyanines, squaraines, BODIPYs, fluoresceins, compounds of the AlexaFluor family, rare-earth chelates, rare-earth cryptates, quantum dots, phycobiliproteins such as B-phycoerythrin, R-phycoerythrin, C-phycocyanin, allophycocyanin, GFP and its derivatives, a coral fluorescent protein, a peroxidase, a luciferase.

47. The compound as claimed in claim 33, characterized in that the conjugated substance or molecule M is a member of the pair of binding partners chosen from the pairs: avidin or streptavidin/biotin, haptene/antibodies including but not limited to 6HIS/anti-6HIS antibodies, FLAG/anti-FLAG antibodies, haptene/antibodies, DNP/anti-DNP antibodies, GST/anti-GST antibodies, Cmyc/anti-Cmyc antibodies, HA/anti-HA antibodies, single-stranded oligonucleotide/complementary single-stranded oligonucleotide.

48. The compound as claimed in claim 33, characterized in that the conjugated substance or molecule M is an immunogenic compound.

49. The compound as claimed in claim 48, characterized in that the conjugated substance or molecule M is an immunogenic compound chosen from: bovine serum albumin (BSA), cationic BSA (cBSA), KLH (keyhole limpet hemocyanin), thyroglobulin, ovalbumin, a liposome, a polymer of L-lysine or of L-glutamic acid, ficoll, dextran, or even polyethylene glycol.

50. The compound as claimed in claim 33, characterized in that the conjugated substance or molecule M is a solid support.

51. The compound as claimed in claim 50, characterized in that the conjugated substance or molecule M is a solid support chosen from: magnetic or nonmagnetic microbeads, microplate wells, tubes, a solid phase, a fluorescent microsphere.

52. A kit for assaying IP1 comprising:
an IP1 analog as claimed in claims 33, and
a ligand specific for IP1,
at least one of these components being directly or indirectly labeled with a tracer.

53. The kit as claimed in claim 52, characterized in that it additionally comprises an agent blocking certain enzymes of the inositol cycle, in particular lithium chloride.

54. The kit as claimed in claim 52, characterized in that the ligand specific for IP1 is a monoclonal or polyclonal antibody specific for IP1.

55. The kit for assaying IP1 as claimed in claim 52, characterized in that the tracer is chosen from: a radioelement, a fluorescent compound, a luminescent compound, an enzyme, a fluorescent chromophore, a light-absorbing chromophore, or any other molecule or substance allowing a direct or indirect quantitative measurement.

56. The kit as claimed in claim 52, characterized in that it contains a donor compound and an acceptor compound emitting a signal resulting from a proximity transfer with the donor compound, the donor compound being directly or indirectly linked to the IP1 analog, and the acceptor compound being directly or indirectly linked to the ligand specific for IP1.

57. The kit as claimed in claim 52, characterized in that it contains a donor compound and an acceptor compound emitting a signal resulting from a proximity transfer with the donor compound, the acceptor compound being directly or indirectly linked to the IP1 analog, and the donor compound being directly or indirectly linked to the ligand specific for IP1.

58. The kit as claimed in claim 52, characterized in that the donor compound and the acceptor compound are fluorescent compounds, in that the proximity transfer is an energy transfer and in that the emitted signal is a fluorescent signal.

59. A compound of formula (I):

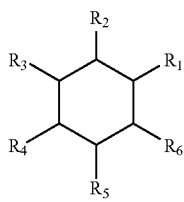

in which:
the substituents $R_1$, $R_2$, $R_3$, $R_4$, $R_5$, $R_6$ are chosen from: —OH, —OPO$_3^{2-}$, —OPO(OH)$_2$ or —OPO(OH)O$^-$, —(OCONH)$_q$-L-G or —(OCONH)$_q$-L-M, provided that only one of the substituents $R_1$ to $R_6$ is a group —OPO$_3^{2-}$, —OPO(OH)$_2$ or —OPO(OH)O$^-$ and one or two of the other substituents $R_1$ to $R_6$ is one of the groups —(OCONH)$_q$-L-G or —(OCONH)$_q$-L-M, the other substituents $R_1$ to $R_6$ being the groups —OH;
where:
L is a linkage group,
G is a reactive group,
M is a conjugated substance or molecule chosen from the following group: a tracer, an immunogen, a member of the pair of binding partners, a solid support,
q is equal to 0 or 1, and wherein at least one of $R_1$, $R_2$, $R_3$, $R_4$, $R_5$, $R_6$ is —(OCONH)$_q$-L-M.

60. The compound as claimed in claim 59, characterized in that the conjugated substance or molecule M is a tracer.

61. The compound as claimed in claim 60, characterized in that the conjugated substance or molecule M is a tracer chosen from: a radioisotope, a radiolabeled molecule, a fluorescent compound, a luminescent compound, an enzyme, a fluorescent chromophore, a light-absorbing chromophore, or any other molecule or substance allowing direct or indirect quantitative measurement, provided that when M is a radioelement and L is a single bond, then M is different from tritium.

62. The compound as claimed in claim 61, characterized in that the conjugated substance or molecule M is a radioisotope chosen from: $^{125}$I, $^{32}$P, $^{35}$S or a molecule labeled with one of the following isotopes: $^{125}$I, $^{32}$P, $^{35}$S or $^3$H, with the exception of a phosphate group labeled with $^{32}$P.

63. The compound as claimed in claim 60, characterized in that the conjugated substance or molecule M is an enzyme or a fluorescent compound chosen from: rhodamines, cyanines, squaraines, BODIPYs, fluoresceins, compounds of the AlexaFluor family, rare-earth chelates, rare-earth cryptates, quantum dots, phycobiliproteins such as B-phycoerythrin, R-phycoerythrin, C-phycocyanin, allophycocyanin, GFP and its derivatives, a coral fluorescent protein, a peroxidase, a luciferase.

64. The compound as claimed in claim 59, characterized in that the conjugated substance or molecule M is a member of the pair of binding partners chosen from the pairs: avidin or streptavidin/biotin, haptene/antibodies including but not limited to 6HIS/anti-6HIS antibodies, FLAG/anti-FLAG antibodies, haptene/antibodies, DNP/anti-DNP antibodies, GST/anti-GST antibodies, Cmyc/anti-Cmyc antibodies, HA/anti-HA antibodies, single-stranded oligonucleotide/complementary single-stranded oligonucleotide.

65. The compound as claimed in claim 59, characterized in that the conjugated substance or molecule M is an immunogenic compound.

66. The compound as claimed in claim 65, characterized in that the conjugated substance or molecule M is an immunogenic compound chosen from: bovine serum albumin (BSA), cationic BSA (cBSA), KLH (keyhole limpet hemocyanin), thyroglobulin, ovalbumin, a liposome, a polymer of L-lysine or of L-glutamic acid, ficoll, dextran, or even polyethylene glycol.

* * * * *